United States Patent
He et al.

(10) Patent No.: US 12,385,058 B2
(45) Date of Patent: Aug. 12, 2025

(54) HERBICIDE TOLERANCE PROTEIN, ENCODING GENE THEREOF AND USE THEREOF

(71) Applicants: Beijing Dabeinong Biotechnology Co., Ltd., Beijing (CN); Nanjing Agricultural University, Nanjing (CN)

(72) Inventors: Jian He, Nanjing (CN); Bin Liu, Nanjing (CN); Qian Peng, Nanjing (CN); Qing Tao, Beijing (CN); Xiang Xiao, Beijing (CN); Xiaoming Bao, Beijing (CN)

(73) Assignee: Beijing Dabeinong Biotechnology Co., Ltd., Beijing (CN)

( * ) Notice: Subject to any disclaimer, the term of this patent is extended or adjusted under 35 U.S.C. 154(b) by 472 days.

(21) Appl. No.: 16/967,815

(22) PCT Filed: Dec. 28, 2018

(86) PCT No.: PCT/CN2018/124916
§ 371 (c)(1),
(2) Date: Aug. 6, 2020

(87) PCT Pub. No.: WO2019/153952
PCT Pub. Date: Aug. 15, 2019

(65) Prior Publication Data
US 2021/0324404 A1  Oct. 21, 2021

(30) Foreign Application Priority Data
Feb. 7, 2018  (CN) .......................... 201810124124.9

(51) Int. Cl.
C12N 15/82  (2006.01)
A01N 47/36  (2006.01)
C12N 9/14  (2006.01)

(52) U.S. Cl.
CPC ......... *C12N 15/8278* (2013.01); *A01N 47/36* (2013.01); *C12N 9/14* (2013.01); *C12N 15/8202* (2013.01); *C12N 15/8275* (2013.01)

(58) Field of Classification Search
None
See application file for complete search history.

(56) References Cited

U.S. PATENT DOCUMENTS

| 2014/0325700 A1 | 10/2014 | Li et al. |
| 2019/0029252 A1 | 1/2019 | Xie et al. |
| 2019/0029257 A1 | 1/2019 | Xie et al. |
| 2019/0106705 A1 | 4/2019 | Xie et al. |
| 2019/0249187 A1 | 8/2019 | He et al. |

FOREIGN PATENT DOCUMENTS

EP  3608411 A1  2/2020

OTHER PUBLICATIONS

Hang et al, Appl. Environ. Microbiol. (2012) 78:1962-1968.*
Cunningham et al, Science (1989) 244:1081-1085.*
GenBank Accession No. JN617866, submitted Aug. 9, 2011, version of Feb. 28, 2012.*
Arnold et al, Ed., Directed Evolution Library Creation, Methods and Protocols, Humana Press 2003.*
Castle et al, Science (2004) 304:1151-1154.*
Dillon et al, J. Biol. Chem. (2013) 39:27872-27880.*
Lei et al, Environ. Res. (2023) 235:116570.*
Hang, B. et al., SulE, a Sulfonylurea Herbicide De-Esterification Esterase from Hansschlegelia zhihuaiae S113, Applied and Environmental Microbiology, 78(6): 1962-1968, Mar. 2012.
English Translation of Office Action for Chinese Patent Application No. No. 201810124124.9, May 7, 2019.
English Translation Office Action for Chinese Patent Application No. No. 201810124124.9, Dec. 3, 2019.
English translation of Chinese Search Report for Chinese Application No. 201810124124.9, Mar. 29, 2019.
Brazilian Office Action for Brazilian Application No. BR112020015958, dated Mar. 1, 2024.
English Language Concise Explanation for Brazilian Office Action for Brazilian Application No. BR112020015958, dated Mar. 1, 2024.

* cited by examiner

Primary Examiner — Mykola V. Kovalenko
(74) Attorney, Agent, or Firm — Julie K. Staple; Fishman Stewart PLLC

(57) ABSTRACT

The present invention relates to an herbicide tolerance protein, an encoding gene thereof and use thereof, the herbicide tolerance protein comprising: a protein (a) having an amino acid sequence as shown in SEQ ID NO: 1, and having an alanine substitution at least at position 176 and/or having a valine substitution at position 178 of SEQ ID NO: 1; or (b) having an amino acid sequence as shown in SEQ ID NO: 3; or (c) having an amino acid sequence as shown in SEQ ID NO: 5; or (d) having an amino acid sequence as shown in SEQ ID NO: 7; or (e) being derived from (a) by means of the amino acid sequence of (a) undergoing substitution and/or deletion and/or by added one or several amino acids, and having the activity of thifensulfuron hydrolase. The herbicide tolerance protein of the present invention has a broad application prospects in plants.

9 Claims, 6 Drawing Sheets
Specification includes a Sequence Listing.

SEQUENCE LISTING

<160> NUMBER OF SEQ ID NOS: 82

<210> SEQ ID NO 1
<211> LENGTH: 398
<212> TYPE: PRT
<213> ORGANISM: Methylophilus sp.

<400> SEQUENCE: 1

```
Met Gly Thr Ala Leu Leu Thr Gly Thr Ser Ala Ala Ser Pro Val Leu
1               5                   10                  15

Ala Ala Gly Thr Gly Ala Ile Gly Ile Ala Thr Leu Pro Leu Ser Thr
                20                  25                  30

Ala Thr Ala Pro Ala Gly Thr Ala Ala Val Gly Leu Ala Gly Ser Leu
            35                  40                  45

Ala Leu Val Val Leu Ala Gly Gly Ser Pro Thr Ile Gly Gly Ala
        50                  55                  60

Thr Val Thr Gly Pro Gly Leu Pro Ala Pro Ser Leu Pro Val Ile Pro
65                  70                  75                  80

Thr Ser Ala Gly Gly Ala Thr Pro Thr Ile Ala Gly Met Thr Val Ala
                85                  90                  95

Pro Gly Ala Pro Val Ala Pro Ala Gly Leu Pro Leu Val Pro Thr His
                100                 105                 110

Gly Gly Gly Leu Thr Gly His Ile Thr Gly Ser Thr Pro Ala Gly Ala
            115                 120                 125

Pro Gly Pro Gly Thr Leu Pro Val Gly Ala Ala His Thr Val Thr Thr
        130                 135                 140

Ile Ala Gly Pro Gly Ala Gly Ala Gly Ala Ile Pro Thr Pro Ala Gly
145                 150                 155                 160

Pro Pro Gly Gly Leu Gly Gly Gly Ser Ile Val Ala Thr Val Thr Gly
                165                 170                 175

Ala Ser Ser Leu Gly Gly Ala Thr Val Ala Ala Ala Leu Gly Pro Ala
                180                 185                 190

Pro Gly Gly Pro Pro Gly Ala Ser Gly Pro Pro Ala Gly Thr Gly Ala
            195                 200                 205

Ala Thr Pro Leu Gly Met Gly Pro Ser Pro Ser Ile Ser Ser Ala Gly
        210                 215                 220

Ile Val Ala Ala Val Val Leu Leu Val Thr His Ile Gly Pro Cys Val
225                 230                 235                 240

Leu Val Thr His Ser Ala Ser Gly Val Leu Gly Met Ala Val Ala Thr
                245                 250                 255

His Ala Leu Ala Val Ala Gly Ile Val Ala Thr Gly Pro Ala Thr Ser
            260                 265                 270
```

```
Ile Pro Pro Leu Gly Leu Val Pro Gly Ile Pro Leu Ala Ala Leu
            275                 280                 285

Leu Ser Gly Ile Pro Pro Pro Gly Ile Gly Gly Ser Thr Pro Leu
            290                 295                 300

Leu Leu Ala Leu Ile Pro Ile Gly Pro Val Pro Gly Ala Ala Ile Pro
305                 310                 315                 320

Leu Ala Pro Leu Ser Ala Thr Thr Pro Leu Ala Thr Thr Ala Val Thr
                    325                 330                 335

Ala Thr Ala His Ser Leu Ser Leu Gly Ala Ile Ala Leu Leu Gly Gly
                340                 345                 350

Gly Ala Ser Leu Leu Ala Leu Pro Thr Ala Gly Leu Ala Gly Ala Thr
            355                 360                 365

His Pro Pro Pro Thr Ala Ala Ala Ala Val Gly Val Ala Ser Leu Leu
370                 375                 380

Ser Ala Pro Leu Gly Leu His Gly Leu Ala Gly Ala Gly Ser
385                 390                 395

<210> SEQ ID NO 2
<211> LENGTH: 1197
<212> TYPE: DNA
<213> ORGANISM: Methylophilus sp.

<400> SEQUENCE: 2
atggaaaccg ataaaaaaac cggaacgtcc cgcagatcat tgtgaaggc tgctggaacc      60 ggcgcaatag gaatagcgac gctgccgctt tcgactgcaa ctgctttcgc ggaaactgac     120
aacgtggagc ttgcccaatc gaagcggaag gttgtccttg ctgaacaagg cagtttctac     180
atcgggggca gaacagtaac cgggcctgga aaattcgatc cgtcaaagcc ggtaattcca     240
tattccaacg aaggtgccac gttttatatc aatcaaatgt acgtaaactt tcaagctcct     300
gtgcgccctc gtgggctgcc tctagtcttt tggcatgggg gcggactaac cggccatatc     360
tgggaatcta ccccagacgg ccgccccgga tttcagaccc tctttgttca agatcggcat     420
acggtctaca cgattgatca gccagggcgc ggaaggggca atattcctac ctttaatggc     480
ccttttgggc agttggaaga gagtcgatt gttaacactg ttaccggaaa ctccagtaaa     540
gaaggagcgt gggttagaga tcgactaggg cccgctcccg gccagttttt tgagaacagc     600
caattcccac gtggttatga agacaactac ttcaaggaga tggggttcag tccgtcgatc     660
tcatcagatg agatagtcga cgctgttgtt aaactagtaa ctcacatagg tccttgtgtt     720
ctggtgaccc attcggcttc cggagtactg ggcatgcgag tcgcgacaca cgccaagaac     780
gtgaggggga tcgttgctta tgagcctgcg acaagtatct ttcccaaagg aaaagtgcct     840
gagataccgc ctctcgccga taaaaagtcg caaattttcc cgccgttcga gatccaggag     900 tcttactta agaagctcgc gaagataccc attcagtttg tcttcggaga taatatcccc     960
aagaacccta atccgccta ttggttcttg gactggtgga gagtcactcg ctacgctcac    1020
agcttgtcac tcgaggctat caataagctc ggtggtcaag cgtctctttt ggatttgccg    1080
actgcgggac ttcgcggcaa cacgcatttt ccattcaccg accggaataa cgtgcaggtc    1140
gcttctctgt tatctgattt cctcggaaag cacggcttag atcagaacga aagctga       1197

<210> SEQ ID NO 3
<211> LENGTH: 1197
<212> TYPE: DNA
<213> ORGANISM: Artificial Sequence
<220> FEATURE:
<223> OTHER INFORMATION: the ALT01-01 nucleotide sequence encoding the
``` amino acid sequence corresponding to ALT01 and based on soybean
codon usage bias

<400> SEQUENCE: 3

```
atggagactg ataagaaaac tggcacatct agaaggtcat tgttaaggc tgcaggaaca        60
ggtgccattg gaatcgctac ccttccattg tccaccgcca ctgctttcgc agagactgat      120
aacgtggaac tcgcccaatc taagagaaag gtggtgctgg ctgaacaagg gtcattttac      180
ataggggta ggactgttac tggtcctggc aagtttgatc catccaaacc tgtgataccc       240
tacagtaacg aaggagcaac attctatatt aaccaaatgt atgttaactt ccaggcccca      300
gtgagaccta ggggacttcc attggttttc tggcatggag gtggcttgac tggtcacatc      360
tgggagtcta cacctgacgg cagacccggg tttcaaaccc tcttcgttca ggataggcat      420
accgtgtaca ctattgacca acctgggaga ggaaggggta acatcccaac ttttaacgga      480
cctttcggac agttggagga agagagtatt gttaacactg tgacaggaaa ttcttcaaag      540
gaaggtgcct gggtgagaga taggcttggc cctgctcccg gcaattttt cgagaactct       600
cagtttccta gaggctatga agacaattac tttaaggaga tgggattcag cccatctata      660
tccagtgatg aaattgttga cgctgttgtg aaactcgtga cccatattgg tccttgtgtt      720
ctggtgactc actcagcatc cggcgttctt gggatgagag tggctacaca cgcaaagaat      780
gttaggggaa ttgtggccta tgaaccagct acctcaatct tccccaaggg aaaagttcca      840
gagataccac ctctcgctga taagaaaagc caaatctttc ccccattcga aatacaggag      900
tcttacttta agaaacttgc caagattcca atccaatttg ttttcggaga taacatcccc      960
aagaatccaa atcagcata ttggttcctg gactggtgga gagtgacaag atacgcacat     1020
agtctcagcc tggaggccat aaacaaattg ggggacaag cttcccttttt ggatcttcct     1080
actgcaggat tgagaggtaa tacacacttt cccttcaccg ataggaacaa tgttcaggtg     1140
gcttctctcc tgtcagactt tctgggtaaa cacggtctgg atcaaaatga gagctga        1197
```

<210> SEQ ID NO 4
<211> LENGTH: 1197
<212> TYPE: DNA
<213> ORGANISM: Artificial Sequence
<220> FEATURE:
<223> OTHER INFORMATION: the ALT01-02 nucleotide sequence encoding the
amino acid sequence corresponding to the herbicide tolerant
protein ALT01 and based on the maize codon usage bias

<400> SEQUENCE: 4

```
atggagacag acaagaagac cggcacgtcc cgcaggagct cgtgaaggc tgctggcacc        60
ggggctatcg ggattgctac gctcccactg tcgacagcta ctgccttcgc ggagactgat      120
aacgtggagc tggcgcagag caagaggaag gtggttctgg ctgagcaggg gtcgttctac      180
attggggc ggactgtgac cgggcccggc aagttcgacc catcgaagcc tgtcattccg         240
tactctaacg agggcgctac gttctacatc aaccagatgt acgtgaattt ccaggctccc      300
gtccgcccaa ggggcctccc actggtgttc tggcacggcg gggcctgac aggccatatc       360
tgggagtcca ctccagatgg ccgcccaggg ttccagacac tcttcgttca ggacaggcac      420
acagtgtaca ctattgatca gccagggagg ggcaggggga catccctac cttcaatggc       480
ccattcgggc agctggagga ggagtccatc gtgaacaccg tcacgggcaa ttccagcaag      540
gaggggctt gggtcaggga ccggctcggc ccggccccag gcagttcttt cgagaactct       600
cagttccccc ggggctacga ggataattac ttcaaggaga tgggcttctc accatccatc      660
```

```
tcgtctgacg agattgtcga tgccgtggtc aagctcgtta cccacatcgg cccttgcgtt    720
ctggtgacgc atagcgcttc gggcgtcctc gggatgaggg ttgctacaca tgcgaagaac    780
gttcgcggca tcgtggctta cgagccggcc acttccattt tccccaaggg caaggtgcca    840
gagatcccac cactggccga caagaagtca cagatcttcc cacctttcga gattcaggag    900
tcctacttca agaagctcgc taagatcccc attcagttcg tgttcggcga caacattcct    960
aagaatccga gagcgcgta ctggttcctg gattggtggc gcgtcacgcg ctacgcgcac   1020
tctctctcac tggaggctat caacaagctc gggggccagg cctcgctcct ggacctccct   1080
accgctggcc tgaggggaa cacccatttc ccgttcacgg atcggaacaa tgtccaggtt   1140
gcgtccctcc tgagcgattt cctcggcaag cacgggctgg atcagaatga gtcttga     1197
```

<210> SEQ ID NO 5
<211> LENGTH: 22
<212> TYPE: DNA
<213> ORGANISM: Artificial Sequence
<220> FEATURE:
<223> OTHER INFORMATION: the primer 1 for error-prone PCR reaction of the ALT01 gene

<400> SEQUENCE: 5
atggaaaccg ataaaaaaac cg                                              22

<210> SEQ ID NO 6
<211> LENGTH: 22
<212> TYPE: DNA
<213> ORGANISM: Artificial Sequence
<220> FEATURE:
<223> OTHER INFORMATION: the primer 2 for error-prone PCR reaction of the ALT01 gene

<400> SEQUENCE: 6
tcagctttcg ttctgatcta ag                                              22

<210> SEQ ID NO 7
<211> LENGTH: 398
<212> TYPE: PRT
<213> ORGANISM: Artificial Sequence
<220> FEATURE:
<223> OTHER INFORMATION: the amino acid sequence of the herbicide tolerant protein ALT01M1

<400> SEQUENCE: 7

```
Met Glu Thr Asp Lys Lys Thr Gly Thr Ser Arg Arg Ser Phe Val Lys
1               5                   10                  15

Ala Ala Gly Thr Gly Ala Ile Gly Ile Ala Thr Leu Pro Leu Ser Thr
            20                  25                  30

Ala Thr Ala Phe Ala Glu Thr Asp Asn Val Glu Leu Ala Gln Ser Lys
        35                  40                  45

Arg Lys Val Val Leu Ala Glu Gln Gly Ser Phe Tyr Ile Gly Gly Arg
    50                  55                  60

Thr Val Thr Gly Pro Gly Lys Phe Asp Pro Ser Lys Pro Val Ile Pro
65                  70                  75                  80

Tyr Ser Asn Glu Gly Ala Thr Phe Tyr Ile Asn Gln Met Tyr Val Asn
                85                  90                  95

Phe Gln Ala Pro Val Arg Pro Arg Gly Leu Pro Leu Val Phe Trp His
            100                 105                 110

Gly Gly Gly Leu Thr Gly His Ile Trp Glu Ser Thr Pro Asp Gly Arg
        115                 120                 125
```

```
Pro Gly Phe Gln Thr Leu Phe Val Gln Asp Arg His Thr Val Tyr Thr
        130                 135                 140
Ile Asp Gln Pro Gly Arg Gly Arg Gly Asn Ile Pro Thr Phe Asn Gly
145                 150                 155                 160
Pro Phe Gly Gln Leu Glu Glu Glu Ser Ile Val Asn Thr Val Thr Ala
                165                 170                 175
Asn Ser Ser Lys Glu Gly Ala Trp Val Arg Asp Arg Leu Gly Pro Ala
                180                 185                 190
Pro Gly Gln Phe Phe Glu Asn Ser Gln Phe Pro Arg Gly Tyr Glu Asp
            195                 200                 205
Asn Tyr Phe Lys Glu Met Gly Phe Ser Pro Ser Ile Ser Ser Asp Glu
        210                 215                 220
Ile Val Asp Ala Val Lys Leu Val Thr His Ile Gly Pro Cys Val
225                 230                 235                 240
Leu Val Thr His Ser Ala Ser Gly Val Leu Gly Met Arg Val Ala Thr
                245                 250                 255
His Ala Lys Asn Val Arg Gly Ile Val Ala Tyr Glu Pro Ala Thr Ser
                260                 265                 270
Ile Phe Pro Lys Gly Lys Val Pro Glu Ile Pro Pro Leu Ala Asp Lys
            275                 280                 285
Lys Ser Gln Ile Phe Pro Pro Phe Glu Ile Gln Glu Ser Tyr Phe Lys
        290                 295                 300
Lys Leu Ala Lys Ile Pro Ile Gln Phe Val Phe Gly Asp Asn Ile Pro
305                 310                 315                 320
Lys Asn Pro Lys Ser Ala Tyr Trp Phe Leu Asp Trp Arg Val Thr
                325                 330                 335
Arg Tyr Ala His Ser Leu Ser Leu Glu Ala Ile Asn Lys Leu Gly Gly
                340                 345                 350
Gln Ala Ser Leu Leu Asp Leu Pro Thr Ala Gly Leu Arg Gly Asn Thr
            355                 360                 365
His Phe Pro Phe Thr Asp Arg Asn Asn Val Gln Val Ala Ser Leu Leu
        370                 375                 380
Ser Asp Phe Leu Gly Lys His Gly Leu Asp Gln Asn Glu Ser
385                 390                 395

<210> SEQ ID NO 8
<211> LENGTH: 1197
<212> TYPE: DNA
<213> ORGANISM: Artificial Sequence
<220> FEATURE:
<223> OTHER INFORMATION: the ALT01M1 nucleotide sequence encoding the
      amino acid sequence of the herbicide tolerant protein ALT01M1

<400> SEQUENCE: 8
atggaaaccg ataaaaaaac cggaacgtcc cgcagatcat tgtgaaggc tgctggaacc      60 ggcgcaatag gaatagcgac gctgccgctt tcgactgcaa ctgctttcgc ggaaactgac     120
aacgtggagc ttgcccaatc gaagcggaag gttgtccttg ctgaacaagg cagtttctac    180
atcgggggca gaacagtaac cgggcctgga aaattcgatc cgtcaaagcc ggtaattcca    240
tattccaacg aaggtgccac gttttatatc aatcaaatgt acgtaaactt tcaagctcct    300
gtgcgccctc gtgggctgcc tctagtcttt tggcatgggg gcggactaac cggccatatc    360
tgggaatcta ccccagacgg ccgccccgga tttcagaccc tctttgttca agatcggcat    420
acggtctaca cgattgatca gccagggcgc ggaaggggca atattcctac ctttaatggc    480
ccttttgggc agttggaaga agagtcgatt gttaacactg ttaccgcaaa ctccagtaaa    540
```

```
gaaggagcgt gggttagaga tcgactaggg cccgctcccg gccagttttt tgagaacagc      600
caattcccac gtggttatga agacaactac ttcaaggaga tggggttcag tccgtcgatc      660
tcatcagatg agatagtcga cgctgttgtt aaactagtaa ctcacatagg tccttgtgtt      720
ctggtgaccc attcggcttc cggagtactg ggcatgcgag tcgcgacaca cgccaagaac      780
gtgaggggga tcgttgctta tgagcctgcg acaagtatct ttcccaaagg aaaagtgcct      840
gagataccgc ctctcgccga taaaaagtcg caaattttcc cgccgttcga gatccaggag      900
tcttacttta agaagctcgc gaagataccc attcagtttg tcttcggaga taatatcccc      960
aagaacccta atccgccta ttggttcttg gactggtgga gagtcactcg ctacgctcac     1020
agcttgtcac tcgaggctat caataagctc ggtggtcaag cgtctctttt ggatttgccg     1080
actgcgggac ttcgcggcaa cacgcatttt ccattcaccg accggaataa cgtgcaggtc     1140
gcttctctgt tatctgattt cctcggaaag cacggcttag atcagaacga aagctga       1197
```

<210> SEQ ID NO 9
<211> LENGTH: 1197
<212> TYPE: DNA
<213> ORGANISM: Artificial Sequence
<220> FEATURE:
<223> OTHER INFORMATION: the ALT01M1-01 nucleotide sequence encoding the
      amino acid sequence corresponding to the herbicide tolerant
      protein ALT01M1 and based on the soybean codon usage bias

<400> SEQUENCE: 9

```
atggagactg ataagaaaac tggcacatct agaaggtcat tgttaaggc tgcaggaaca      60 ggtgccattg gaatcgctac ccttccattg tccaccgcca ctgctttcgc agagactgat     120
aacgtggaac tcgcccaatc taagagaaag gtggtgctgg ctgaacaagg gtcattttac     180 ataggggta ggactgttac tggtcctggc aagtttgatc catccaaacc tgtgataccc      240
tacagtaacg aaggagcaac attctatatt aaccaaatgt atgttaactt ccaggcccca     300
gtgagaccta ggggacttcc attggttttc tggcatggag gtggcttgac tggtcacatc     360
tgggagtcta cacctgacgg cagacccggg tttcaaaccc tcttcgttca ggataggcat     420
accgtgtaca ctattgacca acctgggaga ggaaggggta acatcccaac ttttaacgga     480
cctttcggac agttggagga agagagtatt gttaacactg tgacagccaa ttcttcaaag     540
gaaggtgcct gggtgagaga taggcttggc cctgctcccg ggcaattttt cgagaactct     600
cagtttccta gaggctatga agacaattac tttaaggaga tgggattcag cccatctata     660
tccagtgatg aaattgttga cgctgttgtg aaactcgtga cccatattgg tccttgtgtt     720
ctggtgactc actcagcatc cggcgttctt gggatgagag tggctacaca cgcaaagaat     780
gttaggggaa ttgtgccta tgaaccagct acctcaatct tccccaaggg aaaagttcca     840
gagataccac ctctcgctga taagaaaagc caaatcttc ccccattcga aatacaggag     900
tcttacttta agaaacttgc caagattcca atccaatttg ttttcggaga taacatcccc     960
aagaatccaa atcagcata ttggttcctg gactggtgga gagtgacaag atacgcacat     1020
agtctcagcc tggaggccat aaacaaattg gggggacaag cttcccttttt ggatcttcct     1080 actgcaggat tgagaggtaa tacacacttt ccccttcaccg ataggaacaa tgttcaggtg     1140
gcttctctcc tgtcagactt tctgggtaaa cacggtctgg atcaaaatga gagctga       1197
```

<210> SEQ ID NO 10
<211> LENGTH: 1197
<212> TYPE: DNA

<213> ORGANISM: Artificial Sequence
<220> FEATURE:
<223> OTHER INFORMATION: the ALT01M1-02 nucleotide sequence encoding the amino acid sequence corresponding to the herbicide tolerant protein ALT01M1 and based on the maize codon usage bias

<400> SEQUENCE: 10

```
atggagacag acaagaagac cggcacgtcc cgcaggagct cgtgaaggc tgctggcacc      60
ggggctatcg ggattgctac gctcccactg tcgacagcta ctgccttcgc ggagactgat    120
aacgtggagc tggcgcagag caagaggaag gtggttctgg ctgagcaggg gtcgttctac    180
attgggggc ggactgtgac cgggcccggc aagttcgacc catcgaagcc tgtcattccg     240
tactctaacg agggcgctac gttctacatc aaccagatgt acgtgaattt ccaggctccc    300
gtccgcccaa ggggcctccc actggtgttc tggcacggcg ggggcctgac aggccatatc    360
tgggagtcca ctccagatgg ccgcccaggg ttccagacac tcttcgttca ggacaggcac    420
acagtgtaca ctattgatca gccagggagg ggcaggggga acatccctac cttcaatggc    480
ccattcgggc agctggagga ggagtccatc gtgaacaccg tcacggcgaa ttccagcaag    540
gagggggctt gggtcaggga ccggctcggc ccggccccag gcagttcttc gagaactct     600
cagttccccc ggggctacga ggataattac ttcaaggaga tgggcttctc accatccatc    660
tcgtctgacg agattgtcga tgccgtggtc aagctcgtta cccacatcgg cccttgcgtt    720
ctggtgacgc atagcgcttc gggcgtcctc gggatgaggg ttgctacaca tgcgaagaac    780
gttcgcggca tcgtggctta cgagccggcc acttccattt tccccaaggg caaggtgcca    840
gagatcccac cactggccga caagaagtca cagatcttcc cacctttcga gattcaggag    900
tcctacttca gaagctcgc taagatcccc attcagttcg tgttcggcga caacattcct    960
aagaatccga gagcgcgta ctggttcctg gattggtggc gcgtcacgcg ctacgcgcac   1020
tctctctcac tggaggctat caacaagctc gggggccagg cctcgctcct ggacctcct    1080
accgctggcc tgaggggaa cacccattc ccgttcacgg atcggaacaa tgtccaggtt   1140
gcgtccctcc tgagcgattt cctcggcaag cacgggctgg atcagaatga gtcttga     1197
```

<210> SEQ ID NO 11
<211> LENGTH: 398
<212> TYPE: PRT
<213> ORGANISM: Artificial Sequence
<220> FEATURE:
<223> OTHER INFORMATION: the amino acid sequence of the herbicide tolerant protein ALT01M2

<400> SEQUENCE: 11

```
Met Glu Thr Asp Lys Lys Thr Gly Thr Ser Arg Arg Ser Phe Val Lys
1               5                   10                  15

Ala Ala Gly Thr Gly Ala Ile Gly Ile Ala Thr Leu Pro Leu Ser Thr
            20                  25                  30

Ala Thr Ala Phe Ala Glu Thr Asp Asn Val Glu Leu Ala Gln Ser Lys
        35                  40                  45

Arg Lys Val Val Leu Ala Glu Gln Gly Ser Phe Tyr Ile Gly Gly Arg
    50                  55                  60

Thr Val Thr Gly Pro Gly Lys Phe Asp Pro Ser Lys Pro Val Ile Pro
65                  70                  75                  80

Tyr Ser Asn Glu Gly Ala Thr Phe Tyr Ile Asn Gln Met Tyr Val Asn
                85                  90                  95

Phe Gln Ala Pro Val Arg Pro Arg Gly Leu Pro Leu Val Phe Trp His
            100                 105                 110
```

Gly Gly Gly Leu Thr Gly His Ile Trp Glu Ser Thr Pro Asp Gly Arg
            115                 120                 125

Pro Gly Phe Gln Thr Leu Phe Val Gln Asp Arg His Thr Val Tyr Thr
        130                 135                 140

Ile Asp Gln Pro Gly Arg Gly Arg Gly Asn Ile Pro Thr Phe Asn Gly
145                 150                 155                 160

Pro Phe Gly Gln Leu Glu Glu Glu Ser Ile Val Asn Thr Val Thr Gly
                165                 170                 175

Asn Val Ser Lys Glu Gly Ala Trp Val Arg Asp Arg Leu Gly Pro Ala
            180                 185                 190

Pro Gly Gln Phe Phe Glu Asn Ser Gln Phe Pro Arg Gly Tyr Glu Asp
        195                 200                 205

Asn Tyr Phe Lys Glu Met Gly Phe Ser Pro Ser Ile Ser Ser Asp Glu
    210                 215                 220

Ile Val Asp Ala Val Val Lys Leu Val Thr His Ile Gly Pro Cys Val
225                 230                 235                 240

Leu Val Thr His Ser Ala Ser Gly Val Leu Gly Met Arg Val Ala Thr
                245                 250                 255

His Ala Lys Asn Val Arg Gly Ile Val Ala Tyr Glu Pro Ala Thr Ser
            260                 265                 270

Ile Phe Pro Lys Gly Lys Val Pro Glu Ile Pro Pro Leu Ala Asp Lys
        275                 280                 285

Lys Ser Gln Ile Phe Pro Pro Phe Glu Ile Gln Glu Ser Tyr Phe Lys
    290                 295                 300

Lys Leu Ala Lys Ile Pro Ile Gln Phe Val Phe Gly Asp Asn Ile Pro
305                 310                 315                 320

Lys Asn Pro Lys Ser Ala Tyr Trp Phe Leu Asp Trp Trp Arg Val Thr
                325                 330                 335

Arg Tyr Ala His Ser Leu Ser Leu Glu Ala Ile Asn Lys Leu Gly Gly
            340                 345                 350

Gln Ala Ser Leu Leu Asp Leu Pro Thr Ala Gly Leu Arg Gly Asn Thr
        355                 360                 365

His Phe Pro Phe Thr Asp Arg Asn Asn Val Gln Val Ala Ser Leu Leu
    370                 375                 380

Ser Asp Phe Leu Gly Lys His Gly Leu Asp Gln Asn Glu Ser
385                 390                 395

<210> SEQ ID NO 12
<211> LENGTH: 1197
<212> TYPE: DNA
<213> ORGANISM: Artificial Sequence
<220> FEATURE:
<223> OTHER INFORMATION: the ALT01M2 nucleotide sequence encoding the
      amino acid sequence of the herbicide tolerant protein ALT01M2

<400> SEQUENCE: 12
atggaaaccg ataaaaaaac cggaacgtcc cgcagatcat ttgtgaaggc tgctggaacc      60
ggcgcaatag gaatagcgac gctgccgctt tcgactgcaa ctgctttcgc ggaaactgac     120
aacgtggagc ttgcccaatc gaagcggaag gttgtccttg ctaacaagg cagtttctac     180 atcggggca gaacagtaac cgggcctgga aaattcgatc cgtcaaagcc ggtaattcca     240
tattccaacg aaggtgccac gttttatatc aatcaaatgt acgtaaactt tcaagctcct     300
gtgcgccctc gtgggctgcc tctagtcttt tggcatgggg cggactaac cggccatatc     360 tgggaatcta ccccagacgg ccgccccgga tttcagaccc tctttgttca agatcggcat     420

```
acggtctaca cgattgatca gccagggcgc ggaaggggca atattcctac ctttaatggc      480 cctttgggc agttggaaga agagtcgatt gttaacactg ttaccggaaa cgtcagtaaa       540
gaaggagcgt gggttagaga tcgactaggg cccgctcccg gccagttttt tgagaacagc      600
caattcccac gtggttatga agacaactac ttcaaggaga tggggttcag tccgtcgatc      660
tcatcagatg agatagtcga cgctgttgtt aaactagtaa ctcacatagg tccttgtgtt     720
ctggtgaccc attcggcttc cggagtactg gcatgcgag tcgcgacaca cgccaagaac       780 gtgagggga tcgttgctta tgagcctgcg acaagtatct ttcccaaagg aaaagtgcct      840
gagataccgc ctctcgccga taaaaagtcg caaattttcc cgccgttcga gatccaggag      900
tcttacttta agaagctcgc gaagataccc attcagtttg tcttcggaga taatatcccc      960
aagaacccta atccgccta ttggttcttg gactggtgga gagtcactcg ctacgctcac     1020
agcttgtcac tcgaggctat caataagctc ggtggtcaag cgtctctttt ggatttgccg     1080
actgcgggac ttcgcggcaa cacgcatttt ccattcaccg accggaataa cgtgcaggtc     1140
gcttctctgt tatctgattt cctcggaaag cacggcttag atcagaacga aagctga       1197
```

<210> SEQ ID NO 13  
<211> LENGTH: 1197  
<212> TYPE: DNA  
<213> ORGANISM: Artificial Sequence  
<220> FEATURE:  
<223> OTHER INFORMATION: the ALT01M2-01 nucleotide sequence encoding the amino acid sequence corresponding to the herbicide tolerant protein ALT01M2 and based on the soybean codon usage bias

<400> SEQUENCE: 13

```
atggagactg ataagaaaac tggcacatct agaaggtcat tgttaaggc tgcaggaaca       60 ggtgccattg gaatcgctac ccttccattg tccaccgcca ctgctttcgc agagactgat      120
aacgtggaac tcgcccaatc taagagaaag gtggtgctgg ctgaacaagg tcattttac      180 ataggggta ggactgttac tggtcctggc aagtttgatc catccaaacc tgtgataccc       240
tacagtaacg aaggagcaac attctatatt aaccaaatgt atgttaactt ccaggcccca      300
gtgagaccta gggacttcc attggttttc tggcatggag gtggcttgac tggtcacatc      360
tgggagtcta cacctgacgg cagacccggg tttcaaaccc tcttcgttca ggataggcat     420
accgtgtaca ctattgacca acctgggaga ggaaggggta acatcccaac ttttaacgga     480
cctttcggac agttggagga agagagtatt gttaacactg tgacaggaaa tgtatcaaag     540
gaaggtgcct gggtgagaga taggcttggc cctgctcccg ggcaattttt cgagaactct     600
cagtttccta gaggctatga agacaattac tttaaggaga tgggattcag cccatctata     660
tccagtgatg aaattgttga cgctgttgtg aaactcgtga cccatattgg tccttgtgtt     720
ctggtgactc actcagcatc cggcgttctt gggatgagag tggctacaca cgcaaagaat     780 gttagggga ttgtgccta tgaaccagct acctcaatct cccccaaggg aaaagttcca      840
gagataccac ctctcgctga taagaaaagc caaatctttc ccccattcga aatacaggag     900
tcttacttta agaaacttgc caagattcca atccaatttg ttttcggaga taacatcccc      960
aagaatccaa atcagcata ttggttcctg gactggtgga gagtgacaag atacgcacat     1020
agtctcagcc tggaggccat aaacaaattg ggggacaag cttcccttttt ggatcttcct    1080 actgcaggat tgagaggtaa tacacacttt ccccttcaccg ataggaacaa tgttcaggtg    1140
gcttctctcc tgtcagactt tctgggtaaa cacggtctga tcaaaatga gagctga        1197
```

<210> SEQ ID NO 14
<211> LENGTH: 1197
<212> TYPE: DNA
<213> ORGANISM: Artificial Sequence
<220> FEATURE:
<223> OTHER INFORMATION: the ALT01M2-02 nucleotide sequence encoding the amino acid sequence corresponding to the herbicide tolerant protein ALT01M2 and based on the maize codon usage bias

<400> SEQUENCE: 14

```
atggagacag acaagaagac cggcacgtcc cgcaggagct cgtgaaggc tgctggcacc      60
ggggctatcg ggattgctac gctcccactg tcgacagcta ctgccttcgc ggagactgat     120
aacgtggagc tggcgcagag caagaggaag gtggttctgg ctgagcaggg gtcgttctac     180
attgggggc ggactgtgac cgggcccggc aagttcgacc catcgaagcc tgtcattccg      240
tactctaacg agggcgctac gttctacatc aaccagatgt acgtgaattt ccaggctccc     300
gtccgcccaa ggggcctccc actggtgttc tggcacggcg ggggcctgac aggccatatc     360
tgggagtcca ctccagatgg ccgcccaggg ttccagacac tcttcgttca ggacaggcac     420
acagtgtaca ctattgatca gccagggagg ggcaggggga acatccctac cttcaatggc     480
ccattcgggg agctggagga ggagtccatc gtgaacaccg tcacgggcaa gtgagcaag     540
gaggggcctt gggtcaggga ccggctcggc ccggcccag gcagttctt cgagaactct      600
cagttccccc ggggctacga ggataattac ttcaaggaga tgggcttctc accatccatc     660
tcgtctgacg agattgtcga tgccgtggtc aagctcgtta cccacatcgg cccttgcgtt     720
ctggtgacga tagcgcttc gggcgtcctc gggatgaggg ttgctacaca tgcgaagaac     780
gttcgcggca tcgtggctta cgagccggcc acttccattt tccccaaggg caaggtgcca     840
gagatcccac cactggccga caagaagtca cagatcttcc caccctttcga gattcaggag    900
tcctacttca agaagctcgc taagatcccc attcagttcg tgttcggcga caacattcct     960
aagaatccga gagcgcgta ctggttcctg gattggtggc gcgtcacgcg ctacgcgcac    1020
tctctcac tggaggctat caacaagctc gggggccagg cctcgctcct ggacctccct     1080
accgctggcc tgaggggga cacccatttc ccgttcacgg atcggaacaa tgtccaggtt    1140
gcgtccctcc tgagcgattt cctcggcaag cacgggctgg atcagaatga gtcttga      1197
```

<210> SEQ ID NO 15
<211> LENGTH: 398
<212> TYPE: PRT
<213> ORGANISM: Artificial Sequence
<220> FEATURE:
<223> OTHER INFORMATION: the amino acid sequence of the herbicide tolerant protein ALT01M3

<400> SEQUENCE: 15

Met Glu Thr Asp Lys Lys Thr Gly Thr Ser Arg Arg Ser Phe Val Lys
1               5                   10                  15

Ala Ala Gly Thr Gly Ala Ile Gly Ile Ala Thr Leu Pro Leu Ser Thr
            20                  25                  30

Ala Thr Ala Phe Ala Glu Thr Asp Asn Val Glu Leu Ala Gln Ser Lys
        35                  40                  45

Arg Lys Val Val Leu Ala Glu Gln Gly Ser Phe Tyr Ile Gly Gly Arg
    50                  55                  60

Thr Val Thr Gly Pro Gly Lys Phe Asp Pro Ser Lys Pro Val Ile Arg
65                  70                  75                  80

Ala Ser Asn Glu Gly Ala Thr Phe Tyr Ile Asn Gln Met Tyr Val Asn

```
                   85                  90                  95
Phe Gln Ala Pro Val Arg Pro Arg Gly Leu Pro Leu Val Phe Trp His
            100                 105                 110

Gly Gly Gly Leu Thr Gly His Ile Trp Glu Ser Thr Pro Asp Gly Arg
            115                 120                 125

Pro Gly Phe Gln Thr Leu Phe Val Gln Asp Arg His Thr Val Tyr Thr
            130                 135                 140

Ile Asp Gln Pro Gly Arg Gly Arg Gly Asn Ile Pro Thr Phe Asn Gly
145                 150                 155                 160

Pro Phe Gly Gln Leu Glu Glu Glu Ser Ile Val Asn Thr Val Thr Ala
                165                 170                 175

Asn Val Ser Lys Glu Arg Ala Trp Val Arg Asp Arg Leu Gly Pro Ala
            180                 185                 190

Pro Gly Gln Phe Phe Glu Asn Ser Gln Phe Pro Arg Gly Tyr Glu Asp
            195                 200                 205

Asn Tyr Phe Lys Glu Met Gly Phe Ser Pro Ser Ile Ser Ser Asp Glu
210                 215                 220

Ile Val Asp Ala Val Val Lys Leu Val Thr His Ile Gly Pro Cys Val
225                 230                 235                 240

Leu Val Thr His Ser Ala Ser Gly Val Leu Gly Met Arg Val Ala Thr
                245                 250                 255

His Ala Lys Asn Val Arg Gly Ile Val Ala Tyr Glu Pro Ala Thr Ser
            260                 265                 270

Ile Phe Pro Lys Gly Lys Val Pro Glu Ile Pro Pro Leu Ala Asp Lys
            275                 280                 285

Lys Ser Gln Ile Phe Pro Pro Phe Glu Ile Gln Glu Ser Tyr Phe Lys
            290                 295                 300

Lys Leu Ala Lys Ile Pro Ile Gln Phe Val Phe Gly Asp Asn Ile Pro
305                 310                 315                 320

Lys Asn Pro Lys Ser Ala Tyr Trp Phe Leu Asp Trp Trp Arg Val Thr
                325                 330                 335

Arg Tyr Ala His Ser Leu Ser Leu Glu Ala Ile Asn Lys Leu Gly Gly
            340                 345                 350

Gln Ala Ser Leu Leu Asp Leu Pro Thr Ala Gly Leu Arg Gly Asn Thr
            355                 360                 365

His Phe Pro Phe Thr Asp Arg Asn Asn Val Gln Val Ala Ser Leu Leu
            370                 375                 380

Ser Asp Phe Leu Gly Lys His Gly Leu Asp Gln Asn Glu Ser
385                 390                 395

<210> SEQ ID NO 16
<211> LENGTH: 1197
<212> TYPE: DNA
<213> ORGANISM: Artificial Sequence
<220> FEATURE:
<223> OTHER INFORMATION: the ALT01M3 nucleotide sequence encoding the
      amino acid sequence of the herbicide tolerant protein ALT01M3

<400> SEQUENCE: 16
atggaaaccg ataaaaaaac cggaacgtcc cgcagatcat ttgtgaaggc tgctggaacc      60
ggcgcaatag gaatagcgac gctgccgctt tcgactgcaa ctgctttcgc ggaaactgac     120
aacgtggagc ttgcccaatc gaagcggaag gttgtccttg ctgaacaagg cagtttctac     180
atcgggggca gaacagtaac cgggcctgga aaattcgatc cgtcaaagcc ggtaattcga     240
gcttccaacg aaggtgccac gttttatatc aatcaaatgt acgtaaactt tcaagctcct     300
```

```
gtgcgccctc gtgggctgcc tctagtcttt tggcatgggg gcggactaac cggccatatc      360
tgggaatcta ccccagacgg ccgccccgga tttcagaccc tctttgttca agatcggcat      420
acggtctaca cgattgatca gccagggcgc ggaaggggca atattcctac ctttaatggc      480
ccttttgggc agttggaaga agagtcgatt gttaacactg ttaccgcaaa cgtcagtaaa      540
gaaagagcgt gggttagaga tcgactaggg cccgctcccg gccagttttt tgagaacagc      600
caattcccac gtggttatga agacaactac ttcaaggaga tggggttcag tccgtcgatc      660
tcatcagatg agatagtcga cgctgttgtt aaactagtaa ctcacatagg tccttgtgtt      720
ctggtgaccc attcggcttc cggagtactg ggcatgcgag tcgcgacaca cgccaagaac      780
gtgaggggga tcgttgctta tgagcctgcg acaagtatct ttcccaaagg aaaagtgcct      840
gagataccgc ctctcgccga taaaaagtcg caaattttcc cgccgttcga gatccaggag      900
tcttacttta agaagctcgc gaagatcccc attcagtttg tcttcggaga taatatcccc      960
aagaacccta atccgcccta ttggttcttg gactggtgga gagtcactcg ctacgctcac     1020
agcttgtcac tcgaggctat caataagctc ggtggtcaag cgtctctttt ggatttgccg     1080
actgcgggac ttcgcggcaa cacgcatttt ccattcaccg accggaataa cgtgcaggtc     1140
gcttctctgt tatctgattt cctcggaaag cacggcttag atcagaacga aagctga       1197
```

<210> SEQ ID NO 17  
<211> LENGTH: 1197  
<212> TYPE: DNA  
<213> ORGANISM: Artificial Sequence  
<220> FEATURE:  
<223> OTHER INFORMATION: the ALT01M3-01 nucleotide sequence encoding the amino acid sequence corresponding to the herbicide tolerant protein ALT01M3 and based on the soybean codon usage bias

<400> SEQUENCE: 17

```
atggagactg ataagaaaac tggcacatct agaaggtcat tgttaaggc tgcaggaaca       60 ggtgccattg gaatcgctac ccttccattg tccaccgcca ctgctttcgc agagactgat      120
aacgtggaac tcgcccaatc taagagaaag gtggtgctgg ctgaacaagg gtcattttac      180 ataggggta ggactgttac tggtcctggc aagtttgatc catccaaacc tgtgatacga      240
gccagtaacg aaggagcaac attctatatt aaccaaatgt atgttaactt ccaggcccca      300
gtgagaccta ggggacttcc attggttttc tggcatggag gtggcttgac tggtcacatc      360
tgggagtcta cacctgacgg cagacccggg tttcaaaccc tcttcgttca ggataggcat      420
accgtgtaca ctattgacca acctgggaga ggaaggggta acatcccaac ttttaacgga      480
cctttcggac agttggagga agagagtatt gttaacactg tgacagccaa tgtatcaaag      540
gaacgagcct gggtgagaga taggcttggc cctgctcccg ggcaattttt cgagaactct      600
cagtttccta gaggctatga agacaattac tttaaggaga tgggattcag cccatctata      660
tccagtgatg aaattgttga cgctgttgtg aaactcgtga cccatattgg tccttgtgtt      720
ctggtgactc actcagcatc cggcgttctt gggatgagag tggctacaca cgcaaagaat      780
gttaggggaa ttgtggccta tgaaccagct acctcaatct cccccaaggg aaaagttcca      840
gagataccac ctctcgctga taagaaaagc caaatctttc ccccattcga atacaggag       900 tcttacttta agaaacttgc caagattcca atccaatttg ttttcggaga taacatcccc      960
aagaatccaa atcagcata ttggttcctg gactggtgga gagtgacaag atacgcacat     1020
agtctcagcc tggaggccat aaacaaattg gggggacaag cttccctttt ggatcttcct     1080
```
actgcaggat tgagaggtaa tacacacttt cccttcaccg ataggaacaa tgttcaggtg    1140
gcttctctcc tgtcagactt tctgggtaaa cacggtctgg atcaaaatga gagctga    1197

<210> SEQ ID NO 18
<211> LENGTH: 1197
<212> TYPE: DNA
<213> ORGANISM: Artificial Sequence
<220> FEATURE:
<223> OTHER INFORMATION: the ALT01M3-02 nucleotide sequence encoding the
      amino acid sequence corresponding to the herbicide tolerant
      protein ALT01M3 and based on the maize codon usage bias

<400> SEQUENCE: 18
atggagacag acaagaagac cggcacgtcc cgcaggagct tcgtgaaggc tgctggcacc      60
ggggctatcg ggattgctac gctcccactg tcgacagcta ctgccttcgc ggagactgat     120
aacgtggagc tggcgcagag caagaggaag gtggttctgg ctgagcaggg gtcgttctac     180 attgggggc ggactgtgac cgggcccggc aagttcgacc catcgaagcc tgtcattcgg     240
gcgtctaacg agggcgctac gttctacatc aaccagatgt acgtgaattt ccaggctccc     300
gtccgcccaa ggggcctccc actggtgttc tggcacggcg ggggcctgac aggccatatc     360
tgggagtcca ctccagatgg ccgcccaggg ttccagacac tcttcgttca ggacaggcac     420
acagtgtaca ctattgatca gccagggagg ggcaggggga acatccctac cttcaatggc     480
ccattcgggc agctggagga ggagtccatc gtgaacaccg tcacggcgaa gtgagcaag     540 gagcgggctt gggtcaggga ccggctcggc ccggcccag gcagttctt cgagaactct     600 cagttccccc ggggctacga ggataattac ttcaaggaga tgggcttctc accatccatc     660
tcgtctgacg agattgtcga tgccgtggtc aagctcgtta cccacatcgg cccttgcgtt     720
ctggtgacga atagcgcttc gggcgtcctc gggatgaggg ttgctacaca tgcgaagaac     780
gttcgcggca tcgtggctta cgagccggcc acttccattt tccccaaggg caaggtgcca     840
gagatcccac cactggccga caagaagtca cagatcttcc caccttctcga gattcaggag     900 tcctacttca agaagctcgc taagatcccc attcagttcg tgttcggcga caacattcct     960
aagaatccga gagcgcgta ctggttcctg gattggtggc gcgtcacgcg ctacgcgcac    1020
tctctctcac tggaggctat caacaagctc gggggccagg cctcgctcct ggacctccct    1080
accgctggcc tgaggggaa cacccatttc ccgttcacgg atcggaacaa tgtccaggtt    1140
gcgtccctcc tgagcgattt cctcggcaag cacgggctgg atcagaatga gtcttga      1197

<210> SEQ ID NO 19
<211> LENGTH: 369
<212> TYPE: PRT
<213> ORGANISM: Artificial Sequence
<220> FEATURE:
<223> OTHER INFORMATION: the amino acid sequence of ALT02

<400> SEQUENCE: 19

Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
            20                  25                  30

Pro Gly Lys Phe Asp Pro Ser Lys Pro Val Ile Pro Tyr Ser Asn Glu
        35                  40                  45

Gly Ala Thr Phe Tyr Ile Asn Gln Met Tyr Val Asn Phe Gln Ala Pro
    50                  55                  60

Val Arg Pro Arg Gly Leu Pro Leu Val Phe Trp His Gly Gly Gly Leu

```
                    65              70              75              80
        Thr Gly His Ile Trp Glu Ser Thr Pro Asp Gly Arg Pro Gly Phe Gln
                            85              90              95
        Thr Leu Phe Val Gln Asp Arg His Thr Val Tyr Thr Ile Asp Gln Pro
                        100             105             110
        Gly Arg Gly Arg Gly Asn Ile Pro Thr Phe Asn Gly Pro Phe Gly Gln
                        115             120             125
        Leu Glu Glu Ser Ile Val Asn Thr Val Thr Gly Asn Ser Ser Lys
                        130             135             140
        Glu Gly Ala Trp Val Arg Asp Arg Leu Gly Pro Ala Pro Gly Gln Phe
        145                 150             155             160
        Phe Glu Asn Ser Gln Phe Pro Arg Gly Tyr Glu Asp Asn Tyr Phe Lys
                            165             170             175
        Glu Met Gly Phe Ser Pro Ser Ile Ser Ser Asp Glu Ile Val Asp Ala
                        180             185             190
        Val Val Lys Leu Val Thr His Ile Gly Pro Cys Val Leu Val Thr His
                        195             200             205
        Ser Ala Ser Gly Val Leu Gly Met Arg Val Ala Thr His Ala Lys Asn
                        210             215             220
        Val Arg Gly Ile Val Ala Tyr Glu Pro Ala Thr Ser Ile Phe Pro Lys
        225                 230             235             240
        Gly Lys Val Pro Glu Ile Pro Pro Leu Ala Asp Lys Lys Ser Gln Ile
                            245             250             255
        Phe Pro Pro Phe Glu Ile Gln Glu Ser Tyr Phe Lys Lys Leu Ala Lys
                        260             265             270
        Ile Pro Ile Gln Phe Val Phe Gly Asp Asn Ile Pro Lys Asn Pro Lys
                        275             280             285
        Ser Ala Tyr Trp Phe Leu Asp Trp Trp Arg Val Thr Arg Tyr Ala His
                    290             295             300
        Ser Leu Ser Leu Glu Ala Ile Asn Lys Leu Gly Gly Gln Ala Ser Leu
        305                 310             315             320
        Leu Asp Leu Pro Thr Ala Gly Leu Arg Gly Asn Thr His Phe Pro Phe
                            325             330             335
        Thr Asp Arg Asn Asn Val Gln Val Ala Ser Leu Leu Ser Asp Phe Leu
                        340             345             350
        Gly Lys His Gly Leu Asp Gln Asn Glu Ser Lys Leu Ala Ala Ala Leu
                    355             360             365
        Glu

<210> SEQ ID NO 20
<211> LENGTH: 1110
<212> TYPE: DNA
<213> ORGANISM: Artificial Sequence
<220> FEATURE:
<223> OTHER INFORMATION: the ALT02 nucleotide sequence encoding the
      amino acid sequence of ALT02

<400> SEQUENCE: 20
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc catattccaa cgaaggtgcc acgttttata tcaatcaaat gtacgtaaac     180
tttcaagctc ctgtgcgccc tcgtgggctg cctctagtct tttggcatgg ggcggactga     240
accggccata tctgggaatc taccccagac ggccgccccg gatttcagac cctctttgtt     300
```

```
caagatcggc atacggtcta cacgattgat cagccagggc gcggaagggg caatattcct    360
acctttaatg gcccttttgg gcagttggaa gaagagtcga ttgttaacac tgttaccgga    420
aactccagta aagaaggagc gtgggttaga gatcgactag ggcccgctcc cggccagttt    480
tttgagaaca gccaattccc acgtggttat gaagacaact acttcaagga gatggggttc    540
agtccgtcga tctcatcaga tgagatagtc gacgctgttg ttaaactagt aactcacata    600
ggtccttgtg ttctggtgac ccattcggct tccggagtac tgggcatgcg agtcgcgaca    660
cacgccaaga acgtgagggg gatcgttgct tatgagcctg cgacaagtat ctttcccaaa    720
ggaaaagtgc ctgagatacc gcctctcgcc gataaaaagt cgcaaatttt cccgccgttc    780
gagatccagg agtcttactt taagaagctc gcgaagatac ccattcagtt tgtcttcgga    840
gataatatcc ccaagaaccc taaatccgcc tattggttct ggactggtg gagagtcact    900
cgctacgctc acagcttgtc actcgaggct atcaataagc tcggtggtca agcgtctctt    960
ttggatttgc cgactgcggg acttcgcggc aacacgcatt tccattcac cgaccggaat   1020
aacgtgcagg tcgcttctct gttatctgat ttcctcggaa agcacggctt agatcagaac   1080
gaaagcaaac ttgctgctgc tcttgagtga                                    1110
```

<210> SEQ ID NO 21
<211> LENGTH: 1110
<212> TYPE: DNA
<213> ORGANISM: Artificial Sequence
<220> FEATURE:
<223> OTHER INFORMATION: the ALT02-01 nucleotide sequence encoding the amino acid sequence corresponding to the ALT02 and based on the soybean codon usage bias

<400> SEQUENCE: 21

```
atggagactg ataacgtgga actcgcccaa tctaagagaa aggtggtgct ggctgaacaa     60
gggtcatttt acatagggg taggactgtt actggtcctg gcaagtttga tccatccaaa    120
cctgtgatac cctacagtaa cgaaggagca acattctata ttaaccaaat gtatgttaac    180
ttccaggccc cagtgagacc taggggactt ccattggttt tctggcatgg aggtggcttg    240
actggtcaca tctgggagtc tacacctgac ggcagacccg gtttcaaac cctcttcgtt    300
caggataggc ataccgtgta cactattgac caacctggga gaggaagggg taacatccca    360
acttttaacg gaccttccgg acagttggag gaagagtgta ttgttaacac tgtgacagga    420
aattcttcaa aggaaggtgc ctgggtgaga gataggcttg gccctgctcc cgggcaattt    480
ttcgagaact ctcagttttcc tagaggctat gaagacaatt acttaaggaa gatgggattc    540
agcccatcta tatccagtga tgaaattgtt gacgctgttg tgaaactcgt gacccatatt    600
ggtccttgtg ttctggtgac tcactcagca tccggcgttc ttgggatgag agtggctaca    660
cacgcaaaga atgttagggg aattgtggcc tatgaaccag ctacctcaat cttccccaag    720
ggaaaagttc cagagatacc acctctcgct gataagaaaa gccaaatctt ccccccattc    780
gaaatacagg agtcttactt taagaaactt gccaagattc aatccaatt tgttttcgga    840
gataacatcc ccaagaatcc aaaatcagca tattggttcc tggactggtg gagagtgaca    900
agatacgcac atagtctcag cctggaggcc ataaacaaat ggggggaca gcttccctt    960
ttggatcttc ctactgcagg attgagaggt aatacacact ttcccttcac cgataggaac   1020
aatgttcagg tggcttctct cctgtcagac tttctgggta acacggtct ggatcaaaat   1080
gagagcaaac tcgccgccgc cctggaatga                                   1110
```

<210> SEQ ID NO 22
<211> LENGTH: 1110
<212> TYPE: DNA
<213> ORGANISM: Artificial Sequence
<220> FEATURE:
<223> OTHER INFORMATION: the ALT02-02 nucleotide sequence encoding the
      amino acid sequence corresponding to the herbicide tolerant
      protein ALT02 and based on the maize codon usage bias

<400> SEQUENCE: 22

```
atggagactg ataacgtgga gctggcgcag agcaagagga aggtggttct ggctgagcag    60
gggtcgttct acattggggg gcggactgtg accgggcccg gcaagttcga cccatcgaag   120
cctgtcattc gtactctaa cgagggcgct acgttctaca tcaaccagat gtacgtgaat   180
ttccaggctc ccgtccgccc aaggggcctc ccactggtgt tctggcacgg cgggggcctg   240
acaggccata tctgggagtc cactccagat ggccgcccag ggttccagac actcttcgtt   300
caggacaggc acacagtgta cactattgat cagccaggga ggggcagggg gaacatccct   360
accttcaatg cccattcgg gcagctggag gaggagtcca tcgtgaacac cgtcacgggc   420
aattccagca aggaggggggc ttgggtcagg accggctcg gcccggcccc agggcagttc   480
ttcgagaact ctcagttccc ccggggctac gaggataatt acttcaagga gatgggcttc   540
tcaccatcca tctcgtctga cgagattgtc gatgccgtgg tcaagctcgt tacccacatc   600
ggcccttgcg ttctggtgac gcatagcgct tcgggcgtcc tcgggatgag ggttgctaca   660
catgcgaaga acgttcgcgg catcgtggct tacgagccgg ccacttccat tttccccaag   720
ggcaaggtgc cagagatccc accactggcc gacaagaagt cacagatctt cccaccttc    780
gagattcagg agtcctactt caagaagctc gctaagatcc ccattcagtt cgtgttcggc   840
gacaacattc ctaagaatcc gaagagcgcg tactggttcc tggattggtg gcgcgtcacg   900
cgctacgcgc actctctc actggaggct atcaacaagc tcggggccca ggcctcgctc   960
ctggacctcc ctaccgctgg cctgagggggg aacaccatt tcccgttcac ggatcggaac   1020
aatgtccagg ttgcgtccct cctgagcgat ttcctcggca agcacgggct ggatcagaat  1080
gagtctaagc tcgctgcggc gctggagtga                                   1110
```

<210> SEQ ID NO 23
<211> LENGTH: 369
<212> TYPE: PRT
<213> ORGANISM: Artificial Sequence
<220> FEATURE:
<223> OTHER INFORMATION: the amino acid sequence of ALT02M1

<400> SEQUENCE: 23

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
            20                  25                  30

Pro Gly Lys Phe Asp Pro Ser Lys Pro Val Ile Pro Tyr Ser Asn Glu
        35                  40                  45

Gly Ala Thr Phe Tyr Ile Asn Gln Met Tyr Val Asn Phe Gln Ala Pro
    50                  55                  60

Val Arg Pro Arg Gly Leu Pro Leu Val Phe Trp His Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110
```

```
Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Ala Asn Ser Ser Lys
130                 135                 140

Glu Gly Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
        195                 200                 205

Ser Ala Ser Gly Val Leu Gly Met Arg Val Ala Thr His Ala Lys Asn
    210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
                245                 250                 255

Phe Pro Pro Phe Glu Ile Gln Ser Tyr Phe Lys Lys Leu Ala Lys
            260                 265                 270

Ile Pro Ile Gln Phe Val Phe Gly Asp Asn Ile Pro Lys Asn Pro Lys
        275                 280                 285

Ser Ala Tyr Trp Phe Leu Asp Trp Trp Arg Val Thr Arg Tyr Ala His
    290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
            340                 345                 350

Gly Lys His Gly Leu Asp Gln Asn Glu Ser Lys Leu Ala Ala Ala Leu
        355                 360                 365

Glu
```

<210> SEQ ID NO 24
<211> LENGTH: 1110
<212> TYPE: DNA
<213> ORGANISM: Artificial Sequence
<220> FEATURE:
<223> OTHER INFORMATION: the ALT02M1 nucleotide sequence encoding the
      amino acid sequence of the herbicide tolerant protein ALT02M1

<400> SEQUENCE: 24

```
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc catattccaa cgaaggtgcc acgttttata tcaatcaaat gtacgtaaac     180
tttcaagctc ctgtgcgccc tcgtgggctg cctctagtct tttggcatgg gggcggacta     240
accggccata tctgggaatc taccccagac ggccgcccg gatttcagac cctctttgtt     300
caagatcggc atacggtcta cacgattgat cagccagggc gcggaagggg caatattcct     360
acctttaatg gcccttttgg gcagttggaa gaagagtcga ttgttaacac tgttaccgca     420
aactccagta agaaggagc gtgggttaga gatcgactag gcccgctcc cggccagttt     480 tttgagaaca gccaattccc acgtggttat gaagacaact acttcaagga gatggggttc     540
```

```
agtccgtcga tctcatcaga tgagatagtc gacgctgttg ttaaactagt aactcacata    600
ggtccttgtg ttctggtgac ccattcggct tccggagtac tgggcatgcg agtcgcgaca    660
cacgccaaga acgtgagggg gatcgttgct tatgagcctg cgacaagtat ctttcccaaa    720
ggaaaagtgc ctgagatacc gcctctcgcc gataaaaagt cgcaaatttt cccgccgttc    780
gagatccagg agtcttactt taagaagctc gcgaagatac ccattcagtt tgtcttcgga    840
gataatatcc ccaagaaccc taaatccgcc tattggttct ggactggtg gagagtcact      900 cgctacgctc acagcttgtc actcgaggct atcaataagc tcggtggtca agcgtctctt    960
ttggatttgc cgactgcggg acttcgcggc aacacgcatt ttccattcac cgaccggaat    1020
aacgtgcagg tcgcttctct gttatctgat ttcctcggaa agcacggctt agatcagaac    1080
gaaagcaaac ttgctgctgc tcttgagtga                                     1110
```

<210> SEQ ID NO 25
<211> LENGTH: 1110
<212> TYPE: DNA
<213> ORGANISM: Artificial Sequence
<220> FEATURE:
<223> OTHER INFORMATION: the ALT02M1-01 nucleotide sequence encoding the amino acid sequence corresponding to the herbicide tolerant protein ALT02M1 and based on the soybean codon usage bias

<400> SEQUENCE: 25

```
atggagactg ataacgtgga actcgcccaa tctaagagaa aggtggtgct ggctgaacaa     60
gggtcatttt acatagggggg taggactgtt actggtcctg gcaagtttga tccatccaaa    120
cctgtgatac cctacagtaa cgaaggagca acattctata ttaaccaaat gtatgttaac    180
ttccaggccc cagtgagacc taggggactt ccattggttt tctggcatgg aggtggcttg    240
actggtcaca tctgggagtc tacacctgac ggcagacccg gtttcaaac cctcttcgtt      300 caggataggc ataccgtgta cactattgac caacctggga gaggaagggg taacatccca    360
acttttaacg gaccttccgg acagttggag gaagagagta ttgttaacac tgtgacagcc    420
aattcttcaa aggaaggtgc ctgggtgaga gataggcttg gccctgctcc cgggcaattt    480
ttcgagaact ctcagtttcc tagaggctat gaagacaatt actttaagga gatgggattc    540
agcccatcta tatccagtga tgaaattgtt gacgctgttg tgaaactcgt gacccatatt    600
ggtccttgtg ttctggtgac tcactcagca tccggcgttc ttgggatgag agtggctaca    660
cacgcaaaga atgttagggg aattgtggcc tatgaaccag ctacctcaat cttcccaag     720 ggaaaagttc cagagatacc acctctcgct gataagaaaa gccaaatctt tccccattc     780 gaaatacagg agtcttactt taagaaactt gccagattc caatccaatt tgtttcgga      840 gataacatcc ccaagaatcc aaaatcagca tattggttcc tggactggtg gagagtgaca    900
agatacgcac atagtctcag cctggaggcc ataaacaaat gggggggaca agcttccctt    960
ttggatcttc ctactgcagg attgagaggt aatacacact ttcccttcac cgataggaac    1020
aatgttcagg tggcttctct cctgtcagac tttctgggta aacacggtct ggatcaaaat    1080
gagagcaaac tcgccgccgc cctggaatga                                     1110
```

<210> SEQ ID NO 26
<211> LENGTH: 1110
<212> TYPE: DNA
<213> ORGANISM: Artificial Sequence
<220> FEATURE:
<223> OTHER INFORMATION: the ALT02M1-02 nucleotide sequence encoding the amino acid sequence corresponding to the herbicide tolerant protein ALT02M1 and based on the maize codon usage bias

<400> SEQUENCE: 26

```
atggagactg ataacgtgga gctggcgcag agcaagagga aggtggttct ggctgagcag    60
gggtcgttct acattggggg gcggactgtg accgggcccg gcaagttcga cccatcgaag   120
cctgtcattc cgtactctaa cgagggcgct acgttctaca tcaaccagat gtacgtgaat   180
ttccaggctc ccgtccgccc aaggggcctc ccactggtgt tctggcacgg cgggggcctg   240
acaggccata tctgggagtc cactccagat ggccgcccag ggttccagac actcttcgtt   300
caggacaggc acacagtgta cactattgat cagccaggga ggggcagggg gaacatccct   360
accttcaatg gcccattcgg gcagctggag gaggagtcca tcgtgaacac cgtcacggcg   420
aattccagca aggagggggc ttgggtcagg accggctcg gcccggcccc agggcagttc    480
ttcgagaact ctcagttccc ccggggctac gaggataatt acttcaagga gatgggcttc   540
tcaccatcca tctcgtctga cgagattgtc gatgccgtgg tcaagctcgt tacccacatc   600
ggcccttgcg ttctggtgac gcatagcgct tcgggcgtcc tcgggatgag ggttgctaca   660
catgcgaaga acgttcgcgg catcgtggct tacgagccgg ccacttccat tttccccaag   720
ggcaaggtgc cagagatccc accactggcc gacaagaagt cacagatctt cccacctttc   780
gagattcagg agtcctactt caagaagctc gctaagatcc ccattcagtt cgtgttcggc   840
gacaacattc taagaatcc gaagagcgcg tactggttcc tggattggtg cgcgtcacg    900
cgctacgcgc actctctctc actggaggct atcaacaagc tcgggggcca ggcctcgctc   960
ctggacctcc ctaccgctgg cctgaggggg aacacccatt tccgttcac ggatcggaac   1020
aatgtccagg ttgcgtccct cctgagcgat ttcctcggca agcacgggct ggatcagaat   1080
gagtctaagc tcgctgcggc gctggagtga                                    1110
```

<210> SEQ ID NO 27
<211> LENGTH: 369
<212> TYPE: PRT
<213> ORGANISM: Artificial Sequence
<220> FEATURE:
<223> OTHER INFORMATION: the amino acid sequence of the ALT02M2

<400> SEQUENCE: 27

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
                20                  25                  30

Pro Gly Lys Phe Asp Pro Ser Lys Pro Val Ile Pro Tyr Ser Asn Glu
            35                  40                  45

Gly Ala Thr Phe Tyr Ile Asn Gln Met Tyr Val Asn Phe Gln Ala Pro
        50                  55                  60

Val Arg Pro Arg Gly Leu Pro Leu Val Phe Trp His Gly Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Gly Asn Val Ser Lys
    130                 135                 140
```

Glu Gly Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
        195                 200                 205

Ser Ala Ser Gly Val Leu Gly Met Arg Val Ala Thr His Ala Lys Asn
    210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
                245                 250                 255

Phe Pro Pro Phe Glu Ile Gln Glu Ser Tyr Phe Lys Lys Leu Ala Lys
            260                 265                 270

Ile Pro Ile Gln Phe Val Phe Gly Asp Asn Ile Pro Lys Asn Pro Lys
        275                 280                 285

Ser Ala Tyr Trp Phe Leu Asp Trp Trp Arg Val Thr Arg Tyr Ala His
290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
            340                 345                 350

Gly Lys His Gly Leu Asp Gln Asn Glu Ser Lys Leu Ala Ala Ala Leu
        355                 360                 365

Glu

<210> SEQ ID NO 28
<211> LENGTH: 1110
<212> TYPE: DNA
<213> ORGANISM: Artificial Sequence
<220> FEATURE:
<223> OTHER INFORMATION: the ALT02M2 nucleotide sequence encoding the
      amino acid sequence of the herbicide tolerant protein ALT02M2

<400> SEQUENCE: 28
atggaaactg acaacgtgga gcttgcccaa tcgaagcgga aggttgtcct tgctgaacaa      60
ggcagtttct catcgggggg cagaacagta accgggcctg aaaattcga tccgtcaaag     120 ccggtaattc catattccaa cgaaggtgcc acgttttata tcaatcaaat gtacgtaaac     180
tttcaagctc ctgtgcgccc tcgtgggctg cctctagtct tttggcatgg ggcggacta     240 accggccata tctgggaatc taccccagac ggccgccccg gatttcagac cctctttgtt     300
caagatcggc atacggtcta cacgattgat cagccagggc gcggaagggg caatattcct     360
acctttaatg gccctttttgg gcagttggaa gaagagtcga ttgttaacac tgttaccgga     420
aacgtcagta agaaggagc gtgggttaga gatcgactag ggcccgctcc cggccagttt     480
tttgagaaca gccaattccc acgtggttat gaagacaact acttcaagga gatgggtttc     540
agtccgtcga tctcatcaga tgagatagtc gacgctgttg ttaaactagt aactcacata     600
ggtccttgtg ttctggtgac ccattcggct tccggagtac tgggcatgcg agtcgcgaca     660
cacgccaaga acgtgagggg gatcgttgct tatgagcctg cgacaagtat ctttcccaaa     720

```
ggaaaagtgc ctgagatacc gcctctcgcc gataaaaagt cgcaaatttt cccgccgttc    780
gagatccagg agtcttactt taagaagctc gcgaagatac ccattcagtt tgtcttcgga    840
gataatatcc ccaagaaccc taaatccgcc tattggttct tggactggtg agagtcact     900 cgctacgctc acagcttgtc actcgaggct atcaataagc tcggtggtca agcgtctctt    960
ttggatttgc cgactgcggg acttcgcggc aacacgcatt ttccattcac cgaccggaat   1020
aacgtgcagg tcgcttctct gttatctgat ttcctcggaa agcacggctt agatcagaac   1080
gaaagcaaac ttgctgctgc tcttgagtga                                    1110
```

<210> SEQ ID NO 29
<211> LENGTH: 1110
<212> TYPE: DNA
<213> ORGANISM: Artificial Sequence
<220> FEATURE:
<223> OTHER INFORMATION: the ALT02M2-01 nucleotide sequence encoding the amino acid sequence corresponding to the herbicide tolerant protein ALT02M2 and based on the soybean codon usage bias

<400> SEQUENCE: 29

```
atggagactg ataacgtgga actcgcccaa tctaagagaa aggtggtgct ggctgaacaa     60
gggtcatttt acataggggg taggactgtt actggtcctg caagtttga tccatccaaa    120 cctgtgatac cctacagtaa cgaaggagca acattctata ttaaccaaat gtatgttaac    180
ttccaggccc cagtgagacc taggggactt ccattggttt ctggcatgg aggtggcttg    240 actggtcaca tctgggagtc tacacctgac ggcagacccg ggtttcaaac cctcttcgtt    300 caggatagge ataccgtgta cactattgac caacctggga gaggaagggg taacatccca    360 actttaacg accttccgg acagttggag aagagagta ttgttaacac tgtgacagga       420
aatgtatcaa aggaaggtgc ctgggtgaga gataggcttg gccctgctcc cgggcaattt    480
ttcgagaact ctcagtttcc tagaggctat gaagacaatt actttaagga gatgggattc    540
agcccatcta tatccagtga tgaaattgtt gacgctgttg tgaaactcgt gacccatatt    600
ggtccttgtg ttctggtgac tcactcagca tccggcgttc ttgggatgag agtggctaca    660
cacgcaaaga atgttagggg aattgtggcc tatgaaccag ctacctcaat cttccccaag    720
ggaaaagttc cagagatacc acctctcgct gataagaaaa gccaaatctt tccccccattc    780 gaaatacagg agtcttactt taagaaactt gccaagattc caatccaatt tgttttcgga    840
gataacatcc ccaagaatcc aaaatcagca tattggttcc tggactggtg agagtgaca     900 agatacgcac atagtctcag cctggaggcc ataaacaaat tgggggggaca agcttccctt    960 ttggatcttc ctactgcagg attgagaggt aatacacact ttcccttcac cgataggaac   1020
aatgttcagg tggcttctct cctgtcagac tttctgggta aacacggtct ggatcaaaat   1080
gagagcaaac tcgccgccgc cctggaatga                                    1110
```

<210> SEQ ID NO 30
<211> LENGTH: 1110
<212> TYPE: DNA
<213> ORGANISM: Artificial Sequence
<220> FEATURE:
<223> OTHER INFORMATION: the ALT02M2-02 nucleotide sequence encoding the amino acid sequence corresponding to the herbicide tolerant protein ALT02M2 and based on the maize codon usage bias

<400> SEQUENCE: 30

```
atggagactg ataacgtgga gctggcgcag agcaaggagga aggtggttct ggctgagcag     60
gggtcgttct acattggggg gcggactgtg accgggcccg gcaagttcga cccatcgaag   120
```

```
cctgtcattc cgtactctaa cgagggcgct acgttctaca tcaaccagat gtacgtgaat    180
ttccaggctc ccgtccgccc aaggggcctc ccactggtgt tctggcacgg cggggggcctg   240
acaggccata tctggagtc cactccagat ggccgcccag ggttccagac actcttcgtt    300
caggacaggc acacagtgta cactattgat cagccaggga ggggcagggg gaacatccct   360
accttcaatg cccattcgg gcagctggag gaggagtcca tcgtgaacac cgtcacgggc    420
aatgtgagca aggaggggc ttgggtcagg gaccggctcg gcccggcccc agggcagttc    480
ttcgagaact ctcagttccc ccggggctac gaggataatt acttcaagga tgggcttc    540
tcaccatcca tctcgtctga cgagattgtc gatgccgtgg tcaagctcgt tacccacatc   600
ggcccttgcg ttctggtgac gcatagcgct tcgggcgtcc tcgggatgag ggttgctaca    660
catgcgaaga acgttcgcgg catcgtggct tacgagccgg ccacttccat tttccccaag    720
ggcaaggtgc cagagatccc accactggcc gacaagaagt cacagatctt cccacctttc    780
gagattcagg agtcctactt caagaagctc gctaagatcc ccattcagtt cgtgttcggc    840
gacaacattc ctaagaatcc gaagagcgcg tactggttcc tggattggtg gcgcgtcacg    900
cgctacgcgc actctctctc actggaggct atcaacaagc tcggggggcca ggcctcgctc    960
ctggacctcc ctaccgctgg cctgaggggg aacacccatt tcccgttcac ggatcggaac   1020
aatgtccagg ttgcgtccct cctgagcgat ttcctcggca agcacgggct ggatcagaat   1080
gagtctaagc tcgctgcggc gctggagtga                                    1110

<210> SEQ ID NO 31
<211> LENGTH: 369
<212> TYPE: PRT
<213> ORGANISM: Artificial Sequence
<220> FEATURE:
<223> OTHER INFORMATION: the amino acid sequence of the ALT02M3

<400> SEQUENCE: 31

Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
                20                  25                  30

Pro Gly Lys Phe Asp Pro Ser Lys Pro Val Ile Arg Ala Ser Asn Glu
            35                  40                  45

Gly Ala Thr Phe Tyr Ile Asn Gln Met Tyr Val Asn Phe Gln Ala Pro
        50                  55                  60

Val Arg Pro Arg Gly Leu Pro Leu Val Phe Trp His Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Ala Asn Val Ser Lys
    130                 135                 140

Glu Arg Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
```

```
            180                 185                 190
Val Val Lys Leu Val Thr His Ile Gly Pro Cys Val Leu Val Thr His
            195                 200                 205

Ser Ala Ser Gly Val Leu Gly Met Arg Val Ala Thr His Ala Lys Asn
            210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
                245                 250                 255

Phe Pro Pro Phe Glu Ile Gln Glu Ser Tyr Phe Lys Lys Leu Ala Lys
            260                 265                 270

Ile Pro Ile Gln Phe Val Phe Gly Asp Asn Ile Pro Lys Asn Pro Lys
            275                 280                 285

Ser Ala Tyr Trp Phe Leu Asp Trp Trp Arg Val Thr Arg Tyr Ala His
            290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
                340                 345                 350

Gly Lys His Gly Leu Asp Gln Asn Glu Ser Lys Leu Ala Ala Ala Leu
            355                 360                 365

Glu
```

<210> SEQ ID NO 32
<211> LENGTH: 1110
<212> TYPE: DNA
<213> ORGANISM: Artificial Sequence
<220> FEATURE:
<223> OTHER INFORMATION: the ALT02M3 nucleotide sequence encoding the
      amino acid sequence of the herbicide tolerant protein ALT02M3

<400> SEQUENCE: 32

```
atggaaactg acaacgtgga gcttgcccaa tcgaagcgga aggttgtcct tgctgaacaa      60
ggcagtttct acatcggggg cagaacagta accgggcctg gaaaattcga tccgtcaaag     120
ccggtaattc gagcttccaa cgaaggtgcc acgttttata tcaatcaaat gtacgtaaac     180
tttcaagctc ctgtgcgccc tcgtgggctg cctctagtct tttggcatgg gggcggacta     240
accggccata tctgggaatc taccccagac ggccgcccg gatttcagac cctctttgtt     300
caagatcggc atacggtcta cacgattgat cagccagggc gcggaagggg caatattcct     360
acctttaatg ccccttttgg gcagttggaa gaagagtcga ttgttaacac tgttaccgca     420
aacgtcagta agaaagagc gtgggttaga gatcgactag ggcccgctcc cggccagttt      480
tttgagaaca gccaattccc acgtggttat gaagacaact acttcaagga gatgggttc      540
agtccgtcga tctcatcaga tgagatagtc gacgctgttg ttaaactagt aactcacata     600
ggtccttgtg ttctggtgac ccattcggct tccggagtac tgggcatgcg agtcgcgaca     660
cacgccaaga acgtgagggg gatcgttgct tatgagcctg cgacaagtat ctttcccaaa     720
ggaaaagtgc ctgagatacc gcctctcgcc gataaaaagt cgcaaatttt cccgccgttc     780
gagatccagg agtcttactt taagaagctc gcgaagatac ccattcagtt tgtcttcgga     840
gataatatcc ccaagaaccc taatccgcc tattggttct ggactggtg gagagtcact      900
cgctacgctc acagcttgtc actcgaggct atcaataagc tcggtggtca agcgtctctt     960
```

-continued

```
ttggatttgc cgactgcggg acttcgcggc aacacgcatt ttccattcac cgaccggaat    1020
aacgtgcagg tcgcttctct gttatctgat ttcctcggaa agcacggctt agatcagaac    1080
gaaagcaaac ttgctgctgc tcttgagtga                                     1110
```

<210> SEQ ID NO 33
<211> LENGTH: 1110
<212> TYPE: DNA
<213> ORGANISM: Artificial Sequence
<220> FEATURE:
<223> OTHER INFORMATION: the ALT02M3-01 nucleotide sequence encoding the
      amino acid sequence corresponding to the herbicide tolerant
      protein ALT02M3 and based on the soybean codon usage bias

<400> SEQUENCE: 33

```
atggagactg ataacgtgga actcgcccaa tctaagagaa aggtggtgct ggctgaacaa     60
gggtcatttt acatagggggg taggactgtt actggtcctg gcaagtttga tccatccaaa   120
cctgtgatac gagccagtaa cgaaggagca acattctata ttaaccaaat gtatgttaac   180
ttccaggccc cagtgagacc taggggactt ccattggttt tctggcatgg aggtggcttg   240
actggtcaca tctgggagtc tacacctgac ggcagacccg gtttcaaac cctcttcgtt    300 caggataggc ataccgtgta cactattgac caacctggga gaggaagggg taacatccca   360
acttttaacg gacctttcgg acagttggag gaagagagta ttgttaacac tgtgacagcc   420
aatgtatcaa aggaacgagc ctgggtgaga gataggcttg gccctgctcc cgggcaattt    480
ttcgagaact ctcagtttcc tagaggctat gaagacaatt actttaagga gatgggattc   540
agcccatcta tatccagtga tgaaattgtt gacgctgttg tgaaactcgt gacccatatt   600
ggtccttgtg ttctggtgac tcactcagca tccggcgttc ttgggatgag agtggctaca   660
cacgcaaaga atgttagggg aattgtggcc tatgaaccag ctacctcaat cttccccaag   720
ggaaaagttc cagagatacc acctctcgct gataagaaaa gccaaatctt tccccattc    780 gaaatacagg agtcttactt taagaaactt gccaagattc aatccaatt tgttttcgga   840 gataacatcc ccaagaatcc aaaatcagca tattggttcc tggactggtg gagagtgaca   900
agatacgcac atagtctcag cctggaggcc ataaacaaat tgggggggaca agcttccctt    960 ttggatcttc ctactgcagg attgagaggt aatacacact tccccttcac cgataggaac   1020
aatgttcagg tggcttctct cctgtcagac tttctgggta acacggtct ggatcaaaat   1080 gagagcaaac tcgccgccgc cctggaatga                                    1110
```

<210> SEQ ID NO 34
<211> LENGTH: 1110
<212> TYPE: DNA
<213> ORGANISM: Artificial Sequence
<220> FEATURE:
<223> OTHER INFORMATION: the ALT02M3-02 nucleotide sequence encoding the
      amino acid sequence corresponding to the herbicide tolerant
      protein ALT02M3 and based on the maize codon usage bias

<400> SEQUENCE: 34

```
atggagactg ataacgtgga gctggcgcag agcaagagga aggtggttct ggctgagcag     60
gggtcgttct acattggggg gcggactgtg accgggcccg gcaagttcga cccatcgaag   120
cctgtcattc gggcgtctaa cgagggcgct acgttctaca tcaaccagat gtacgtgaat   180
ttccaggctc ccgtccgccc aaggggcctc ccactggtgt tctggcacgg cggggggcctg   240 acaggccata tctgggagtc cactccagat ggccgcccag ggttccagac actcttcgtt   300
```

```
caggacaggc acacagtgta cactattgat cagccaggga ggggcagggg gaacatccct    360
accttcaatg gcccattcgg gcagctggag gaggagtcca tcgtgaacac cgtcacggcg    420
aatgtgagca aggagcgggc ttgggtcagg gaccggctcg gcccggcccc agggcagttc    480
ttcgagaact ctcagttccc ccggggctac gaggataatt acttcaagga gatgggcttc    540
tcaccatcca tctcgtctga cgagattgtc gatgccgtgg tcaagctcgt tacccacatc    600
ggcccttgcg ttctggtgac gcatagcgct tcgggcgtcc tcgggatgag ggttgctaca    660
catgcgaaga acgttcgcgg catcgtggct tacgagccgg ccacttccat tttccccaag    720
ggcaaggtgc cagagatccc accactggcc gacaagaagt cacagatctt cccacctttc    780
gagattcagg agtcctactt caagaagctc gctaagatcc ccattcagtt cgtgttcggc    840
gacaacattc ctaagaatcc gaagagcgcg tactggttcc tggattggtg gcgcgtcacg    900
cgctacgcgc actctctctc actggaggct atcaacaagc tcgggggcca ggcctcgctc    960
ctggacctcc ctaccgctgg cctgaggggg aacacccatt tcccgttcac ggatcggaac   1020
aatgtccagg ttgcgtccct cctgagcgat ttcctcggca agcacgggct ggatcagaat   1080
gagtctaagc tcgctgcggc gctggagtga                                    1110
```

<210> SEQ ID NO 35
<211> LENGTH: 362
<212> TYPE: PRT
<213> ORGANISM: Artificial Sequence
<220> FEATURE:
<223> OTHER INFORMATION: the amino acid sequence of ALT03

<400> SEQUENCE: 35

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
            20                  25                  30

Pro Gly Lys Phe Asp Pro Ser Lys Pro Val Ile Pro Tyr Ser Asn Glu
        35                  40                  45

Gly Ala Thr Phe Tyr Ile Asn Gln Met Tyr Val Asn Phe Gln Ala Pro
    50                  55                  60

Val Arg Pro Arg Gly Leu Pro Leu Val Phe Trp His Gly Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Gly Asn Ser Ser Lys
    130                 135                 140

Glu Gly Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
        195                 200                 205

Ser Ala Ser Gly Val Leu Gly Met Arg Val Ala Thr His Ala Lys Asn
    210                 215                 220
```

```
Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
            245                 250                 255

Phe Pro Pro Phe Glu Ile Gln Glu Ser Tyr Phe Lys Lys Leu Ala Lys
        260                 265                 270

Ile Pro Ile Gln Phe Val Phe Gly Asp Asn Ile Pro Lys Asn Pro Lys
    275                 280                 285

Ser Ala Tyr Trp Phe Leu Asp Trp Trp Arg Val Thr Arg Tyr Ala His
290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
                340                 345                 350

Gly Lys His Gly Leu Asp Gln Asn Glu Ser
            355                 360

<210> SEQ ID NO 36
<211> LENGTH: 1089
<212> TYPE: DNA
<213> ORGANISM: Artificial Sequence
<220> FEATURE:
<223> OTHER INFORMATION: the ALT03 nucleotide sequence encoding the
      amino acid sequence of ALT03

<400> SEQUENCE: 36
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc catattccaa cgaaggtgcc acgtttttata tcaatcaaat gtacgtaaac     180
tttcaagctc ctgtgcgccc tcgtgggctg cctctagtct tttggcatgg gggcggacta     240
accggccata tctgggaatc taccccagac ggccgccccg gatttcagac cctcttttgtt    300 caagatcggc atacggtcta cacgattgat cagccagggc gcggaagggg caatattcct     360
acctttaatg gccctttttgg gcagttggaa gaagagtcga ttgttaacac tgttaccgga    420
aactccagta agaaggagc gtgggttaga gatcgactag gcccgctcc cggccagttt      480 tttgagaaca gccaattccc acgtggttat gaagacaact acttcaagga tgggggttc     540 agtccgtcga tctcatcaga tgagatagtc gacgctgttg ttaaactagt aactcacata    600
ggtccttgtg ttctggtgac ccattcggct tccggagtac tgggcatgcg agtcgcgaca    660
cacgccaaga acgtgagggg gatcgttgct tatgagcctg cgacaagtat ctttcccaaa    720
ggaaaagtgc ctgagatacc gcctctcgcc gataaaaagt cgcaaatttt cccgccgttc    780
gagatccagg agtcttactt taagaagctc gcgaagatac ccattcagtt tgtcttcgga    840
gataatatcc ccaagaaccc taaatccgcc tattggttct ggactggtg gagagtcact     900 cgctacgctc acagcttgtc actcgaggct atcaataagc tcggtggtca agcgtctctt    960
ttggatttgc cgactgcggg acttcgcggc aacacgcatt tccattcac cgaccggaat    1020 aacgtgcagg tcgcttctct gttatctgat ttcctcggaa agcacggctt agatcagaac    1080
gaaagctga                                                            1089

<210> SEQ ID NO 37
```

```
<211> LENGTH: 1089
<212> TYPE: DNA
<213> ORGANISM: Artificial Sequence
<220> FEATURE:
<223> OTHER INFORMATION: the ALT03-01 nucleotide sequence encoding the
      amino acid sequence corresponding to the ALT03 and based on the
      soybean codon usage bias

<400> SEQUENCE: 37
atggagactg ataacgtgga actcgcccaa tctaagagaa aggtggtgct ggctgaacaa     60
gggtcatttt acatagggggg taggactgtt actggtcctg gcaagtttga tccatccaaa    120
cctgtgatac cctacagtaa cgaaggagca acattctata ttaaccaaat gtatgttaac    180
ttccaggccc cagtgagacc tagggggactt ccattggttt tctggcatgg aggtggcttg   240
actggtcaca tctgggagtc tacacctgac ggcagacccg ggtttcaaac cctcttcgtt    300
caggatagcc ataccgtgta cactattgac caacctggga gaggaaggggg taacatccca   360 acttttaacg gacctttcgg acagttggag aagagagta ttgttaacac tgtgacagga    420
aattcttcaa aggaaggtgc ctgggtgaga gataggcttg ccctgctcc cgggcaatttt   480 ttcgagaact ctcagtttcc tagaggctat gaagacaatt actttaagga tgggattc      540 agcccatcta tatccagtga tgaaattgtt gacgctgttg tgaaactcgt gacccatatt    600
ggtccttgtg ttctggtgac tcactcagca tccggcgttc ttgggatgag agtggctaca    660
cacgcaaaga atgttagggg aattgtggcc tatgaaccag ctacctcaat cttccccaag    720
ggaaaagttc cagagatacc acctctcgct gataagaaaa gccaaatctt tcccccattc    780
gaaatacagg agtcttactt taagaaactt gccaagattc caatccaatt tgttttcgga    840
gataacatcc ccaagaatcc aaaatcagca tattggttcc tggactggtg gagagtgaca    900
agatacgcac atagtctcag cctggaggcc ataaacaaat gggggggaca agcttccctt    960
ttggatcttc ctactgcagg attgagaggt aatacacact ttcccttcac cgataggaac   1020
aatgttcagg tggcttctct cctgtcagac tttctgggta acacggtct ggatcaaaat    1080 gagagctga                                                            1089

<210> SEQ ID NO 38
<211> LENGTH: 1089
<212> TYPE: DNA
<213> ORGANISM: Artificial Sequence
<220> FEATURE:
<223> OTHER INFORMATION: the ALT03-02 nucleotide sequence encoding the
      amino acid sequence corresponding to the herbicide tolerant
      protein ALT03 and based on the maize codon usage bias

<400> SEQUENCE: 38
atggagactg ataacgtgga gctggcgcag agcaagagga aggtggttct ggctgagcag     60
gggtcgttct acattggggg gcggactgtg accgggcccg gcaagttcga cccatcgaag    120
cctgtcattc cgtactctaa cgagggcgct acgttctaca tcaaccagat gtacgtgaat    180
ttccaggctc ccgtccgccc aagggggcctc ccactggtgt ctggcacgg cggggggcctg  240 acaggccata tctgggagtc cactccagat ggccgcccag ggttccagac actcttcgtt    300
caggacaggc acacagtgta cactattgat cagccaggga ggggcagggg gaacatcccct   360 accttcaatg gcccattcgg gcagctggag gaggagtcca tcgtgaacac cgtcacgggc    420
aattccagca aggaggggggc ttgggtcagg gaccggctcg gcccggcccc agggcagttc    480
ttcgagaact ctcagtttcc ccgggggctac gaggataatt acttcaagga tgggcttc     540 tcaccatcca tctcgtctga cgagattgtc gatgccgtgg tcaagctcgt tacccacatc    600
```

-continued

```
ggcccttgcg ttctggtgac gcatagcgct tcgggcgtcc tcgggatgag ggttgctaca    660
catgcgaaga acgttcgcgg catcgtggct tacgagccgg ccacttccat tttccccaag    720
ggcaaggtgc cagagatccc accactggcc gacaagaagt cacagatctt cccacctttc    780
gagattcagg agtcctactt caagaagctc gctaagatcc ccattcagtt cgtgttcggc    840
gacaacattc ctaagaatcc gaagagcgcg tactggttcc tggattggtg gcgcgtcacg    900
cgctacgcgc actctctctc actggaggct atcaacaagc tcgggggcca ggcctcgctc    960
ctggacctcc ctaccgctgg cctgaggggg aacacccatt tcccgttcac ggatcggaac   1020
aatgtccagg ttgcgtccct cctgagcgat ttcctcggca agcacgggct ggatcagaat   1080
gagtcttga                                                            1089
```

<210> SEQ ID NO 39
<211> LENGTH: 362
<212> TYPE: PRT
<213> ORGANISM: Artificial Sequence
<220> FEATURE:
<223> OTHER INFORMATION: the amino acid sequence of the ALT03M1

<400> SEQUENCE: 39

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
                20                  25                  30

Pro Gly Lys Phe Asp Pro Ser Lys Pro Val Ile Pro Tyr Ser Asn Glu
            35                  40                  45

Gly Ala Thr Phe Tyr Ile Asn Gln Met Tyr Val Asn Phe Gln Ala Pro
        50                  55                  60

Val Arg Pro Arg Gly Leu Pro Leu Val Phe Trp His Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Ala Asn Ser Ser Lys
    130                 135                 140

Glu Gly Ala Trp Val Arg Asp Arg Leu Gly Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
        195                 200                 205

Ser Ala Ser Gly Val Leu Gly Met Arg Val Ala Thr His Ala Lys Asn
    210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Ser Gln Ile
                245                 250                 255

Phe Pro Pro Phe Glu Ile Gln Glu Ser Tyr Phe Lys Lys Leu Ala Lys
            260                 265                 270
```

```
Ile Pro Ile Gln Phe Val Phe Gly Asp Asn Ile Pro Lys Asn Pro Lys
            275                 280                 285

Ser Ala Tyr Trp Phe Leu Asp Trp Trp Arg Val Thr Arg Tyr Ala His
    290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
                340                 345                 350

Gly Lys His Gly Leu Asp Gln Asn Glu Ser
                355                 360

<210> SEQ ID NO 40
<211> LENGTH: 1089
<212> TYPE: DNA
<213> ORGANISM: Artificial Sequence
<220> FEATURE:
<223> OTHER INFORMATION: the ALT03M1 nucleotide sequence  encoding the
      amino acid sequence of the herbicide tolerant protein ALT03M1

<400> SEQUENCE: 40
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc catattccaa cgaaggtgcc acgttttata tcaatcaaat gtacgtaaac     180
tttcaagctc ctgtgcgccc tcgtgggctg cctctagtct tttggcatgg ggcggacta     240 accggccata tctgggaatc taccccagac ggccgccccg gatttcagac cctctttgtt     300
caagatcggc atacggtcta cacgattgat cagccagggc gcggaagggg caatattcct     360
acctttaatg gccctttgg gcagttggaa gaagagtcga ttgttaacac tgttaccgca     420
aactccagta agaaggagc gtgggttaga gatcgactag gccccgctcc cggccagttt     480
tttgagaaca gccaattccc acgtggttat gaagacaact acttcaagga gatggggttc     540
agtccgtcga tctcatcaga tgagatagtc gacgctgttg ttaaactagt aactcacata     600
ggtccttgtg ttctggtgac ccattcggct tccggagtac tgggcatgcg agtcgcgaca     660
cacgccaaga acgtgagggg gatcgttgct tatgagcctg cgacaagtat ctttcccaaa     720
ggaaaagtgc ctgagatacc gcctctcgcc gataaaaagt cgcaaatttt cccgccgttc     780
gagatccagg agtcttactt taagaagctc gcgaagatac ccattcagtt tgtcttcgga     840
gataatatcc ccaagaaccc taaatccgcc tattggttct tggactggtg gagagtcact     900
cgctacgctc acagcttgtc actcgaggct atcaataagc tcggtggtca agcgtctctt     960
ttggatttgc cgactgcggg acttcgcggc aacacgcatt ttccattcac cgaccggaat    1020
aacgtgcagg tcgcttctct gttatctgat ttcctcggaa agcacggctt agatcagaac    1080
gaaagctga                                                             1089

<210> SEQ ID NO 41
<211> LENGTH: 1089
<212> TYPE: DNA
<213> ORGANISM: Artificial Sequence
<220> FEATURE:
<223> OTHER INFORMATION: the ALT03M1-01 nucleotide sequence encoding the
      amino acid sequence corresponding to the herbicide tolerant
      protein ALT03M1 and based on the soybean codon usage bias

<400> SEQUENCE: 41
```

```
atggagactg ataacgtgga actcgcccaa tctaagagaa aggtggtgct ggctgaacaa    60
gggtcatttt acatagggggg taggactgtt actggtcctg gcaagtttga tccatccaaa   120
cctgtgatac cctacagtaa cgaaggagca acattctata ttaaccaaat gtatgttaac   180
ttccaggccc cagtgagacc taggggactt ccattggttt tctggcatgg aggtggcttg   240
actggtcaca tctgggagtc tacacctgac ggcagacccg gtttcaaaac cctcttcgtt   300
caggataggc ataccgtgta cactattgac caacctggga gaggaagggg taacatccca   360
acttttaacg gaccttcgg acagttggag gaagagagta ttgttaacac tgtgacagcc   420
aattcttcaa aggaaggtgc ctgggtgaga gataggcttg gccctgctcc cgggcaattt   480
ttcgagaact ctcagtttcc tagaggctat gaagacaatt actttaagga gatgggattc   540
agcccatcta tatccagtga tgaaattgtt gacgctgttg tgaaactcgt gacccatatt   600
ggtccttgtg ttctggtgac tcactcagca tccggcgttc ttgggatgag agtggctaca   660
cacgcaaaga atgttagggg aattgtggcc tatgaaccag ctacctcaat cttccccaag   720
ggaaaagttc cagagatacc acctctcgct gataagaaaa gccaaatctt tcccccattc   780
gaaatacagg agtcttactt taagaaactt gccaagattc caatccaatt tgttttcgga   840
gataacatcc ccaagaatcc aaaatcagca tattggttcc tggactggtg gagagtgaca   900
agatacgcac atagtctcag cctggaggcc ataaacaaat tgggggggaca agcttccctt   960
ttggatcttc ctactgcagg attgagaggt aatacacact ttcccttcac cgataggaac  1020
aatgttcagg tggcttctct cctgtcagac tttctgggta acacggtct ggatcaaaat  1080
gagagctga                                                          1089
```

<210> SEQ ID NO 42
<211> LENGTH: 1089
<212> TYPE: DNA
<213> ORGANISM: Artificial Sequence
<220> FEATURE:
<223> OTHER INFORMATION: the ALT03M1-02 nucleotide sequence encoding the amino acid sequence corresponding to the herbicide tolerant protein ALT03M1 and based on the maize codon usage bias

<400> SEQUENCE: 42

```
atggagactg ataacgtgga actcgcccaa tctaagagaa aggtggtgct ggctgaacaa    60
gggtcatttt acatagggggg taggactgtt actggtcctg gcaagtttga tccatccaaa   120
cctgtgatac cctacagtaa cgaaggagca acattctata ttaaccaaat gtatgttaac   180
ttccaggccc cagtgagacc taggggactt ccattggttt tctggcatgg aggtggcttg   240
actggtcaca tctgggagtc tacacctgac ggcagacccg gtttcaaaac cctcttcgtt   300
caggataggc ataccgtgta cactattgac caacctggga gaggaagggg taacatccca   360
acttttaacg gaccttcgg acagttggag gaagagagta ttgttaacac tgtgacagcc   420
aattcttcaa aggaaggtgc ctgggtgaga gataggcttg gccctgctcc cgggcaattt   480
ttcgagaact ctcagtttcc tagaggctat gaagacaatt actttaagga gatgggattc   540
agcccatcta tatccagtga tgaaattgtt gacgctgttg tgaaactcgt gacccatatt   600
ggtccttgtg ttctggtgac tcactcagca tccggcgttc ttgggatgag agtggctaca   660
cacgcaaaga atgttagggg aattgtggcc tatgaaccag ctacctcaat cttccccaag   720
ggaaaagttc cagagatacc acctctcgct gataagaaaa gccaaatctt tcccccattc   780
gaaatacagg agtcttactt taagaaactt gccaagattc caatccaatt tgttttcgga   840
```

```
gataacatcc ccaagaatcc aaaatcagca tattggttcc tggactggtg gagagtgaca    900
agatacgcac atagtctcag cctggaggcc ataaacaaat tgggggggaca agcttccctt    960 ttggatcttc ctactgcagg attgagaggt aatacacact ttcccttcac cgataggaac   1020
aatgttcagg tggcttctct cctgtcagac tttctgggta aacacggtct ggatcaaaat   1080
gagagctga                                                            1089
```

<210> SEQ ID NO 43
<211> LENGTH: 362
<212> TYPE: PRT
<213> ORGANISM: Artificial Sequence
<220> FEATURE:
<223> OTHER INFORMATION: the amino acid sequence of the ALT03M2

<400> SEQUENCE: 43

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
            20                  25                  30

Pro Gly Lys Phe Asp Pro Ser Lys Pro Val Ile Pro Tyr Ser Asn Glu
        35                  40                  45

Gly Ala Thr Phe Tyr Ile Asn Gln Met Tyr Val Asn Phe Gln Ala Pro
    50                  55                  60

Val Arg Pro Arg Gly Leu Pro Leu Val Phe Trp His Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
        115                 120                 125

Leu Glu Glu Glu Ser Ile Val Asn Thr Val Thr Gly Asn Val Ser Lys
    130                 135                 140

Glu Gly Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
        195                 200                 205

Ser Ala Ser Gly Val Leu Gly Met Arg Val Ala Thr His Ala Lys Asn
    210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
                245                 250                 255

Phe Pro Pro Phe Glu Ile Gln Glu Ser Tyr Phe Lys Lys Leu Ala Lys
            260                 265                 270

Ile Pro Ile Gln Phe Val Phe Gly Asp Asn Ile Pro Lys Asn Pro Lys
        275                 280                 285

Ser Ala Tyr Trp Phe Leu Asp Trp Trp Arg Val Thr Arg Tyr Ala His
    290                 295                 300

Ser Leu Ser Leu Glu Ala Ile Asn Lys Leu Gly Gly Gln Ala Ser Leu
305                 310                 315                 320
```

Leu Asp Leu Pro Thr Ala Gly Leu Arg Gly Asn Thr His Phe Pro Phe
            325                 330                 335

Thr Asp Arg Asn Asn Val Gln Val Ala Ser Leu Leu Ser Asp Phe Leu
            340                 345                 350

Gly Lys His Gly Leu Asp Gln Asn Glu Ser
            355                 360

<210> SEQ ID NO 44
<211> LENGTH: 1089
<212> TYPE: DNA
<213> ORGANISM: Artificial Sequence
<220> FEATURE:
<223> OTHER INFORMATION: the ALT03M2 nucleotide sequence encoding the
      amino acid sequence of the herbicide tolerant protein ALT03M2

<400> SEQUENCE: 44

```
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc catattccaa cgaaggtgcc acgttttata tcaatcaaat gtacgtaaac     180
tttcaagctc ctgtgcgccc tcgtgggctg cctctagtct tttggcatgg gggcggacta     240
accggccata tctgggaatc taccccagac ggccgccccg gatttcagac cctctttgtt     300
caagatcggc atacggtcta cacgattgat cagccagggc gcggaagggg caatattcct     360
acctttaatg gccctttttgg gcagttggaa gaagagtcga ttgttaacac tgttaccgga     420
aacgtcagta agaaggagc gtgggttaga gatcgactag gcccgctcc cggccagttt     480 tttgagaaca gccaattccc acgtggttat gaagacaact acttcaagga gatgggggttc     540 agtccgtcga tctcatcaga tgagatagtc gacgctgttg ttaaactagt aactcacata     600
ggtccttgtg ttctggtgac ccattcggct tccggagtac tgggcatgcg agtcgcgaca     660
cacgccaaga acgtgagggg gatcgttgct tatgagcctg cgacaagtat ctttcccaaa     720
ggaaaagtgc ctgagatacc gcctctcgcc gataaaaagt cgcaaatttt cccgccgttc     780
gagatccagg agtcttactt taagaagctc gcgaagatac ccattcagtt tgtcttcgga     840
gataatatcc caagaaccc taaatccgcc tattggttct tggactggtg agagtcact     900 cgctacgctc acagcttgtc actcgaggct atcaataagc tcggtggtca agcgtctctt     960
ttggatttgc cgactgcggg acttcgcggc aacacgcatt ttccattcac cgaccggaat    1020
aacgtgcagg tcgcttctct gttatctgat ttcctcggaa agcacggctt agatcagaac    1080
gaaagctga                                                            1089
```

<210> SEQ ID NO 45
<211> LENGTH: 1089
<212> TYPE: DNA
<213> ORGANISM: Artificial Sequence
<220> FEATURE:
<223> OTHER INFORMATION: the ALT03M2-01 nucleotide sequence encoding the
      amino acid sequence corresponding to the herbicide tolerant
      protein ALT03M2 and based on the soybean codon usage bias

<400> SEQUENCE: 45

```
atggagactg ataacgtgga actcgcccaa tctaagagaa aggtggtgct ggctgaacaa      60
gggtcatttt acatagggg taggactgtt actggtcctg gcaagtttga tccatccaaa     120
cctgtgatac cctacagtaa cgaaggagca acattctata ttaaccaaat gtatgttaac     180
ttccaggccc cagtgagacc taggggactt ccattggttt tctggcatgg aggtggcttg     240
```

```
actggtcaca tctgggagtc tacacctgac ggcagacccg ggtttcaaac cctcttcgtt      300
caggataggc ataccgtgta cactattgac caacctggga gaggaagggg taacatccca      360
acttttaacg gacctttcgg acagttggag gaagagagta ttgttaacac tgtgacagga      420
aatgtatcaa aggaaggtgc ctgggtgaga gataggcttg gccctgctcc cgggcaattt      480
ttcgagaact ctcagtttcc tagaggctat gaagacaatt actttaagga gatgggattc      540
agcccatcta tatccagtga tgaaattgtt gacgctgttg tgaaactcgt gacccatatt      600
ggtccttgtg ttctggtgac tcactcagca tccggcgttc ttgggatgag agtggctaca      660
cacgcaaaga atgttagggg aattgtggcc tatgaaccag ctacctcaat cttccccaag      720
ggaaaagttc cagagatacc acctctcgct gataagaaaa gccaaatctt tcccccattc      780
gaaatacagg agtcttactt taagaaactt gccaagattc caatccaatt tgttttcgga      840
gataacatcc ccaagaatcc aaaatcagca tattggttcc tggactggtg gagagtgaca      900
agatacgcac atagtctcag cctggaggcc ataaacaaat tggggggaca agcttccctt      960
ttggatcttc ctactgcagg attgagaggt aatacacact ttcccttcac cgataggaac     1020
aatgttcagg tggcttctct cctgtcagac tttctgggta aacacggtct ggatcaaaat     1080
gagagctga                                                             1089

<210> SEQ ID NO 46
<211> LENGTH: 1089
<212> TYPE: DNA
<213> ORGANISM: Artificial Sequence
<220> FEATURE:
<223> OTHER INFORMATION: the ALT03M2-02 nucleotide sequence encoding the
      amino acid sequence corresponding to the herbicide tolerant
      protein ALT03M2 and based on the maize codon usage bias

<400> SEQUENCE: 46
atggagactg ataacgtgga gctggcgcag agcaagagga aggtggttct ggctgagcag       60
gggtcgttct acattggggg gcggactgtg accgggcccg gcaagttcga cccatcgaag      120
cctgtcattc cgtactctaa cgagggcgct acgttctaca tcaaccagat gtacgtgaat      180
ttccaggctc ccgtccgccc aaggggcctc ccactggtgt ctggcacgg cggggggcctg      240 acaggccata tctgggagtc cactccagat ggccgcccag ggttccagac actcttcgtt      300
caggacaggc acacagtgta cactattgat cagccaggga ggggcagggg gaacatccct      360
accttcaatg gcccattcgg gcagctggag gaggagtcca tcgtgaacac cgtcacgggc      420
aatgtgagca aggaggggggc ttgggtcagg gaccggctcg gcccggcccc agggcagttc      480
ttcgagaact ctcagttccc ccggggctac gaggataatt acttcaagga gatgggcttc      540
tcaccatcca tctcgtctga cgagattgtc gatgccgtgg tcaagctcgt tacccacatc      600
ggcccttgcg ttctggtgac gcatagcgct tcgggcgtcc tcgggatgag ggttgctaca      660
catgcgaaga acgttcgcgg catcgtggct tacgagccgg ccacttccat ttttccccaag      720 ggcaaggtgc cagagatccc accactggcc gacaagaagt cacagatctt cccaccttc      780 gagattcagg agtcctactt caagaagctc gctaagatcc ccattcagtt cgtgttcggc      840
gacaacattc ctaagaatcc gaagagcgcg tactggttcc tggattggtg gcgcgtcacg      900
cgctacgcgc actctctctc actggaggct atcaacaagc tcgggggcca ggcctcgctc      960
ctggacctcc ctaccgctgg cctgaggggg aacacccatt tccgttcac ggatcggaac      1020 aatgtccagg ttgcgtccct cctgagcgat ttcctcggca agcacgggct ggatcagaat     1080
gagtcttga                                                              1089
```

<210> SEQ ID NO 47
<211> LENGTH: 362
<212> TYPE: PRT
<213> ORGANISM: Artificial Sequence
<220> FEATURE:
<223> OTHER INFORMATION: The amino acid sequence of the ALT03M3

<400> SEQUENCE: 47

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
                20                  25                  30

Pro Gly Lys Phe Asp Pro Ser Lys Pro Val Ile Arg Ala Ser Asn Glu
            35                  40                  45

Gly Ala Thr Phe Tyr Ile Asn Gln Met Tyr Val Asn Phe Gln Ala Pro
        50                  55                  60

Val Arg Pro Arg Gly Leu Pro Leu Val Phe Trp His Gly Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
                100                 105                 110

Gly Arg Gly Arg Gly Asn Ile Pro Thr Phe Asn Gly Pro Phe Gly Gln
            115                 120                 125

Leu Glu Glu Glu Ser Ile Val Asn Thr Val Thr Ala Asn Val Ser Lys
        130                 135                 140

Glu Arg Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
                180                 185                 190

Val Val Lys Leu Val Thr His Ile Gly Pro Cys Val Leu Val Thr His
            195                 200                 205

Ser Ala Ser Gly Val Leu Gly Met Arg Val Ala Thr His Ala Lys Asn
        210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
                245                 250                 255

Phe Pro Pro Phe Glu Ile Gln Glu Ser Tyr Phe Lys Lys Leu Ala Lys
                260                 265                 270

Ile Pro Ile Gln Phe Val Phe Gly Asp Asn Ile Pro Lys Asn Pro Lys
            275                 280                 285

Ser Ala Tyr Trp Phe Leu Asp Trp Trp Arg Val Thr Arg Tyr Ala His
        290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
                325                 330                 335

Thr Asp Arg Asn Asn Val Gln Val Ala Ser Leu Leu Ser Asp Phe Leu
                340                 345                 350

Gly Lys His Gly Leu Asp Gln Asn Glu Ser
            355                 360
```

<210> SEQ ID NO 48
<211> LENGTH: 1089
<212> TYPE: DNA
<213> ORGANISM: Artificial Sequence
<220> FEATURE:
<223> OTHER INFORMATION: the ALT03M3 nucleotide sequence encoding the
      amino acid sequence of the herbicide tolerant protein ALT03M3

<400> SEQUENCE: 48

```
atggaaactg acaacgtgga gcttgcccaa tcgaagcgga aggttgtcct tgctgaacaa      60
ggcagtttct acatcggggg cagaacagta accgggcctg aaaattcga tccgtcaaag     120 ccggtaattc gagcttccaa cgaaggtgcc acgttttata tcaatcaaat gtacgtaaac     180
tttcaagctc ctgtgcgccc tcgtgggctg cctctagtct tttggcatgg ggcggacta      240 accggccata tctgggaatc taccccagac ggccgccccg gatttcagac cctctttgtt     300
caagatcggc atacggtcta cacgattgat cagccagggc gcggaagggg caatattcct     360 accttttaatg gcccttttgg gcagttggaa gaagagtcga ttgttaacac tgttaccgca    420
aacgtcagta aagaaagagc gtgggttaga gatcgactag ggcccgctcc cggccagttt     480
tttgagaaca gccaattccc acgtggttat gaagacaact acttcaagga gatgggcttc    540
agtccgtcga tctcatcaga tgagatagtc gacgctgttg ttaaactagt aactcacata    600
ggtccttgtg ttctggtgac ccattcggct tccggagtac tgggcatgcg agtcgcgaca    660
cacgccaaga acgtgagggg gatcgttgct tatgagcctg cgacaagtat ctttcccaaa    720
ggaaaagtgc ctgagatacc gcctctcgcc gataaaaagt cgcaaatttt ccgccgttc    780 gagatccagg agtcttactt taagaagctc gcgaagatac ccattcagtt tgtcttcgga    840
gataatatcc ccaagaaccc taaatccgcc tattggttct tggactggtg agagtcact     900 cgctacgctc acagcttgtc actcgaggct atcaataagc tcggtggtca agcgtctctt     960 ttggattttgc cgactgcggg acttcgcggc aacacgcatt ttccattcac cgaccggaat    1020
aacgtgcagg tcgcttctct gttatctgat ttcctcggaa agcacggctt agatcagaac    1080
gaaagctga                                                            1089
```

<210> SEQ ID NO 49
<211> LENGTH: 1089
<212> TYPE: DNA
<213> ORGANISM: Artificial Sequence
<220> FEATURE:
<223> OTHER INFORMATION: the ALT03M3-01 nucleotide sequence encoding the
      amino acid sequence corresponding to the herbicide tolerant
      protein ALT03M3 and based on the soybean codon usage bias

<400> SEQUENCE: 49

```
atggagactg ataacgtgga actcgcccaa tctaagagaa aggtggtgct ggctgaacaa      60
gggtcatttt acatagggggg taggactgtt actggtcctg caagtttga tccatccaaa    120 cctgtgatac gagccagtaa cgaaggagca acattctata ttaaccaaat gtatgttaac    180
ttccaggccc cagtgagacc tagggggactt ccattggttt tctggcatgg aggtggcttg    240
actggtcaca tctgggagtc tacacctgac ggcagacccg gtttcaaac cctcttcgtt    300 caggataggc ataccgtgta cactattgac caacctggga gaggaagggg taacatccca    360
acttttaacg gaccttttcgg acagttggag gagagagta ttgttaacac tgtgacagcc    420
aatgtatcaa aggaacgagc ctgggtgaga gatagggcttg ccctgctcc cgggcaatttt    480 ttcgagaact ctcagtttcc tagaggctat gaagacaatt actttaagga gatgggattc    540
```

```
agcccatcta tatccagtga tgaaattgtt gacgctgttg tgaaactcgt gacccatatt    600
ggtccttgtg ttctggtgac tcactcagca tccggcgttc ttgggatgag agtggctaca    660
cacgcaaaga atgttagggg aattgtggcc tatgaaccag ctacctcaat cttccccaag    720
ggaaaagttc cagagatacc acctctcgct gataagaaaa gccaaatctt tccccccattc   780 gaaatacagg agtcttactt taagaaactt gccaagattc caatccaatt tgttttcgga    840
gataacatcc ccaagaatcc aaaatcagca tattggttcc tggactggtg gagagtgaca    900
agatacgcac atagtctcag cctggaggcc ataaacaaat tgggggggaca agcttcccctt  960 ttggatcttc ctactgcagg attgagaggt aatacacact ttcccttcac cgataggaac   1020
aatgttcagg tggcttctct cctgtcagac tttctgggta aacacggtct ggatcaaaat   1080
gagagctga                                                           1089
```

<210> SEQ ID NO 50
<211> LENGTH: 1089
<212> TYPE: DNA
<213> ORGANISM: Artificial Sequence
<220> FEATURE:
<223> OTHER INFORMATION: the ALT03M3-02 nucleotide sequence encoding the
      amino acid sequence corresponding to the herbicide tolerant
      protein ALT03M3 and based on the maize codon usage bias

<400> SEQUENCE: 50

```
atggagactg ataacgtgga gctggcgcag agcaagagga aggtggttct ggctgagcag     60
gggtcgttct acattggggg gcggactgtg accgggcccg gcaagttcga cccatcgaag    120
cctgtcattc gggcgtctaa cgagggcgct acgttctaca tcaaccagat gtacgtgaat    180
ttccaggctc ccgtccgccc aaggggcctc ccactggtgt tctggcacgg cgggggcctg    240
acaggccata tctgggagtc cactccagat ggccgcccag ggttccagac actcttcgtt    300
caggacaggc acacagtgta cactattgat cagccaggga ggggcagggg gaacatccct    360
accttcaatg gcccattcgg gcagctggag gaggagtcca tcgtgaacac cgtcacggcg    420
aatgtgagca aggagcgggc ttgggtcagg accggctcg gcccggcccc agggcagttc     480
ttcgagaact ctcagttccc ccggggctac gaggataatt acttcaagga gatgggcttc    540
tcaccatcca tctcgtctga cgagattgtc gatgccgtgg tcaagctcgt tacccacatc    600
ggcccttgcg ttctggtgac gcatagcgct tcgggcgtcc tcgggatgag ggttgctaca    660
catgcgaaga acgttcgcgg catcgtggct tacgagccgg ccacttccat ttttccccaag   720 ggcaaggtgc cagagatccc accactggcc gacaagaagt cacagatctt cccacctttc    780
gagattcagg agtcctactt caagaagctc gctaagatcc ccattcagtt cgtgttcggc    840
gacaacattc ctaagaatcc gaagagcgcg tactggttcc tggattggtg gcgcgtcacg    900
cgctacgcgc actctctctc actggaggct atcaacaagc tcgggggcca ggcctcgctc    960
ctggacctcc ctaccgctgg cctgaggggg aacacccatt tcccgttcac ggatcggaac   1020
aatgtccagg ttgcgtccct cctgagcgat ttcctcggca agcacgggct ggatcagaat   1080
gagtcttga                                                           1089
```

<210> SEQ ID NO 51
<211> LENGTH: 350
<212> TYPE: PRT
<213> ORGANISM: Artificial Sequence
<220> FEATURE:
<223> OTHER INFORMATION: the amino acid sequence of ALT04

<400> SEQUENCE: 51

```
Met Ser Lys Arg Lys Val Val Leu Ala Glu Gln Gly Ser Phe Tyr Ile
1               5                   10                  15

Gly Gly Arg Thr Val Thr Gly Pro Gly Lys Phe Asp Pro Ser Lys Pro
            20                  25                  30

Val Ile Pro Tyr Ser Asn Glu Gly Ala Thr Phe Tyr Ile Asn Gln Met
        35                  40                  45

Tyr Val Asn Phe Gln Ala Pro Val Arg Pro Arg Gly Leu Pro Leu Val
50                  55                  60

Phe Trp His Gly Gly Gly Leu Thr Gly His Ile Trp Glu Ser Thr Pro
65                  70                  75                  80

Asp Gly Arg Pro Gly Phe Gln Thr Leu Phe Val Gln Asp Arg His Thr
            85                  90                  95

Val Tyr Thr Ile Asp Gln Pro Gly Arg Gly Arg Gly Asn Ile Pro Thr
        100                 105                 110

Phe Asn Gly Pro Phe Gly Gln Leu Glu Glu Ser Ile Val Asn Thr
            115                 120                 125

Val Thr Gly Asn Ser Ser Lys Glu Gly Ala Trp Val Arg Asp Arg Leu
130                 135                 140

Gly Pro Ala Pro Gly Gln Phe Phe Glu Asn Ser Gln Phe Pro Arg Gly
145                 150                 155                 160

Tyr Glu Asp Asn Tyr Phe Lys Glu Met Gly Phe Ser Pro Ser Ile Ser
                165                 170                 175

Ser Asp Glu Ile Val Asp Ala Val Lys Leu Val Thr His Ile Gly
            180                 185                 190

Pro Cys Val Leu Val Thr His Ser Ala Ser Gly Val Leu Gly Met Arg
        195                 200                 205

Val Ala Thr His Ala Lys Asn Val Arg Gly Ile Val Ala Tyr Glu Pro
210                 215                 220

Ala Thr Ser Ile Phe Pro Lys Gly Lys Val Pro Glu Ile Pro Leu
225                 230                 235                 240

Ala Asp Lys Lys Ser Gln Ile Phe Pro Pro Phe Glu Ile Gln Glu Ser
            245                 250                 255

Tyr Phe Lys Lys Leu Ala Lys Ile Pro Ile Gln Phe Val Phe Gly Asp
        260                 265                 270

Asn Ile Pro Lys Asn Pro Lys Ser Ala Tyr Trp Phe Leu Asp Trp Trp
            275                 280                 285

Arg Val Thr Arg Tyr Ala His Ser Leu Ser Leu Glu Ala Ile Asn Lys
290                 295                 300

Leu Gly Gly Gln Ala Ser Leu Leu Asp Leu Pro Thr Ala Gly Leu Arg
305                 310                 315                 320

Gly Asn Thr His Phe Pro Phe Thr Asp Arg Asn Asn Val Gln Val Ala
                325                 330                 335

Ser Leu Leu Ser Asp Phe Leu Gly Lys His Gly Leu Asp Gln
            340                 345                 350
```

<210> SEQ ID NO 52
<211> LENGTH: 1053
<212> TYPE: DNA
<213> ORGANISM: Artificial Sequence
<220> FEATURE:
<223> OTHER INFORMATION: the ALT04 nucleotide sequence encoding the amino acid sequence of ALT04

<400> SEQUENCE: 52

```
atgtcgaagc ggaaggttgt ccttgctgaa caaggcagtt tctacatcgg ggcagaaca      60 gtaaccgggc ctggaaaatt cgatccgtca aagccggtaa ttccatattc aacgaaggt     120 gccacgtttt atatcaatca aatgtacgta aactttcaag ctcctgtgcg ccctcgtggg    180
ctgcctctag tcttttggca tggggggcgga ctaaccggcc atatctggga atctacccca   240
gacggccgcc ccggatttca gaccctcttt gttcaagatc ggcatacggt ctacacgatt    300
gatcagccag ggcgcggaag gggcaatatt cctaccttta atggccctt tgggcagttg     360 gaagaagagt cgattgttaa cactgttacc ggaaactcca gtaaagaagg agcgtgggtt    420
agagatcgac tagggcccgc tcccggccag ttttttgaga cagccaatt cccacgtggt     480 tatgaagaca actacttcaa ggagatgggg ttcagtccgt cgatctcatc agatgagata    540
gtcgacgctg ttgttaaact agtaactcac ataggtcctt gtgttctggt gacccattcg    600
gcttccggag tactgggcat gcgagtcgcg acacacgcca agaacgtgag ggggatcgtt    660
gcttatgagc ctgcgacaag tatctttccc aaaggaaaag tgcctgagat accgcctctc    720
gccgataaaa agtcgcaaat tttcccgccg ttcgagatcc aggagtctta ctttaagaag    780
ctcgcgaaga tacccattca gtttgtcttc ggagataata tccccaagaa ccctaaatcc    840
gcctattggt tcttggactg gtggagagtc actcgctacg ctcacagctt gtcactcgag    900
gctatcaata gctcggtgg tcaagcgtct cttttggatt tgccgactgc gggacttcgc    960
ggcaacacgc attttccatt caccgaccgg aataacgtgc aggtcgcttc tctgttatct   1020
gatttcctcg gaaagcacgg cttagatcag tga                                1053
```

<210> SEQ ID NO 53
<211> LENGTH: 1053
<212> TYPE: DNA
<213> ORGANISM: Artificial Sequence
<220> FEATURE:
<223> OTHER INFORMATION: the ALT04-01 nucleotide sequence encoding the amino acid sequence corresponding to the ALT04 and based on the soybean codon usage bias

<400> SEQUENCE: 53

```
atgtctaaga gaaaggtggt gctggctgaa caagggtcat tttacatagg gggtaggact    60
gttactggtc ctggcaagtt tgatccatcc aaacctgtga taccctacag taacgaagga   120
gcaacattct atattaacca aatgtatgtt aacttccagg ccccagtgag acctagggga   180
cttccattgg tttttctggca tggaggtggc ttgactggtc acatctggga gtctacacct   240
gacggcagac ccgggtttca aaccctcttc gttcaggata ggcataccgt gtacactatt   300
gaccaacctg ggagaggaag gggtaacatc ccaacttta acggaccttt cggacagttg    360
gaggaagaga gtattgttaa cactgtgaca ggaaattctt caaaggaagg tgcctgggtg   420
agagataggc ttggccctgc tcccgggcaa ttttccgaga ctctcagtt tcctagaggc    480 tatgaagaca attactttaa ggagatggga ttcagcccat ctatatccag tgatgaaatt    540
gttgacgctg ttgtgaaact cgtgacccat attggtcctt gtgttctggt gactcactca   600
gcatccggcg ttcttgggat gagagtggct acacacgcaa agaatgttag gggaattgtg   660
gcctatgaac cagctacctc aatcttcccc aagggaaaag ttccagagat accacctctc   720
gctgataaga aaagccaaat ctttccccca ttcgaaatac aggagtctta ctttaagaaa   780
cttgccaaga ttccaatcca atttgttttc ggagataaca tccccaagaa tccaaaatca   840
gcatattggt tcctggactg gtggagagtg acaagatacg cacatagtct cagcctggag   900
gccataaaca aattgggggg acaagcttcc ctttggatc ttcctactgc aggattgaga   960
```

```
ggtaatacac actttcccctt caccgatagg aacaatgttc aggtggcttc tctcctgtca   1020
gactttctgg gtaaacacgg tctggatcaa tga                                 1053

<210> SEQ ID NO 54
<211> LENGTH: 1053
<212> TYPE: DNA
<213> ORGANISM: Artificial Sequence
<220> FEATURE:
<223> OTHER INFORMATION: the ALT04-02 nucleotide sequence encoding the
      amino acid sequence corresponding to the herbicide tolerant
      protein ALT04 and based on the maize codon usage bias

<400> SEQUENCE: 54
atgagcaaga ggaaggtggt tctggctgag caggggtcgt tctacattgg ggggcggact     60
gtgaccgggc ccggcaagtt cgacccatcg aagcctgtca ttccgtactc taacgagggc    120
gctacgttct acatcaacca gatgtacgtg aatttccagg ctcccgtccg cccaaggggc    180
ctcccactgg tgttctggca cggcgggggc ctgacaggcc atatctggga gtccactcca    240
gatggccgcc cagggttcca gacactcttc gttcaggaca ggcacacagt gtacactatt    300
gatcagccag ggaggggcag gggaacatc cctaccttca atggcccatt cgggcagctg    360
gaggaggagt ccatcgtgaa caccgtcacg ggcaattcca gcaaggaggg ggcttgggtc    420
agggaccggc tcgccccggc cccagggcag ttcttcgaga actctcagtt ccccccgggc    480
tacgaggata attacttcaa ggagatgggc ttctcaccat ccatctcgtc tgacgagatt    540
gtcgatgccg tggtcaagct cgttacccac atcggccctt gcgttctggt gacgcatagc    600
gcttcgggcg tcctcgggat gagggttgct acacatgcga agaacgttcg cggcatcgtg    660
gcttacgagc cggccacttc catttttcccc aagggcaagg tgccagagat cccaccactg    720
gccgacaaga agtcacagat cttcccacct ttcgagattc aggagtccta cttcaagaag    780
ctcgctaaga tccccattca gttcgtgttc ggcgacaaca ttcctaagaa tccgaagagc    840
gcgtactggt tcctggattg gtggcgcgtc acgcgctacg cgcactctct ctcactggag    900
gctatcaaca agctcggggg ccaggcctcg ctcctggacc tccctaccgc tggcctgagg    960
gggaacaccc atttcccgtt cacgatcgg aacaatgtcc aggttgcgtc cctcctgagc   1020
gatttcctcg gcaagcacgg gctggatcag tga                                1053

<210> SEQ ID NO 55
<211> LENGTH: 350
<212> TYPE: PRT
<213> ORGANISM: Artificial Sequence
<220> FEATURE:
<223> OTHER INFORMATION: the amino acid sequence of the ALT04M1

<400> SEQUENCE: 55

Met Ser Lys Arg Lys Val Val Leu Ala Glu Gln Gly Ser Phe Tyr Ile
1               5                   10                  15

Gly Gly Arg Thr Val Thr Gly Pro Gly Lys Phe Asp Pro Ser Lys Pro
            20                  25                  30

Val Ile Pro Tyr Ser Asn Glu Gly Ala Thr Phe Tyr Ile Asn Gln Met
        35                  40                  45

Tyr Val Asn Phe Gln Ala Pro Val Arg Pro Arg Gly Leu Pro Leu Val
    50                  55                  60

Phe Trp His Gly Gly Gly Leu Thr Gly His Ile Trp Glu Ser Thr Pro
65                  70                  75                  80

Asp Gly Arg Pro Gly Phe Gln Thr Leu Phe Val Gln Asp Arg His Thr
```

```
                         85                  90                  95
Val Tyr Thr Ile Asp Gln Pro Gly Arg Gly Arg Gly Asn Ile Pro Thr
                    100                 105                 110

Phe Asn Gly Pro Phe Gly Gln Leu Glu Glu Ser Ile Val Asn Thr
            115                 120                 125

Val Thr Ala Asn Ser Ser Lys Glu Gly Ala Trp Val Arg Asp Arg Leu
130                 135                 140

Gly Pro Ala Pro Gly Gln Phe Phe Glu Asn Ser Gln Phe Pro Arg Gly
145                 150                 155                 160

Tyr Glu Asp Asn Tyr Phe Lys Glu Met Gly Phe Ser Pro Ser Ile Ser
                165                 170                 175

Ser Asp Glu Ile Val Asp Ala Val Lys Leu Val Thr His Ile Gly
            180                 185                 190

Pro Cys Val Leu Val Thr His Ser Ala Ser Gly Val Leu Gly Met Arg
                195                 200                 205

Val Ala Thr His Ala Lys Asn Val Arg Gly Ile Val Ala Tyr Glu Pro
210                 215                 220

Ala Thr Ser Ile Phe Pro Lys Gly Lys Val Pro Glu Ile Pro Pro Leu
225                 230                 235                 240

Ala Asp Lys Lys Ser Gln Ile Phe Pro Pro Phe Glu Ile Gln Glu Ser
                245                 250                 255

Tyr Phe Lys Lys Leu Ala Lys Ile Pro Ile Gln Phe Val Phe Gly Asp
                260                 265                 270

Asn Ile Pro Lys Asn Pro Lys Ser Ala Tyr Trp Phe Leu Asp Trp Trp
                275                 280                 285

Arg Val Thr Arg Tyr Ala His Ser Leu Ser Leu Glu Ala Ile Asn Lys
                290                 295                 300

Leu Gly Gly Gln Ala Ser Leu Leu Asp Leu Pro Thr Ala Gly Leu Arg
305                 310                 315                 320

Gly Asn Thr His Phe Pro Phe Thr Asp Arg Asn Asn Val Gln Val Ala
                325                 330                 335

Ser Leu Leu Ser Asp Phe Leu Gly Lys His Gly Leu Asp Gln
                340                 345                 350

<210> SEQ ID NO 56
<211> LENGTH: 1053
<212> TYPE: DNA
<213> ORGANISM: Artificial Sequence
<220> FEATURE:
<223> OTHER INFORMATION: the ALT04M1 nucleotide sequence encoding the
      amino acid sequence of the herbicide tolerant protein ALT04M1

<400> SEQUENCE: 56
atgtcgaagc ggaaggttgt ccttgctgaa caaggcagtt tctacatcgg gggcagaaca      60
gtaaccgggc ctggaaaatt cgatccgtca aagccggtaa ttccatattc caacgaaggt     120
gccacgtttt atatcaatca aatgtacgta aactttcaag ctcctgtgcg ccctcgtggg     180
ctgcctctag tcttttggca tggggggcgga ctaaccggcc atatctggga atctacccca    240
gacggccgcc ccggatttca gaccctcttt gttcaagatc ggcataccggt ctacacgatt    300 gatcagccag ggcgcggaag gggcaatatt cctaccttta atggcccttt tgggcagttg    360
gaagaagagt cgattgttaa cactgttacc gcaaactcca gtaaagaagg agcgtgggtt    420
agagatcgac tagggcccgc tcccggccag ttttttgaga acagccaatt ccacgtggt     480 tatgaagaca actacttcaa ggagatgggg ttcagtccgt cgatctcatc agatgagata    540
```

```
gtcgacgctg ttgttaaact agtaactcac ataggtcctt gtgttctggt gacccattcg      600
gcttccggag tactgggcat gcgagtcgcg acacacgcca agaacgtgag ggggatcgtt      660
gcttatgagc ctgcgacaag tatctttccc aaaggaaaag tgcctgagat accgcctctc      720
gccgataaaa agtcgcaaat ttcccgccg ttcgagatcc aggagtctta ctttaagaag       780
ctcgcgaaga tacccattca gtttgtcttc ggagataata tccccaagaa ccctaaatcc      840
gcctattggt tcttggactg gtggagagtc actcgctacg ctcacagctt gtcactcgag      900
gctatcaata agctcggtgg tcaagcgtct cttttggatt tgccgactgc gggacttcgc      960
ggcaacacgc attttccatt caccgaccgg aataacgtgc aggtcgcttc tctgttatct     1020
gatttcctcg gaaagcacgg cttagatcag tga                                  1053
```

<210> SEQ ID NO 57
<211> LENGTH: 1053
<212> TYPE: DNA
<213> ORGANISM: Artificial Sequence
<220> FEATURE:
<223> OTHER INFORMATION: the ALT04M1-01 nucleotide sequence encoding the amino acid sequence corresponding to the herbicide tolerant protein ALT04M1 and based on the soybean codon usage bias

<400> SEQUENCE: 57

```
atgtctaaga gaaaggtggt gctggctgaa caagggtcat tttacatagg gggtaggact       60
gttactggtc ctggcaagtt tgatccatcc aaacctgtga tacccacag taacgaagga     120 gcaacattct atattaacca aatgtatgtt aacttccagg ccccagtgag acctagggga      180
cttccattgg ttttctggca tggaggtggc ttgactggtc acatctggga gtctacacct      240
gacggcagac ccgggtttca aaccctcttc gttcaggata ggcataccgt gtacactatt      300
gaccaacctg ggagaggaag gggtaacatc ccaactttta acggaccttt cggacagttg      360
gaggaagaga gtattgttaa cactgtgaca gccaattctt caaaggaagg tgcctgggtg      420
agagataggc ttgccctgc tcccgggcaa tttttcgaga actctcagtt tcctagaggc       480
tatgaagaca attactttaa ggagatggga ttcagcccat ctatatccag tgatgaaatt      540
gttgacgctg ttgtgaaact cgtgacccat attggtcctt gtgttctggt gactcactca      600
gcatccggcg ttcttgggat gagagtggct acacacgcaa agaatgttag gggaattgtg      660
gcctatgaac cagctacctc aatcttcccc aagggaaaag ttccagagat accctctc       720 gctgataaga aaagccaaat cttttccccca ttcgaaatac aggagtctta ctttaagaaa     780
cttgccaaga ttccaatcca atttgtttc ggagataaca tccccaagaa tccaaaatca      840
gcatattggt tcctggactg gtggagagtg acaagatacg cacatagtct cagcctggag      900
gccataaaca aattgggggg acaagcttcc cttttggatc ttcctactgc aggattgaga      960
ggtaatacac actttccctt caccgatagg aacaatgttc aggtggcttc tctcctgtca     1020
gactttctgg gtaaacacgg tctggatcaa tga                                  1053
```

<210> SEQ ID NO 58
<211> LENGTH: 1053
<212> TYPE: DNA
<213> ORGANISM: Artificial Sequence
<220> FEATURE:
<223> OTHER INFORMATION: the ALT04M1-02 nucleotide sequence encoding the amino acid sequence corresponding to the herbicide tolerant protein ALT04M1 and based on the maize codon usage bias

<400> SEQUENCE: 58

```
atgagcaaga ggaaggtggt tctggctgag caggggtcgt tctacattgg ggggcggact       60
```

```
gtgaccgggc cggcaagtt cgacccatcg aagcctgtca ttccgtactc taacgagggc    120
gctacgttct acatcaacca gatgtacgtg aatttccagg ctcccgtccg cccaaggggc    180
ctcccactgg tgttctggca cggcgggggc ctgacaggcc atatctggga gtccactcca    240
gatggccgcc cagggttcca gacactcttc gttcaggaca ggcacacagt gtacactatt    300
gatcagccag ggaggggcag ggggaacatc cctaccttca atggcccatt cgggcagctg    360
gaggaggagt ccatcgtgaa caccgtcacg gcgaattcca gcaaggaggg ggcttgggtc    420
agggaccggc tcggcccggc cccagggcag ttcttcgaga actctcagtt ccccgggggc    480
tacgaggata attacttcaa ggagatgggc ttctcaccat ccatctcgtc tgacgagatt    540
gtcgatgccg tggtcaagct cgttacccac atcggccctt gcgttctggt gacgcatagc    600
gcttcgggcg tcctcgggat gagggttgct acacatgcga agaacgttcg cggcatcgtg    660
gcttacgagc cggccacttc cattttcccc aagggcaagg tgccagagat cccaccactg    720
gccgacaaga agtcacagat cttcccacct ttcgagattc aggagtccta cttcaagaag    780
ctcgctaaga tccccattca gttcgtgttc ggcgacaaca ttcctaagaa tccgaagagc    840
gcgtactggt tcctggattg gtggcgcgtc acgcgctacg cgcactctct ctcactggag    900
gctatcaaca agctcggggg ccaggcctcg ctcctggacc tccctaccgc tggcctgagg    960
gggaacaccc atttcccgtt cacggatcgg aacaatgtcc aggttgcgtc cctcctgagc   1020
gatttcctcg gcaagcacgg gctggatcag tga                                1053
```

<210> SEQ ID NO 59
<211> LENGTH: 350
<212> TYPE: PRT
<213> ORGANISM: Artificial Sequence
<220> FEATURE:
<223> OTHER INFORMATION: the amino acid sequence of the ALT04M2

<400> SEQUENCE: 59

```
Met Ser Lys Arg Lys Val Val Leu Ala Glu Gln Gly Ser Phe Tyr Ile
1               5                   10                  15

Gly Gly Arg Thr Val Thr Gly Pro Gly Lys Phe Asp Pro Ser Lys Pro
            20                  25                  30

Val Ile Pro Tyr Ser Asn Glu Gly Ala Thr Phe Tyr Ile Asn Gln Met
        35                  40                  45

Tyr Val Asn Phe Gln Ala Pro Val Arg Pro Arg Gly Leu Pro Leu Val
    50                  55                  60

Phe Trp His Gly Gly Leu Thr Gly His Ile Trp Glu Ser Thr Pro
65                  70                  75                  80

Asp Gly Arg Pro Gly Phe Gln Thr Leu Phe Val Gln Asp Arg His Thr
                85                  90                  95

Val Tyr Thr Ile Asp Gln Pro Gly Arg Gly Arg Gly Asn Ile Pro Thr
            100                 105                 110

Phe Asn Gly Pro Phe Gly Gln Leu Glu Glu Glu Ser Ile Val Asn Thr
        115                 120                 125

Val Thr Gly Asn Val Ser Lys Glu Gly Ala Trp Val Arg Asp Arg Leu
    130                 135                 140

Gly Pro Ala Pro Gly Gln Phe Phe Glu Asn Ser Gln Phe Pro Arg Gly
145                 150                 155                 160

Tyr Glu Asp Asn Tyr Phe Lys Glu Met Gly Phe Ser Pro Ser Ile Ser
                165                 170                 175

Ser Asp Glu Ile Val Asp Ala Val Val Lys Leu Val Thr His Ile Gly
```

```
                 180                 185                 190
Pro Cys Val Leu Val Thr His Ser Ala Ser Gly Val Leu Gly Met Arg
             195                 200                 205

Val Ala Thr His Ala Lys Asn Val Arg Gly Ile Val Ala Tyr Glu Pro
210                 215                 220

Ala Thr Ser Ile Phe Pro Lys Gly Lys Val Pro Glu Ile Pro Pro Leu
225                 230                 235                 240

Ala Asp Lys Lys Ser Gln Ile Phe Pro Phe Glu Ile Gln Glu Ser
             245                 250                 255

Tyr Phe Lys Lys Leu Ala Lys Ile Pro Ile Gln Phe Val Phe Gly Asp
             260                 265                 270

Asn Ile Pro Lys Asn Pro Lys Ser Ala Tyr Trp Phe Leu Asp Trp Trp
        275                 280                 285

Arg Val Thr Arg Tyr Ala His Ser Leu Ser Leu Glu Ala Ile Asn Lys
             290                 295                 300

Leu Gly Gly Gln Ala Ser Leu Leu Asp Leu Pro Thr Ala Gly Leu Arg
305                 310                 315                 320

Gly Asn Thr His Phe Pro Phe Thr Asp Arg Asn Asn Val Gln Val Ala
                 325                 330                 335

Ser Leu Leu Ser Asp Phe Leu Gly Lys His Gly Leu Asp Gln
             340                 345                 350

<210> SEQ ID NO 60
<211> LENGTH: 1053
<212> TYPE: DNA
<213> ORGANISM: Artificial Sequence
<220> FEATURE:
<223> OTHER INFORMATION: the ALT04M2 nucleotide sequence encoding the
      amino acid sequence of the herbicide tolerant protein ALT04M2

<400> SEQUENCE: 60
atgtcgaagc ggaaggttgt ccttgctgaa caaggcagtt tctacatcgg gggcagaaca      60
gtaaccgggc ctggaaaatt cgatccgtca agccggtaa ttccatattc caacgaaggt     120
gccacgtttt atatcaatca aatgtacgta aactttcaag ctcctgtgcg ccctcgtggg     180
ctgcctctag tcttttggca tggggcgga ctaaccggcc atatctggga atctacccca      240
gacggccgcc ccggatttca gaccctcttt gttcaagatc ggcatacggt ctacacgatt     300
gatcagccag ggcgcggaag gggcaatatt cctaccttta atggcccttt tgggcagttg     360
gaagaagagt cgattgttaa cactgttacc ggaaacgtca gtaaagaagg agcgtgggtt     420
agagatcgac tagggcccgc tcccggccag tttttttgaga acagccaatt cccacgtggt     480
tatgaagaca actacttcaa ggagatgggg ttcagtccgt cgatctcatc agatgagata     540
gtcgacgctg ttgttaaact agtaactcac ataggtcctt gtgttctggt gacccattcg     600
gcttccggag tactgggcat gcgagtcgcg acacacgcca agaacgtgag ggggatcgtt     660
gcttatgagc ctgcgacaag tatctttccc aaaggaaaag tgcctgagat accgcctctc     720
gccgataaaa agtcgcaaat ttttcccgccg ttcgagatcc aggagtctta ctttaagaag     780
ctcgcgaaga tacccattca gtttgtcttc ggagataata tccccaagaa ccctaaatcc     840
gcctattggt tcttggactg gtggagagtc actcgctacg ctcacagctt gtcactcgag     900
gctatcaata agctcggtgg tcaagcgtct cttttggatt tgccgactgc gggacttcgc     960
ggcaacacgc attttccatt caccgaccgg aataacgtgc aggtcgcttc tctgttatct    1020
gatttcctcg gaaagcacgg cttagatcag tga                                 1053
```

<210> SEQ ID NO 61
<211> LENGTH: 1053
<212> TYPE: DNA
<213> ORGANISM: Artificial Sequence
<220> FEATURE:
<223> OTHER INFORMATION: the ALT04M2-01 nucleotide sequence encoding the
      amino acid sequence corresponding to the herbicide tolerant
      protein ALT04M2 and based on the soybean codon usage bias;

<400> SEQUENCE: 61

```
atgtctaaga gaaaggtggt gctggctgaa caagggtcat tttacatagg gggtaggact      60
gttactggtc ctggcaagtt tgatccatcc aaacctgtga taccctacag taacgaagga     120
gcaacattct atattaacca aatgtatgtt aacttccagg ccccagtgag acctagggga     180
cttccattgg ttttctggca tggaggtggc ttgactggtc acatctggga gtctacacct     240
gacggcagac ccgggtttca aaccctcttc gttcaggata ggcataccgt gtacactatt     300
gaccaacctg ggagaggaag gggtaacatc ccaactttta acggaccttt cggacagttg     360
gaggaagaga gtattgttaa cactgtgaca ggaaatgtat caaaggaagg tgcctgggtg     420
agagataggc ttggccctgc tcccgggcaa ttttttcgaga actctcagtt tcctagaggc     480
tatgaagaca attactttaa ggagatggga ttcagcccat ctatatccag tgatgaaatt     540
gttgacgctg ttgtgaaact cgtgacccat attggtcctt gtgttctggt gactcactca     600
gcatccggcg ttcttgggat gagagtggct acacacgcaa agaatgttag gggaattgtg     660
gcctatgaac cagctacctc aatcttcccc aagggaaaag ttccagagat accacctctc     720
gctgataaga aaagccaaat ctttcccccca ttcgaaatac aggagtctta ctttaagaaa     780
cttgccaaga ttccaatcca atttgttttc ggagataaca tccccaagaa tccaaaatca     840
gcatattggt tcctggactg gtggagagtg acaagatacg cacatagtct cagcctggag     900
gccataaaca aattgggggg acaagcttcc cttttggatc ttcctactgc aggattgaga     960
ggtaatacac actttccctt caccgatagg aacaatgttc aggtggcttc tctcctgtca    1020
gactttctgg gtaaacacgg tctggatcaa tga                                1053
```

<210> SEQ ID NO 62
<211> LENGTH: 1053
<212> TYPE: DNA
<213> ORGANISM: Artificial Sequence
<220> FEATURE:
<223> OTHER INFORMATION: the ALT04M2-02 nucleotide sequence encoding the
      amino acid sequence corresponding to the herbicide tolerant
      protein ALT04M2 and based on the maize codon usage bias

<400> SEQUENCE: 62

```
atgagcaaga ggaaggtggt tctggctgag caggggtcgt tctacattgg ggggcggact      60
gtgaccgggc ccggcaagtt cgacccatcg aagcctgtca ttccgtactc taacgagggc     120
gctacgttct acatcaacca gatgtacgtg aatttccagg ctcccgtccg cccaaggggc     180
ctcccactgg tgttctggca cggcgggggc ctgacaggcc atatctggga gtccactcca     240
gatggccgcc cagggttcca gacactcttc gttcaggaca ggcacacagt gtacactatt     300
gatcagccag gaggggcag ggaacatc cctaccttca atggcccatt cgggcagctg     360
gaggaggagt ccatcgtgaa caccgtcacg ggcaatgtga gcaaggaggg ggcttgggtc     420
agggaccggc tcggcccggc cccagggcag ttcttcgaga actctcagtt ccccgggggc     480
tacgaggata attcttcaa ggagatgggc ttctcaccat ccatctcgtc tgacgagatt     540
gtcgatgccg tggtcaagct cgttacccac atcggcccctt gcgttctggt gacgcatagc     600
```

```
gcttcgggcg tcctcgggat gagggttgct acacatgcga agaacgttcg cggcatcgtg    660
gcttacgagc cggccacttc catttccccc aagggcaagg tgccagagat cccaccactg    720
gccgacaaga agtcacagat cttcccacct ttcgagattc aggagtccta cttcaagaag    780
ctcgctaaga tccccattca gttcgtgttc ggcgacaaca ttcctaagaa tccgaagagc    840
gcgtactggt tcctggattg gtggcgcgtc acgcgctacg cgcactctct ctcactggag    900
gctatcaaca agctcggggg ccaggcctcg ctcctggacc tccctaccgc tggcctgagg    960
gggaacaccc atttcccgtt cacggatcgg aacaatgtcc aggttgcgtc cctcctgagc   1020
gatttcctcg gcaagcacgg gctggatcag tga                                1053
```

<210> SEQ ID NO 63
<211> LENGTH: 350
<212> TYPE: PRT
<213> ORGANISM: Artificial Sequence
<220> FEATURE:
<223> OTHER INFORMATION: the amino acid sequence of the ALT04M3

<400> SEQUENCE: 63

```
Met Ser Lys Arg Lys Val Val Leu Ala Glu Gln Gly Ser Phe Tyr Ile
1               5                   10                  15

Gly Gly Arg Thr Val Thr Gly Pro Gly Lys Phe Asp Pro Ser Lys Pro
            20                  25                  30

Val Ile Arg Ala Ser Asn Glu Gly Ala Thr Phe Tyr Ile Asn Gln Met
        35                  40                  45

Tyr Val Asn Phe Gln Ala Pro Val Arg Pro Arg Gly Leu Pro Leu Val
    50                  55                  60

Phe Trp His Gly Gly Gly Leu Thr Gly His Ile Trp Glu Ser Thr Pro
65                  70                  75                  80

Asp Gly Arg Pro Gly Phe Gln Thr Leu Phe Val Gln Asp Arg His Thr
                85                  90                  95

Val Tyr Thr Ile Asp Gln Pro Gly Arg Gly Arg Gly Asn Ile Pro Thr
            100                 105                 110

Phe Asn Gly Pro Phe Gly Gln Leu Glu Glu Glu Ser Ile Val Asn Thr
        115                 120                 125

Val Thr Ala Asn Val Ser Lys Glu Arg Ala Trp Val Arg Asp Arg Leu
    130                 135                 140

Gly Pro Ala Pro Gly Gln Phe Phe Glu Asn Ser Gln Phe Pro Arg Gly
145                 150                 155                 160

Tyr Glu Asp Asn Tyr Phe Lys Glu Met Gly Phe Ser Pro Ser Ile Ser
                165                 170                 175

Ser Asp Glu Ile Val Asp Ala Val Lys Leu Val Thr His Ile Gly
            180                 185                 190

Pro Cys Val Leu Val Thr His Ser Ala Ser Gly Val Leu Gly Met Arg
        195                 200                 205

Val Ala Thr His Ala Lys Asn Val Arg Gly Ile Val Tyr Glu Pro
    210                 215                 220

Ala Thr Ser Ile Phe Pro Lys Gly Lys Val Pro Glu Ile Pro Pro Leu
225                 230                 235                 240

Ala Asp Lys Lys Ser Gln Ile Phe Pro Pro Phe Glu Ile Gln Glu Ser
                245                 250                 255

Tyr Phe Lys Lys Leu Ala Lys Ile Pro Ile Gln Phe Val Phe Gly Asp
            260                 265                 270

Asn Ile Pro Lys Asn Pro Lys Ser Ala Tyr Trp Phe Leu Asp Trp Trp
```

```
            275                 280                 285
Arg Val Thr Arg Tyr Ala His Ser Leu Ser Leu Glu Ala Ile Asn Lys
    290                 295                 300

Leu Gly Gly Gln Ala Ser Leu Leu Asp Leu Pro Thr Ala Gly Leu Arg
305                 310                 315                 320

Gly Asn Thr His Phe Pro Phe Thr Asp Arg Asn Asn Val Gln Val Ala
                325                 330                 335

Ser Leu Leu Ser Asp Phe Leu Gly Lys His Gly Leu Asp Gln
            340                 345                 350

<210> SEQ ID NO 64
<211> LENGTH: 1053
<212> TYPE: DNA
<213> ORGANISM: Artificial Sequence
<220> FEATURE:
<223> OTHER INFORMATION: the ALT04M3 nucleotide sequence encoding the
      amino acid sequence of the herbicide tolerant protein ALT04M3

<400> SEQUENCE: 64
atgtcgaagc ggaaggttgt ccttgctgaa caaggcagtt tctacatcgg gggcagaaca      60
gtaaccgggc ctggaaaatt cgatccgtca aagccggtaa ttcgagcttc aacgaaggt     120 gccacgtttt atatcaatca aatgtacgta aactttcaag ctcctgtgcg ccctcgtggg    180
ctgcctctag tcttttggca tggggggcgga ctaaccggcc atatctggga atctacccca   240
gacggccgcc ccggatttca gaccctcttt gttcaagatc ggcatacggt ctacacgatt    300
gatcagccag ggcgcggaag gggcaatatt cctaccttta atggccccttt tgggcagttg   360 gaagaagagt cgattgttaa cactgttacc gcaaacgtca gtaaagaaag agcgtgggtt    420
agagatcgac tagggcccgc tcccggccag tttttttgaga cagccaattt cccacgtggt   480
tatgaagaca actacttcaa ggagatgggg ttcagtccgt cgatctcatc agatgagata   540
gtcgacgctg ttgttaaact agtaactcac ataggtcctt gtgttctggt gacccattcg   600
gcttccggag tactgggcat gcgagtcgcg acacacgcca gaacgtgag ggggatcgtt     660 gcttatgagc ctgcgacaag tatctttccc aaaggaaaag tgcctgagat accgcctctc    720
gccgataaaa agtcgcaaat tttcccgccg ttcgagatcc aggagtctta ctttaagaag   780
ctcgcgaaga tacccattca gttgtcttc ggagataata tccccaagaa ccctaaatcc    840
gcctattggt tcttggactg gtggagagtc actcgctacg ctcacagctt gtcactcgag   900
gctatcaata agctcggtgg tcaagcgtct cttttggatt tgccgactgc gggacttcgc    960
ggcaacacgc attttccatt caccgaccgg aataacgtgc aggtcgcttc tctgttatct  1020
gatttcctcg gaaagcacgg cttagatcag tga                                1053

<210> SEQ ID NO 65
<211> LENGTH: 1053
<212> TYPE: DNA
<213> ORGANISM: Artificial Sequence
<220> FEATURE:
<223> OTHER INFORMATION: the ALT04M3-01 nucleotide sequence encoding the
      amino acid sequence corresponding to the herbicide tolerant
      protein ALT04M3 and based on the soybean codon usage bias;

<400> SEQUENCE: 65
atgtctaaga gaaaggtggt gctggctgaa caagggtcat tttacatagg gggtaggact     60
gttactggtc ctggcaagtt tgatccatcc aaacctgtga tacgagccag taacgaagga   120
gcaacattct atattaacca aatgtatgtt aacttccagg ccccagtgag acctagggga   180
```

```
cttccattgg ttttctggca tggaggtggc ttgactggtc acatctggga gtctacacct      240
gacggcagac ccgggtttca aaccctcttc gttcaggata ggcataccgt gtacactatt      300
gaccaacctg ggagaggaag gggtaacatc ccaacttttta acggaccttt cggacagttg     360
gaggaagaga gtattgttaa cactgtgaca gccaatgtat caaaggaacg agcctgggtg      420
agagataggc ttggccctgc tcccgggcaa tttttcgaga actctcagtt tcctagaggc      480
tatgaagaca attactttaa ggagatggga ttcagcccat ctatatccag tgatgaaatt      540
gttgacgctg ttgtgaaact cgtgacccat attggtcctt gtgttctggt gactcactca      600
gcatccggcg ttcttgggat gagagtggct acacacgcaa agaatgttag ggaattgtg      660 gcctatgaac cagctacctc aatcttcccc aagggaaaag ttccagagat accacctctc      720
gctgataaga aaagccaaat ctttccccca ttcgaaatac aggagtctta ctttaagaaa      780
cttgccaaga ttccaatcca atttgttttc ggagataaca tccccaagaa tccaaaatca     840
gcatattggt tcctggactg gtggagagtg acaagatacg cacatagtct cagcctggag     900
gccataaaca aattgggggg acaagcttcc cttttggatc ttcctactgc aggattgaga      960
ggtaatacac actttcctt caccgatagg aacaatgttc aggtggcttc tctcctgtca     1020
gactttctgg gtaaacacgg tctggatcaa tga                                  1053

<210> SEQ ID NO 66
<211> LENGTH: 1053
<212> TYPE: DNA
<213> ORGANISM: Artificial Sequence
<220> FEATURE:
<223> OTHER INFORMATION: the ALT04M3-02 nucleotide sequence encoding the
      amino acid sequence corresponding to the herbicide tolerant
      protein ALT04M3 and based on the maize codon usage bias

<400> SEQUENCE: 66
atgagcaaga ggaaggtggt tctggctgag caggggtcgt tctacattgg ggggcggact      60
gtgaccgggc ccggcaagtt cgacccatcg aagcctgtca ttcgggcgtc taacgagggc     120
gctacgttct acatcaacca gatgtacgtg aatttccagg ctcccgtccg cccaaggggc     180
ctcccactgg tgttctggca cggcggggc ctgacaggcc atatctggga gtccactcca     240
gatggccgcc cagggttcca gacactcttc gttcaggaca ggcacacagt gtacactatt      300
gatcagccag ggaggggcag ggggaacatc cctaccttca atggcccatt cgggcagctg     360
gaggaggagt ccatcgtgaa caccgtcacg gcgaatgtga gcaaggagcg ggcttgggtc     420
agggaccggc tcgccccggc cccagggcag ttcttcgaga actctcagtt ccccgggc     480 tacgaggata attacttcaa ggagatgggc ttctcaccat ccatctcgtc tgacgagatt      540
gtcgatgccg tggtcaagct cgttacccac atcggcccct tgcgttctgg tacgcatagc      600
gcttcgggcg tcctcgggat gagggttgct acacatgcga agaacgttcg cggcatcgtg      660
gcttacgagc cggccacttc cattttcccc aagggcaagg tgccagagat cccaccactg      720
gccgacaaga agtcacagat cttcccacct ttcgagattc aggagtccta cttcaagaag      780
ctcgctaaga tccccattca gttcgtgttc ggcgacaaca ttcctaagaa tccgaagagc      840
gcgtactggt tcctggattg gtggcgcgtc acgcgctacg cgcactctct ctcactggag      900
gctatcaaca agctcggggg ccaggcctcg ctcctggacc tccctaccgc tggcctgagg      960
gggaacaccc atttcccgtt cacggatcgg aacaatgtcc aggttgcgtc cctcctgagc     1020
gatttcctcg gcaagcacgg gctggatcag tga                                  1053
```

```
<210> SEQ ID NO 67
<211> LENGTH: 29
<212> TYPE: DNA
<213> ORGANISM: Artificial Sequence
<220> FEATURE:
<223> OTHER INFORMATION: the primer 3 for PCR amplifcation of the
      ALT01M1 gene

<400> SEQUENCE: 67
tgcagacata tggaaaccga taaaaaaac                                         29

<210> SEQ ID NO 68
<211> LENGTH: 37
<212> TYPE: DNA
<213> ORGANISM: Artificial Sequence
<220> FEATURE:
<223> OTHER INFORMATION: the primer 4 for PCR amplifcation of the
      ALT01M1 gene

<400> SEQUENCE: 68
cccaagcttc tagctttcgt tctgatctaa gccgtgc                                37

<210> SEQ ID NO 69
<211> LENGTH: 1322
<212> TYPE: DNA
<213> ORGANISM: Arabidopsis thaliana

<400> SEQUENCE: 69
gtcgacctgc aggtcaacgg atcaggatat tcttgtttaa gatgttgaac tctatggagg       60
tttgtatgaa ctgatgatct aggaccggat aagttccctt cttcatagcg aacttattca      120
aagaatgttt tgtgtatcat tcttgttaca ttgttattaa tgaaaaaata ttattggtca      180
ttggactgaa cacgagtgtt aaatatggac caggccccaa ataagatcca ttgatatatg      240
aattaaataa caagaataaa tcgagtcacc aaaccacttg ccttttttaa cgagacttgt      300
tcaccaactt gatacaaaag tcattatcct atgcaaatca ataatcatac aaaaatatcc      360
aataacacta aaaattaaa agaaatggat aatttcacaa tatgttatac gataaagaag       420
ttacttttcc aagaaattca ctgattttat aagcccactt gcattagata atggcaaaa       480 aaaaacaaaa aggaaaagaa ataaagcacg aagaattcta gaaaatacga aatacgcttc      540
aatgcagtgg gacccacggt tcaattattg ccaattttca gctccaccgt atatttaaaa      600
aataaaacga taatgctaaa aaaatataaa tcgtaacgat cgttaaatct caacggctgg      660
atcttatgac gaccgttaga aattgtggtt gtcgacgagt cagtaataaa cggcgtcaaa      720
gtggttgcag ccggcacaca cgagtcgtgt ttatcaactc aaagcacaaa tactttttcct    780 caacctaaaa ataaggcaat tagccaaaaa caactttgcg tgtaaacaac gctcaataca      840
cgtgtcattt tattattagc tattgcttca ccgccttagc tttctcgtga cctagtcgtc      900
ctcgtctttt cttcttcttc ttctataaaa caatacccaa agcttcttct tcacaattca      960
gatttcaatt tctcaaaatc ttaaaaactt tctctcaatt ctctctaccg tgatcaaggt     1020
aaatttctgt gttccttatt ctctcaaaat cttcgatttt gttttcgttc gatcccaatt     1080
tcgtatatgt tctttggttt agattctgtt aatcttagat cgaagacgat tttctgggtt     1140
tgatcgttag atatcatctt aattctcgat tagggtttca taaatatcat ccgatttgtt     1200
caaataattt gagttttgtc gaataattac tcttcgattt gtgatttcta tctagatctg     1260
gtgttagttt ctagtttgtg cgatcgaatt tgtcgattaa tctgagtttt tctgattaac     1320
ag                                                                   1322
```

<210> SEQ ID NO 70
<211> LENGTH: 253
<212> TYPE: DNA
<213> ORGANISM: Agrobacterium tumefaciens

<400> SEQUENCE: 70

| | | | | | |
|---|---|---|---|---|---|
| gatcgttcaa | acatttggca | ataaagtttc | ttaagattga | atcctgttgc | cggtcttgcg | 60 |
| atgattatca | tataatttct | gttgaattac | gttaagcatg | taataattaa | catgtaatgc | 120 |
| atgacgttat | ttatgagatg | ggttttatg | attagagtcc | cgcaattata | catttaatac | 180 |
| gcgatagaaa | acaaaatata | gcgcgcaaac | taggataaat | tatcgcgcgc | ggtgtcatct | 240 |
| atgttactag | atc | | | | | 253 |

<210> SEQ ID NO 71
<211> LENGTH: 1534
<212> TYPE: DNA
<213> ORGANISM: Brassica napus

<400> SEQUENCE: 71

| | | | | | |
|---|---|---|---|---|---|
| gattatgaca | ttgctcgtgg | aatgggacag | ttatggtatt | tttttgtaat | aaattgtttc | 60 |
| cattgtcatg | agattttgag | gttaatctat | gagacattga | atcacttagc | attagggatt | 120 |
| aagtagtcac | aaatcgcatt | caagaagctg | aagaacacgt | tatggtctaa | tggttgtgtc | 180 |
| tcttttattag | aaaatgttgg | tcagtagcta | tatgcactgt | ttctgtaaaa | ccatgttggt | 240 |
| gttgtgttta | tttcaagaca | catgttgagt | ccgttgattc | agagcttttg | tcttcgaaca | 300 |
| caatctagag | agcaaatttg | ggttcaattt | ggatatcaat | atgggttcga | ttcagataga | 360 |
| acaatacccct | ttgatgtcgg | gtttcgattt | ggttgagatt | cattttttatc | gggtttggtt | 420 |
| cgattttcga | attcggttta | ttcgcccccct | catagcatct | acattctgca | gattaatgta | 480 |
| caagttatgg | aaaaaaaaat | gtggttttcg | aattcggttt | agtagctaaa | cgttgcttgc | 540 |
| agtgtagtta | tgggaattat | gaaacacgac | cgaaggtatc | aattagaaga | acgggtcaac | 600 |
| gggtaagtat | tgagaaatta | ccggagggta | aaaataaaca | gtattctttt | tttttcttaa | 660 |
| cgaccgacca | aggttaaaaa | aagaaaggag | gacgagatac | aggggcatga | ctgtaattgt | 720 |
| acataagatc | tgatctttaa | accctaggtt | tccttcgcat | cagcaactat | aaataattct | 780 |
| gagtgccact | cttcttcatt | cctagatctt | tcgccttatc | gctttagctg | aggtaagcct | 840 |
| ttctatacgc | atagacgctc | tcttttctct | tctctcgatc | ttcgttgaaa | cggtcctcga | 900 |
| tacgcatagg | atcggttaga | atcgttaatc | tatcgtctta | gatcttcttg | attgttgaat | 960 |
| tgagcttcta | ggatgtattg | tatcatgtga | tggatagttg | attggatctc | tttgagtgaa | 1020 |
| ctagctagct | ttcgatgcgt | gtgatttcag | tataacagga | tccgatgaat | tatagctcgc | 1080 |
| ttacaattaa | tctctgcaga | tttattgttt | aatcttggat | ttgatgctcg | ttgttgatag | 1140 |
| aggatcgttt | atagaactta | ttgattcgg | aattgagctt | gtgtgatgta | ttgtatcatg | 1200 |
| tgatcgatag | ctgatggatc | tatttgagtg | aactagcgta | cgatcttaag | atgagtgtgt | 1260 |
| attgtgaact | gatgattcga | gatcagcaaa | acaagatctg | atgatatctt | cgtcttgtat | 1320 |
| gcatcttgaa | tttcatgatt | ttttattaat | tatagctcgc | ttagctcaaa | ggatagagca | 1380 |
| ccacaaaatt | ttattgtggt | agaaatcggt | tcgattccga | tagcagctta | ctgtgatgaa | 1440 |
| tgattttgag | atttggtatt | tgatatatgt | ctactgtgtt | gaatgatcgt | ttatgcattg | 1500 |
| tttaatcgct | gcagatttgc | attgacaagt | agcc | | | 1534 |

<210> SEQ ID NO 72
<211> LENGTH: 228
<212> TYPE: DNA
<213> ORGANISM: Arabidopsis thaliana

<400> SEQUENCE: 72

| | |
|---|---:|
| atggcgcaag ttagcagaat ctgcaatggt gtgcagaacc catctcttat ctccaatctc | 60 |
| tcgaaatcca gtcaacgcaa atctccctta tcggtttctc tgaagacgca gcagcatcca | 120 |
| cgagcttatc cgatttcgtc gtcgtgggga ttgaagaaga gtgggatgac gttaattggc | 180 |
| tctgagcttc gtcctcttaa ggtcatgtct tctgtttcca cggcgtgc | 228 |

<210> SEQ ID NO 73
<211> LENGTH: 1368
<212> TYPE: DNA
<213> ORGANISM: Artificial Sequence
<220> FEATURE:
<223> OTHER INFORMATION: EPSPS: the 5-enolpyruvylshikimate-3-phosphate
      synthase gene

<400> SEQUENCE: 73

| | |
|---|---:|
| atgcttcacg gtgcaagcag ccggcccgca accgcccgca atcctctgg cctttccgga | 60 |
| accgtccgca ttcccggcga caagtcgatc tcccaccggt ccttcatgtt cggcggtctc | 120 |
| gcgagcggtg aaacgcgcat caccggcctt ctggaaggcg aggacgtcat caatacgggc | 180 |
| aaggccatgc aggcgatggg cgcccgcatc cgtaaggaag cgacacctg gatcatcgat | 240 |
| ggcgtcggca atggcggcct cctggcgcct gaggcgccgc tcgatttcgg caatgccgcc | 300 |
| acgggctgcc gcctgacgat gggcctcgtc ggggtctacg atttcgacag caccttcatc | 360 |
| ggcgacgcct cgctcacaaa gcgcccgatg gccgcgtgt tgaacccgct gcgcgaaatg | 420 |
| ggcgtgcagg tgaaatcgga agacggtgac cgtcttcccg ttaccttgcg cgggccgaag | 480 |
| acgccgacgc cgatcaccta ccgcgtgccg atggcctccg cacaggtgaa gtccgccgtg | 540 |
| ctgctcgccg gcctcaacac gcccggcatc acgacggtca tcgagccgat catgacgcgc | 600 |
| gatcatacgg aaaagatgct gcagggcttt ggcgccaacc ttaccgtcga cggatgcg | 660 |
| gacggcgtgc gcaccatccg cctggaaggc gcgggcaagc tcaccggcca agtcatcgac | 720 |
| gtgccgggcg accgtcctc gacggccttc ccgctggttg cggccctgct tgttccgggc | 780 |
| tccgacgtca ccatcctcaa cgtgctgatg aaccccaccc gcaccggcct catcctgacg | 840 |
| ctgcaggaaa tgggcgccga catcgaagtc atcaacccgc gccttgccgg cggcgaagac | 900 |
| gtggcggacc tgcgcgttcg ctcctccacg ctgaagggcg tcacggtgcc ggaagaccgc | 960 |
| gcgccttcga tgatcgacga atatccgatt ctcgctgtcg ccgccgcctt cgcggaaggg | 1020 |
| gcgaccgtga tgaacggtct ggaagaactc cgcgtcaagg aaagcgaccg cctctcggcc | 1080 |
| gtcgccaatg gcctcaagct caatggcgtg gattgcgatg agggcgagac gtcgctcgtc | 1140 |
| gtgcgtggcc gccctgacgg caaggggctc ggcaacgcct cgggcgccgc cgtcgccacc | 1200 |
| catctcgatc accgcatcgc catgagcttc ctcgtcatgg gcctcgtgtc ggaaaaccct | 1260 |
| gtcacggtgg acgatgccac gatgatcgcc acgagcttcc cggagttcat ggacctgatg | 1320 |
| gccgggctgg gcgcgaagat cgaactctcc gatacgaagg ctgcctga | 1368 |

<210> SEQ ID NO 74
<211> LENGTH: 643
<212> TYPE: DNA
<213> ORGANISM: Pisum sativum

<400> SEQUENCE: 74

```
agctttcgtt cgtatcatcg gtttcgacaa cgttcgtcaa gttcaatgca tcagtttcat    60
tgcgcacaca ccagaatcct actgagtttg agtattatgg cattgggaaa actgtttttc   120
ttgtaccatt tgttgtgctt gtaatttact gtgttttttta ttcggttttc gctatcgaac   180
tgtgaaatgg aaatggatgg agaagagtta atgaatgata tggtcctttt gttcattctc   240
aaattaatat tatttgtttt ttctcttatt tgttgtgtgt tgaatttgaa attataagag   300
atatgcaaac attttgtttt gagtaaaaat gtgtcaaatc gtggcctcta atgaccgaag   360
ttaatatgag gagtaaaaca cttgtagttg taccattatg cttattcact aggcaacaaa   420
tatattttca gacctagaaa agctgcaaat gttactgaat acaagtatgt cctcttgtgt   480
tttagacatt tatgaacttt cctttatgta attttccaga atccttgtca gattctaatc   540
attgctttat aattatagtt atactcatgg atttgtagtt gagtatgaaa atatttttta   600
atgcatttta tgacttgcca attgattgac aacatgcatc aat                     643

<210> SEQ ID NO 75
<211> LENGTH: 25
<212> TYPE: DNA
<213> ORGANISM: Artificial Sequence
<220> FEATURE:
<223> OTHER INFORMATION: the primer 5 for detecting the EPSPS gene
      sequence

<400> SEQUENCE: 75
ctggaaggcg aggacgtcat caata                                          25

<210> SEQ ID NO 76
<211> LENGTH: 22
<212> TYPE: DNA
<213> ORGANISM: Artificial Sequence
<220> FEATURE:
<223> OTHER INFORMATION: the primer 6 for detecting the EPSPS gene
      sequence

<400> SEQUENCE: 76
tggcggcatt gccgaaatcg ag                                             22

<210> SEQ ID NO 77
<211> LENGTH: 28
<212> TYPE: DNA
<213> ORGANISM: Artificial Sequence
<220> FEATURE:
<223> OTHER INFORMATION: the probe 1 for detecting the EPSPS gene
      sequence

<400> SEQUENCE: 77
atgcaggcga tgggcgcccg catccgta                                       28

<210> SEQ ID NO 78
<211> LENGTH: 1992
<212> TYPE: DNA
<213> ORGANISM: Zea mays

<400> SEQUENCE: 78
ctgcagtgca gcgtgacccg gtcgtgcccc tctctagaga taatgagcat tgcatgtcta    60
agttataaaa aattaccaca tattttttttt gtcacacttg tttgaagtgc agtttatcta   120
tctttataca tatatttaaa ctttactcta cgaataatat aatctatagt actacaataa   180
tatcagtgtt ttagagaatc atataaatga acagttagac atggtctaaa ggacaattga   240
gtattttgac aacaggactc tacagtttta tcttttttagt gtgcatgtgt tctccttttt   300
```

-continued

```
ttttgcaaat agcttcacct atataatact tcatccattt tattagtaca tccatttagg      360
gtttagggtt aatggttttt atagactaat ttttttagta catctatttt attctatttt      420
agcctctaaa ttaagaaaac taaaactcta ttttagtttt tttatttaat aatttagata      480
taaaatagaa taaaataaag tgactaaaaa ttaaacaaat accctttaag aaattaaaaa      540
aactaaggaa acattttttct tgtttcgagt agataatgcc agcctgttaa acgccgtcga     600
cgagtctaac ggacaccaac cagcgaacca gcagcgtcgc gtcgggccaa gcgaagcaga      660
cggcacggca tctctgtcgc tgcctctgga cccctctcga gagttccgct ccaccgttgg      720
acttgctccg ctgtcggcat ccagaaattg cgtggcggag cggcagacgt gagccggcac      780
ggcaggcggc ctcctcctcc tctcacggca cggcagctac gggggattcc tttcccaccg      840
ctccttcgct ttcccttcct cgcccgccgt aataaataga cacccctcc acccctctt      900 tccccaacct cgtgttgttc ggagcgcaca cacacacaac cagatctccc ccaaatccac      960
ccgtcggcac ctccgcttca aggtacgccg ctcgtcctcc ccccccccc ctctctacct     1020 tctctagatc ggcgttccgg tccatggtta gggcccggta gttctacttc tgttcatgtt     1080
tgtgttagat ccgtgtttgt gttagatccg tgctgctagc gttcgtacac ggatgcgacc     1140
tgtacgtcag acacgttctg attgctaact tgccagtgtt tctctttggg gaatcctggg     1200
atggctctag ccgttccgca gacgggatcg atttcatgat ttttttttgtt tcgttgcata    1260 gggtttggtt tgcccttttc ctttatttca atatatgccg tgcacttgtt tgtcgggtca    1320
tcttttcatg ctttttttttg tcttggttgt gatgatgtgg tctggttggg cggtcgttct   1380
agatcggagt agaattctgt tcaaactac ctggtggatt tattaattt ggatctgtat     1440 gtgtgtgcca tacatattca tagttacgaa ttgaagatga tggatggaaa tatcgatcta    1500
ggataggtat acatgttgat gcgggtttta ctgatgcata tacagagatg cttttttgttc   1560 gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtacatg      1740 ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttttag ccctgccttc    1920 atacgctatt tatttgcttg gtactgtttc ttttgtcgat gctcaccctg ttgtttggtg    1980
ttacttctgc ag                                                         1992
```

<210> SEQ ID NO 79
<211> LENGTH: 1176
<212> TYPE: DNA
<213> ORGANISM: Escherichia coli

<400> SEQUENCE: 79

```
atgcaaaaac tcattaactc agtgcaaaac tatgcctggg gcagcaaaac ggcgttgact        60
gaactttatg gtatggaaaa tccgtccagc cagccgatgg ccgagctgtg gatgggcgca      120
catccgaaaa gcagttcacg agtgcagaat gccgccggag atatcgtttc actgcgtgat      180
gtgattgaga gtgataaatc gactctgctc ggagaggccg ttgccaaacg ctttggcgaa      240 ctgccttttcc tgttcaaagt attatgcgca gcacagccac tctccattca ggttcatcca      300
aacaaacaca attctgaaat cggttttgcc aaagaaaatg ccgcaggtat cccgatggat     360
```

```
gccgccgagc gtaactataa agatcctaac cacaagccgg agctggtttt tgcgctgacg    420
cctttccttg cgatgaacgc gtttcgtgaa ttttccgaga ttgtctccct actccagccg    480
gtcgcaggtg cacatccggc gattgctcac tttttacaac agcctgatgc cgaacgttta    540
agcgaactgt tcgccagcct gttgaatatg cagggtgaag aaaaatcccg cgcgctggcg    600 atttttaaaat cggccctcga tagccagcag ggtgaaccgt ggcaaacgat tcgtttaatt   660
tctgaatttt acccggaaga cagcggtctg ttctccccgc tattgctgaa tgtggtgaaa    720
ttgaaccctg gcgaagcgat gttcctgttc gctgaaacac cgcacgctta cctgcaaggc    780
gtggcgctgg aagtgatggc aaactccgat aacgtgctgc gtgcgggtct gacgcctaaa    840
tacattgata ttccggaact ggttgccaat gtgaaattcg aagccaaacc ggctaaccag    900
ttgttgaccc agccggtgaa acaaggtgca gaactggact tcccgattcc agtggatgat    960
tttgccttct cgctgcatga ccttagtgat aaagaaacca ccattagcca gcagagtgcc   1020
gccattttgt tctgcgtcga aggcgatgca acgttgtgga aggttctca gcagttacag    1080 cttaaaccgg gtgaatcagc gtttattgcc gccaacgaat caccggtgac tgtcaaaggc   1140
cacggccgtt tagcgcgtgt ttacaacaag ctgtaa                              1176

<210> SEQ ID NO 80
<211> LENGTH: 29
<212> TYPE: DNA
<213> ORGANISM: Artificial Sequence
<220> FEATURE:
<223> OTHER INFORMATION: the primer 7 for detecting the PMI gene
      sequence

<400> SEQUENCE: 80
gctgtaagag cttactgaaa aaattaaca                                       29

<210> SEQ ID NO 81
<211> LENGTH: 18
<212> TYPE: DNA
<213> ORGANISM: Artificial Sequence
<220> FEATURE:
<223> OTHER INFORMATION: the primer 8 for detecting the PMI gene
      sequence

<400> SEQUENCE: 81
cgatctgcag gtcgacgg                                                   18

<210> SEQ ID NO 82
<211> LENGTH: 27
<212> TYPE: DNA
<213> ORGANISM: Artificial Sequence
<220> FEATURE:
<223> OTHER INFORMATION: the probe 2 for detecting the PMI gene sequence

<400> SEQUENCE: 82
tctcttgcta agctgggagc tcgatcc                                         27
```

HERBICIDE TOLERANCE PROTEIN, ENCODING GENE THEREOF AND USE THEREOF

REFERENCE TO RELATED APPLICATIONS

This application is a U.S. national stage of PCT/CN2018/124916, filed Dec. 28, 2018, which claims priority to Chinese application No. 201810124124.9, filed Feb. 7, 2018, the entire content of both of which is incorporated herein by reference.

SEQUENCE LISTING

The instant application contains a Sequence Listing which has been submitted electronically as a file in ASCII format and is hereby incorporated by reference in its entirety. Said ASCII format file, created on Dec. 1, 2020, is named 2020-12-1_Sequence_listing_BDBC0001PA txt and is 144,324 bytes in size.

TECHNICAL FIELD

The present invention relates to a herbicide tolerant protein, a coding gene thereof and use thereof, and in particular to a sulfonylurea herbicide tolerant protein, a coding gene thereof and use thereof.

BACKGROUND

Weeds may exhaust valuable nutrients required by crops and other plants of interest in the soil rapidly. Currently, there are many types of herbicides used to control weeds, among which a particularly popular herbicide is glyphosate. Crops resistant to glyphosate have been developed, such as maize, soybean, cotton, sugar beet, wheat and rice. Therefore, glyphosate can be sprayed onto the field where glyphosate resistant crops are planted, so as to control weeds without significant damage to the crops.

Glyphosate has been widely used in the world for more than 20 years, resulting in an over-reliance on glyphosate and glyphosate tolerant crop technologies, as well as applying a high selection pressure to plants that are naturally more tolerant to glyphosate or have developed a glyphosate-resistant activity in wild weed species. It has been reported that a few weeds have developed resistance to glyphosate, including broad-leaved weeds and gramineous weeds, such as *Lolium rigidium, Lolium multiflorum, Eleusine indica Gaertn, Ambrosia artemisiifolia, Conyza canadensis, Conyza bonariensis* and *Plantago lanceolata*. Moreover, weeds that were not agricultural problems before the wide use of glyphosate tolerant crops have become prevalent gradually, and are difficult to control with glyphosate tolerant crops, wherein these weeds mainly appear together with (but not only with) difficult-to-control broad-leaved weeds, such as the *Amaranthus, Chenopodium, Taraxacum* and *Commelinaceae* species.

In areas where glyphosate resistant weeds or difficult-to-control weed species are present, growers can compensate for the weakness of glyphosate by tank mixing or alternating with other herbicides that can control the missed weeds, such as sulfonylurea herbicides. Sulfonylurea herbicides have become the third most popular herbicides after organophosphorus and acetamide herbicides, with global annual sales of more than $3 billion. The annual application area of sulfonylurea herbicides in our country has been more than 2 million hectares and still shows an expanding trend.

With the emergence of glyphosate resistant weeds and the expanding application of sulfonylurea herbicides, there is a need for more genes capable of degrading sulfonylurea herbicides and for introducing the genes into plants of interest that are sensitive to sulfonylurea herbicides so as to increase the tolerance of the plants to sulfonylurea herbicides.

SUMMARY OF THE INVENTION

The objective of the present invention is to provide a herbicide tolerant protein, a coding gene thereof and use thereof, wherein the herbicide tolerant protein is capable of better degrading sulfonylurea herbicides and making the plants into which the herbicide tolerant protein-coding gene is introduced have higher tolerance to sulfonylurea herbicides.

In order to achieve the above objective, the present invention provides a herbicide tolerant protein, comprising:
(a) a protein consisting of an amino acid sequence as shown in SEQ ID NO: 1, and at least having an alanine substitution at position 176 and/or a valine substitution at position 178 of SEQ ID NO: 1; or
(b) a protein consisting of an amino acid sequence as shown in SEQ ID NO: 19, and at least having an alanine substitution at position 140 and/or a valine substitution at position 142 of SEQ ID NO: 19; or
(c) a protein consisting of an amino acid sequence as shown in SEQ ID NO: 35, and at least having an alanine substitution at position 140 and/or a valine substitution at position 142 of SEQ ID NO: 35; or
(d) a protein consisting of an amino acid sequence as shown in SEQ ID NO: 51, and at least having an alanine substitution at position 131 and/or a valine substitution at position 133 of SEQ ID NO: 51; or
(e) a protein which is derived from (a) to (d) by substituting and/or deleting and/or adding one or more amino acids in the amino acid sequences of (a) to (d), and has thifensulfuron hydrolase activity.

Furthermore, said herbicide tolerant protein comprises:
(f) an amino acid sequence of (a), wherein the amino acid sequence of (a) also has an arginine substitution at position 80 and/or an alanine substitution at position 81 and/or an arginine substitution at position 182 of SEQ ID NO: 1; or
(g) an amino acid sequence of (b), wherein the amino acid sequence of (b) also has an arginine substitution at position 44 and/or an alanine substitution at position 45 and/or an arginine substitution at position 146 of SEQ ID NO: 19; or
(h) an amino acid sequence of (c), wherein the amino acid sequence of (c) also has an arginine substitution at position 44 and/or an alanine substitution at position 45 and/or an arginine substitution at position 146 of SEQ ID NO: 35; or
(i) an amino acid sequence of (d), wherein the amino acid sequence of (d) also has an arginine substitution at position 35 and/or an alanine substitution at position 36 and/or an arginine substitution at position 137 of SEQ ID NO: 51; or
(j) a protein which is derived from (a) to (d) by substituting and/or deleting and/or adding one or more amino acids in the amino acid sequences of (f) to (i), and has thifensulfuron hydrolase activity.

Furthermore, the herbicide tolerant protein comprises:
(k) a protein consisting of an amino acid sequence as shown in SEQ ID NO: 7, SEQ ID NO: 11 or SEQ ID NO: 15; or
(l) a protein consisting of an amino acid sequence as shown in SEQ ID NO: 23, SEQ ID NO: 27 or SEQ ID NO: 31; or
(m) a protein consisting of an amino acid sequence as shown in SEQ ID NO: 39, SEQ ID NO: 43 or SEQ ID NO: 47; or
(n) a protein consisting of an amino acid sequence as shown in SEQ ID NO: 55, SEQ ID NO: 59 or SEQ ID NO: 63.

In order to achieve the above objective, the present invention further provides a herbicide tolerant gene, comprising:
(o) a nucleotide sequence encoding the herbicide tolerant protein according to (a)-(n); or
(p) a nucleotide sequence as shown in SEQ ID NO: 8, 9, 10, 12, 13, 14, 16, 17 or 18; or
(q) a nucleotide sequence as shown in SEQ ID NO: 24, 25, 26, 28, 29, 30, 32, 33 or 34; or
(r) a nucleotide sequence as shown in SEQ ID NO: 40, 41, 42, 44, 45, 46, 48, 49 or 50.

In order to achieve the above objective, the present invention further provides an expression cassette, wherein the expression cassette comprises the herbicide tolerant gene under the regulation of an effectively linked regulatory sequence.

In order to achieve the above objective, the present invention further provides a recombinant vector containing the herbicide tolerant gene or the expression cassette.

In order to achieve the above objective, the present invention also provides a method for producing a herbicide tolerant protein, comprising:
obtaining a cell of a transgenic host organism containing the herbicide tolerant gene or the expression cassette;
cultivating the cell of the transgenic host organism under conditions allowing production of a herbicide tolerant protein; and
recovering the herbicide tolerant protein.

Further, the transgenic host organism comprises plants, animals, bacteria, yeasts, baculoviruses, nematodes, or algae.

In order to achieve the above objective, the present invention further provides a method for increasing herbicide tolerance ranges, comprising co-expressing the herbicide tolerant protein or the herbicide tolerant protein encoded by the expression cassette together with at least one second protein which is different from the herbicide tolerant protein or the herbicide tolerant protein encoded by the expression cassette in a plant.

Furthermore, the second protein is 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome-like proteins and/or protoporphyrinogen oxidase.

The expression of the herbicide tolerant protein of the present invention in a transgenic plant can be accompanied by the expression of one or more other herbicide (glyphosate or glufosinate) tolerant proteins. This co-expression of more than one herbicide tolerant protein in the same transgenic plant can be achieved by allowing the plant to comprise and express a desired gene through genetic engineering. In addition, a plant (the first parent) can express the herbicide tolerant protein of the present invention through genetic engineering manipulation, and a second plant (the second parent) can express other herbicide (glyphosate or glufosinate) tolerant proteins through genetic engineering manipulation. Progeny plants expressing all the genes introduced into the first parent and the second parent are obtained by hybridizing the first parent with the second parent.

In order to achieve the above objective, the present invention also provides a method for selecting transformed plant cells, comprising: transforming a plurality of plant cells with the herbicide tolerant gene or the expression cassette, and cultivating the cells under a concentration of herbicide allowing the growth of the transformed cells expressing the herbicide tolerant gene or the expression cassette, while killing the untransformed cells or inhibiting the growth of the untransformed cells, wherein the herbicide is a sulfonylurea herbicide.

In order to achieve the above objective, the present invention also provides a method for controlling weeds, comprising applying an effective dose of a sulfonylurea herbicide to a field for planting a target plant, the plant containing the herbicide tolerant gene or the expression cassette.

In order to achieve the above objective, the present invention also provides a method for protecting a plant from damages caused by sulfonylurea herbicides, comprising introducing the herbicide tolerant gene, the expression cassette or the recombinant vector into a plant to make the resultant plant produce a sufficient amount of herbicide tolerant proteins for protecting the plant from damages caused by sulfonylurea herbicides.

In order to achieve the above objective, the present invention also provides a method for controlling glyphosate resistant weeds in a field for a glyphosate tolerant plant, comprising applying an effective dose of a sulfonylurea herbicide to a field for planting a glyphosate tolerant plant, the glyphosate tolerant plant containing the herbicide tolerant gene or the expression cassette.

In order to achieve the above objective, the present invention also provides a method for imparting sulfonylurea herbicide tolerance to a plant, comprising introducing the herbicide tolerant gene, the expression cassette or the recombinant vector into the plant.

In order to achieve the above objective, the present invention also provides a method for producing a sulfonylurea herbicide tolerant plant, comprising introducing the herbicide tolerant gene, the expression cassette or the recombinant vector into the genome of the plant.

In order to achieve the above objective, the present invention also provides a method for cultivating a sulfonylurea herbicide tolerant plant, comprising:
planting at least one plant propagule, whose genome contains the herbicide tolerant gene or the expression cassette;
allowing the plant propagule to grow into a plant;
applying an effective dose of a sulfonylurea herbicide to a plant growth environment comprising at least the plant, and harvesting the plant which has reduced plant damage and/or an increased plant yield compared to other plants which do not contain the herbicide tolerant gene or the expression cassette.

Further, the plant is a monocotyledonous plant or a dicotyledonous plant.

Preferably, the plant is maize, soybean, *Arabidopsis thaliana*, cotton, rape, rice, sorghum, wheat, barley, millet, sugar cane or oat.

On the basis of the above-mentioned technical solution, the sulfonylurea herbicide is tribenuron-methyl, sulfometuron-methyl, halosulfuron-methyl, pyrazosulfuron-ethyl, thifensulfuron methyl, bensulfuron-methyl, metsulfuron-methyl, ethametsulfuron-methyl or chlorimuron-ethyl.

In order to achieve the above objective, the present invention also provides a planting system for controlling weed growth, comprising a sulfonylurea herbicide and a plant growth environment in which at least one target plant exists, wherein the plant contains the herbicide tolerant gene or the expression cassette.

In order to achieve the above objective, the present invention also provides a planting system for controlling glyphosate resistant weeds in a field of a glyphosate tolerant plant, comprising a sulfonylurea herbicide, a glyphosate herbicide and a field for planting at least one glyphosate tolerant plant, wherein the glyphosate tolerant plant contains the herbicide tolerant gene or the expression cassette.

Further, the plant is a monocotyledonous plant or a dicotyledonous plant.

Preferably, the plant is maize, soybean, *Arabidopsis thaliana*, cotton, rape, rice, sorghum, wheat, barley, millet, sugar cane or oat.

On the basis of the above-mentioned technical solution, the sulfonylurea herbicide is tribenuron-methyl, sulfometuron-methyl, halosulfuron-methyl, pyrazosulfuron-ethyl, thifensulfuron methyl, bensulfuron-methyl, metsulfuron-methyl, ethametsulfuron-methyl or chlorimuron-ethyl.

In order to achieve the above objective, the present invention also provides use of a herbicide tolerant protein for degrading sulfonylurea herbicides, wherein the herbicide tolerant protein comprises:

(1) a protein consisting of an amino acid sequence as shown in SEQ ID NO: 1, and at least having an alanine substitution at position 176 and/or a valine substitution at position 178 of SEQ ID NO: 1; or (2) a protein consisting of an amino acid sequence as shown in SEQ ID NO: 19, and at least having an alanine substitution at position 140 and/or a valine substitution at position 142 of SEQ ID NO: 19; or (3) a protein consisting of an amino acid sequence as shown in SEQ ID NO: 35, and at least having an alanine substitution at position 140 and/or a valine substitution at position 142 of SEQ ID NO: 35; or (4) a protein consisting of an amino acid sequence as shown in SEQ ID NO: 51, and at least having an alanine substitution at position 131 and/or a valine substitution at position 133 of SEQ ID NO: 51; or (5) a protein which is derived from (1) to (4) by substituting and/or deleting and/or adding one or more amino acids in the amino acid sequences of (1) to (4), and has thifensulfuron hydrolase activity.

Furthermore, said herbicide tolerant protein comprises:

(6) an amino acid sequence of (1), wherein the amino acid sequence of (1) has an arginine substitution at position 80 and/or an alanine substitution at position 81 and/or an arginine substitution at position 182 of SEQ ID NO: 1; or (7) an amino acid sequence of (2), wherein the amino acid sequence of (2) has an arginine substitution at position 44 and/or an alanine substitution at position 45 and/or an arginine substitution at position 146 of SEQ ID NO: 19; or (8) an amino acid sequence of (3), wherein the amino acid sequence of (3) has an arginine substitution at position 44 and/or an alanine substitution at position 45 and/or an arginine substitution at position 146 of SEQ ID NO: 35; or (9) an amino acid sequence of (4), wherein the amino acid sequence of (4) has an arginine substitution at position 35 and/or an alanine substitution at position 131 and/or a valine substitution at position 133 of SEQ ID NO: 51; or

(10) a protein which is derived from (6) to (9) by substituting and/or deleting and/or adding one or more amino acids in the amino acid sequences of (6) to (9), and has thifensulfuron hydrolase activity.

Furthermore, the herbicide tolerant protein comprises:

(11) a protein consisting of an amino acid sequence as shown in SEQ ID NO: 7, SEQ ID NO: 11 or SEQ ID NO: 15; or

(12) a protein consisting of an amino acid sequence as shown in SEQ ID NO: 23, SEQ ID NO: 27 or SEQ ID NO: 31; or

(13) a protein consisting of an amino acid sequence as shown in SEQ ID NO: 39, SEQ ID NO: 43 or SEQ ID NO: 47; or

(14) a protein consisting of an amino acid sequence as shown in SEQ ID NO: 55, SEQ ID NO: 59 or SEQ ID NO: 63.

Preferably, the sulfonylurea herbicide is tribenuron-methyl, sulfometuron methyl, halosulfuron-methyl, pyrazosulfuron-ethyl, thifensulfuron-methyl, bensulfuron-methyl, metsulfuron-methyl, ethametsulfuron-methyl or chlorimuron ethyl.

The sulfometuron-methyl in the present invention refers to methyl 2-(4,6-dimethylpyrimidin-2-ylcarbamoylaminosulfonyl)benzoate as a white solid. Commonly used dosage forms are 10% sulfometuron-methyl wettable powder and 10% sulfometuron-methyl suspension (also known as dry suspension). Commercial formulations of sulfometuron-methyl include, but are not limited to, Oust and Sencaojing.

The effective dose of sulfometuron-methyl according to the present invention is 9 to 120 g ai/ha, including 10-100 g ai/ha, 15-90 g ai/ha, 20-80 g ai/ha, 25-70 g ai/ha, 30-60 g ai/ha or 40-50 g ai/ha.

The tribenuron-methyl in the present invention refers to methyl 2-[N-(4-methoxy-6-methyl-1,3,5-triazin-2-yl)-N-methylcarbamoylaminosulfonyl]benzoate as a white solid. Commonly used dosage forms are 10% tribenuron-methyl wettable powder, and 75% tribenuron-methyl suspension (also known as dry suspension). Commercial formulations of tribenuron-methyl include, but are not limited to, GRANSTAR and kuoyejing.

The effective dose of tribenuron-methyl according to the present invention is 9 to 144 g ai/ha, including 15-120 g ai/ha, 30-110 g ai/ha, 40-100 g ai/ha, 50-90 g ai/ha, 60-80 g ai/ha or 65-75 g ai/ha.

The herbicide tolerant gene, the expression cassette or the recombinant vector according to the present invention is introduced into a plant. In order to introduce the exogenous DNA into plant cells in the present invention, the conventional transformation methods include, but are not limited to, the *Agrobacterium*-mediated transformation, microprojectile bombardment, the direct DNA uptake into the protoplast, electroporation or silicon whisker-mediated DNA introduction.

The herbicide tolerant gene and the subsequent herbicide resistant crop according to the present invention provide an excellent choice for controlling glyphosate-resistant (or highly tolerant and successive) broad-leaved weed species in the crop. The sulfonylurea herbicides have a broad spectrum and are potent herbicides for broad-leaved weeds, and would provide excellent utility for planters if the stronger crop tolerance could be provided in both dicotyledons and monocotyledons alike. A transgenic dicotyledonous plant with a tolerance to sulfonylurea herbicide also has higher flexibilities in the timing and amount of application. Another use of the sulfonylurea herbicide resistant trait is that it can be used for preventing normally sensitive crops from damage caused by the drifting, volatilization, conversion (or other movement over a long distance), misuse, destruction, etc., of the sulfonylurea herbicides. The use of the herbicide tolerant gene according to the present invention in a plant can provide protection against a broader spectrum of sulfonylurea herbicides, thereby improving the flexibility and spectra of weeds that can be controlled, and can provide protection against damage caused by the drifting of a full range of commercially available sulfonylurea herbicides or caused by other sulfonylurea herbicides over a long distance.

It has now been identified that the herbicide tolerant gene according to the present invention has the characteristic of allowing the use of sulfonylurea herbicides in plants after being genetically modified for the expression in the plants, wherein the absence or lack of inherent tolerance in the plants does not allow the use of these herbicides. In addition, the herbicide tolerant gene of the present invention can provide protection against the sulfonylurea herbicides in plants where the natural tolerance is insufficient for selectivity. At present, the plants containing only the herbicide tolerant gene of the present invention can be treated sequentially or tank-mixed with one, two or a combination of several sulfonylurea herbicides. The application amount of each sulfonylurea herbicide for controlling a broad spectrum of dicotyledonous weeds ranges from 7.5 to 150 g ai/ha, more generally from 20 to 50 g ai/ha. Use of the herbicides of different chemical categories and having different modes and ranges of actions in the same field in combination (sequentially or tank-mixed) can provide control for most potential weeds that need to be controlled by the herbicides.

Glyphosate is widely used, as it controls a very broad spectrum of broad-leaved and gramineous weed species. However, reusing glyphosate in glyphosate tolerant crops and non-crop applications has selected (and still will select) to make weeds evolve into naturally more tolerant species or glyphosate tolerant biotypes. Most herbicide tolerance management strategies suggest using an effective amount of tank-mixed herbicide partners as a means of delaying the emergence of tolerant weeds, wherein the herbicide partners provide control of the same species, but have different modes of action. Stacking the herbicide tolerant gene according to the present invention gene with a glyphosate tolerance trait (and/or another herbicide tolerance trait) can achieve control of glyphosate tolerant weed species (broad-leaved weed species controlled by one or more sulfonylurea herbicides) in glyphosate tolerant crops by allowing selective use of glyphosate and sulfonylurea herbicides in the same crop. The application of these herbicides can be performed by using simultaneously in a tank mixture containing two or more herbicides with different modes of action, or using a single herbicide composition alone in continuous use (e.g., before planting or before or after emergence) (with an interval time range used being from 2 hours to 3 months), or alternatively, can be performed by using a combination of any number of herbicides representative of each applicable compound category at any time (from any time within 7 months after planting a crop to the time when the crop is harvested (or the pre-harvest interval for a single herbicide, with the shortest being taken)).

The flexibility in controlling broad-leaved weeds is very important, i.e., application time, single application amount of herbicide, and abilities to control the stubborn or resistant weeds. The application range of glyphosate stacked with a glyphosate tolerant gene/the herbicide tolerant gene of the present invention in crops can be from 200 to 1600 g ai/ha; and that of (one or more) sulfonylurea herbicides can be from 7.5 to 150 g ai/ha. The optimal combination of time for these applications depends on the specific conditions, species and environments.

A herbicide preparation (e.g., an ester, acid or salt formula or soluble concentrate, emulsifying concentrate or soluble liquid) and a tank mix additive (e.g., an adjuvant or compatilizer) can significantly affect weed control of a given herbicide or a combination of one or more herbicides. Any chemical combination of any of the foregoing herbicides is within the scope of the present invention.

It is well known for a person skilled in the art that the benefits of a combination of two or more modes of action in improving the controlled spectrum of weed and/or naturally more tolerant species or resistant weed species can also be extended to artificial (transgenic or non-transgenic) production of herbicide tolerant chemicals in addition to glyphosate tolerant crops in crops. In fact, the traits encoding the following resistances can be stacked alone or in multiple combinations to provide the ability to effectively control or prevent weeds from developing tolerance to any of the above categories of herbicides: 5-enolpyruvylshikimate-3-phosphate synthase (EPSPS), glyphosate oxidoreductase (GOX), glyphosate-N-acetyltransferase (GAT), glyphosate decarboxylase, glufosinate acetyltransferase (PAT), α-ketoglutarate dependent dioxygenase (AAD), dicamba monooxygenase (DMO), 4-hydroxyphenylpyruvate dioxygenase (HPPD), acetolactate synthase (ALS), cytochrome-like proteins (P450) and/or protoporphyrinogen oxidase (Protox).

In addition, the herbicide tolerant gene of the present invention alone or the herbicide tolerant gene of the present invention stacked with other characteristics of herbicide tolerant crops can be stacked with one or more other input traits (for example, insect tolerance, fungal tolerance or stress tolerance) or output traits (for example, increased yield, improved oil amount or increased fiber quality). Therefore, the present invention can be used to provide the abilities to flexibly and economically control any number of agricultural pests and complete agricultural solutions for improving qualities of crops.

The herbicide tolerant gene of the present invention can degrade a sulfonylurea herbicide, and is an important basis of herbicide tolerant crops and the possibility for selecting marker features.

Transgenic expression can be performed in the present invention, and almost all combinations of herbicides for broad-leaved weeds can be controlled. The herbicide tolerant gene of the present invention as an excellent trait of herbicide tolerant crops can be stacked with, for example, other traits of herbicide tolerant crops (for example, glyphosate tolerance, glufosinate tolerance, tolerance to other ALS inhibitor (for example, imidazolinones and triazolopyrimidinyl sulfonamides), bromoxynil tolerance, HPPD inhibitor tolerance, PPO inhibitor tolerance, and the like) and traits of insect tolerance (Cry1Ab, Cry1F, Vip3, other *Bacillus thuringiensis* proteins or insect tolerant proteins derived from non-bacillus bacterial species, etc.). In addition, the herbicide tolerant gene of the present invention can be used as a selective marker for the assistant selection of primary transformants of plants genetically modified with another gene or gene group.

The traits of herbicide tolerant crops of the present invention can be used in a new combination with other traits (including but not limited to glyphosate tolerance) of herbicide tolerant crops. A new method for controlling the weed species can be produced by the combination of these traits due to newly obtained tolerance or inherent tolerance to a herbicide (for example, glyphosate). Therefore, apart from the traits of herbicide tolerant crops, the scope of the present invention includes the new method for controlling weeds with herbicides, wherein the tolerance to the herbicides can be produced by the enzyme in the transgenic crops.

The present invention can be applied to various types of plants, and the dicotyledonous plant includes, but is not limited to, alfalfa, beans, cauliflowers, cabbages, carrots, celery, cotton, cucumbers, eggplants, lettuces, melon, peas, peppers, zucchinis, radishes, rape, spinach, soybeans, pumpkins, tomatoes, *Arabidopsis thaliana* or watermelons; preferably, the dicotyledonous plant refers to soybeans, *Arabidopsis thaliana*, tobacco, cotton or rape. The monocotyledonous plant includes, but is not limited to, maize, rice, sorghum, wheat, barley, rye, millet, sugar cane, oats or turfgrass; preferably, the monocotyledonous plant refers to maize, rice, sorghum, wheat, barley, millet, sugar cane or oats. The herbicide tolerant gene according to the present invention can be more positively used in gramineous crops with moderate tolerance, and thus the improved tolerance obtained by such traits can provide planters with the possibility of using these herbicides with a more effective application amount and a broader application time without crop damage risks.

The planting system in the present invention refers to a combination of a plant and any herbicide tolerance thereof and/or an available herbicide treatment in different plant developmental stages, thus producing plants with high yields and/or reduced damage.

In the present invention, the weeds refer to plants competing with the cultivated target plants in the plant growth environment.

The term "control" and/or "prevention" in the present invention refers to at least a direct application (e.g., by spraying) of an effective dose of a sulfonylurea herbicide to the plant growth environment, so as to minimize weed development and/or stop weeds from growing. At the same time, the cultivated target plants should be morphologically normal and can be cultivated under conventional methods for product consumption and/or production; and preferably, compared to non-transgenic wild-type plants, the cultivated plants have reduced plant damage and/or an increased plant yield. The specific performances of the reduced plant damage include, but are not limited to, an improved stem resistance and/or an increased grain weight. The "control" and/or "prevention" effect of the herbicide tolerant protein of the present invention on weeds can exist independently, and will not be diminished and/or lost due to the presence of other substances that can "control" and/or "prevent" the weeds. Specifically, if any tissue of a transgenic plant (containing the herbicide tolerant gene of the present invention) has and/or produces the herbicide tolerant protein of the present invention and/or another substance that can control weeds simultaneously and/or separately, then the presence of the other substance will neither affect the "control" and/or "prevention" effect of the herbicide tolerant protein of the present invention on the weeds, nor result in that the "control" and/or "prevention" effect is achieved completely and/or partially by the other substance and has nothing to do with the herbicide tolerant protein of the present invention.

The genome of a plant, plant tissue or plant cell in the present invention refers to any genetic material within the plant, plant tissue or plant cell, and includes cell nuclear, plastid and mitochondrial genome.

The "plant propagule" in the present invention includes, but is not limited to, plant sexual propagules and plant vegetative propagules. The plant sexual propagules include, but are not limited to, plant seeds; and the plant vegetative propagules refer to vegetative organs or a specific tissue of a plant, which can generate a new plant under ex vivo conditions. The vegetative organs or the specific tissue include, but are not limited to, roots, stems and leaves; for example, plants with roots as the vegetative propagules include strawberries, sweet potatoes and the like; plants with stems as the vegetative propagules include sugar cane, potatoes (tubers) and the like; and plants with leaves as the vegetative propagules include aloe, begonias and the like.

The "resistance" in the present invention is heritable, and allows a plant to grow and propagate in the case where an effective treatment by a general herbicide is performed on a given plant. As recognized by a person skilled in the art, even if a certain damage degree of a plant treated with a herbicide is apparent, the plant can still be considered "resistant". The term "tolerance" in the present invention is more extensive than the term "resistance", and includes "resistance" and an improved ability of a particular plant to resist various degrees of damage induced by a herbicide, and generally, damages to a wild-type plant with the same genotype can be caused at the same herbicide dose.

The polynucleotide and/or nucleotide in the present invention form a complete "gene", which encodes a protein or a polypeptide in a desired host cell. A person skilled in the art will readily appreciate that the polynucleotide and/or nucleotide in the present invention can be placed under the control of a regulatory sequence in a host of interest.

As is well known to a person skilled in the art, DNA is typically present in a double-stranded form. In this arrangement, one strand is complementary to the other, and vice versa. Additional complementary strand of DNA is produced as DNA is replicated in a plant. As such, the present invention includes the use of the polynucleotides as exemplified in the sequence listing and complementary strands thereof. The "coding strand" commonly used in the art refers to a strand bound to an antisense strand. In order to express a protein in vivo, one strand of DNA is typically transcribed to one complementary strand of mRNA, which acts as a template for translating the protein. Actually, mRNA is transcribed from the "antisense" strand of DNA. The "sense" or "coding" strand has a series of codons (a codon is composed of three nucleotides, and a specific amino acid can be produced by reading three codons at a time), which can be read as an open reading frame (ORF) to form a protein or peptide of interest. The present invention also includes RNA having an equivalent function to the exemplary DNA.

The nucleic acid molecule or a fragment thereof in the present invention hybridizes with the herbicide tolerant gene of the present invention under stringent conditions. Any conventional nucleic acid hybridization or amplification method can be used to identify the presence of the herbicide tolerant gene of the present invention. A nucleic acid molecule or a fragment thereof is capable of specifically hybridizing with other nucleic acid molecules under certain circumstances. In the present invention, if two nucleic acid molecules can form an anti-parallel double stranded nucleic acid structure, then it can be considered that these two nucleic acid molecules can be specifically hybridized with each other. If two nucleic acid molecules exhibit a complete complementarity, then one nucleic acid molecule of the two is said to be the "complement" of the other nucleic acid molecule. In the present invention, when each nucleotide of a nucleic acid molecule is complementary to the corresponding nucleotide of another nucleic acid molecule, then these two nucleic acid molecules are said to exhibit a "complete complementarity". If two nucleic acid molecules can be hybridized with each other with a sufficient stability such that they are annealed and bound to each other at least under conventional "low stringency" conditions, then these two nucleic acid molecules are said to be "minimally complementary". Similarly, if two nucleic acid molecules can be hybridized with each other with a sufficient stability such that they are annealed and bound to each other under conventional "high stringency" conditions, then these two nucleic acid molecules are said to be "complementary". Deviation from a complete complementarity is permissible, as long as this deviation does not completely prevent two molecules from forming a double-stranded structure. In order to enable a nucleic acid molecule to act as a primer or probe, it is only necessary to ensure that the nucleic acid molecule has a sufficient complementarity in its sequence to allow a stable double-stranded structure to be formed in case of the particular solvent and salt concentration used.

In the present invention, a substantially homologous sequence is a nucleic acid molecule, wherein the nucleic acid molecule can be specifically hybridized with the complementary strand of a matched nucleic acid molecule under high stringency conditions. Suitable stringent conditions that promote DNA hybridization are well known to a person skilled in the art; for example, the suitable stringent conditions can be achieved by treating with 6.0× sodium chloride/sodium citrate (SSC) under conditions of approximately 45, and then washing with 2.0×SSC under conditions of 50. For example, the salt concentration in the washing step can be selected from the low stringency condition of about 2.0×SSC and 50° C. to the high stringency condition of about 0.2×SSC and 50° C. In addition, the temperature condition in the washing step can rise from the low stringency condition of room temperature (about 22° C.) to the high stringency condition of about 65° C. The temperature condition and the salt concentration can both vary, and it is also possible that one of the two remains unchanged, while the other variable varies. Preferably, the stringent conditions in the present invention can be achieved by specifically hybridizing a sequence with the herbicide tolerant gene in the present invention in a 6×SSC, 0.5% SDS solution at 65° C., and then washing the membrane once with 2×SSC, 0.1% SDS and once with 1×SSC, 0.1% SDS.

Consequently, sequences which have the herbicide tolerant activity and are hybridized with the herbicide tolerant gene of the present invention under stringent conditions are included in the present invention. These sequences are at least approximately 40%-50% homologous, or approximately 60%, 65% or 70% homologous, or even at least approximately 75%, 80%, 85%, 90%, 91%, 92%, 93%, 94%, 95%, 96%, 97%, 98%, 99% or more to the sequence of the present invention.

The present invention provides a functional protein. In the present invention, the "functional activity" (or "activity") means that the protein/enzyme used in the present invention (alone or in combination with other proteins) has the ability to degrade a sulfonylurea herbicide or diminish the activity of a sulfonylurea herbicide. A plant producing the herbicide tolerant protein of the present invention preferably produces an "effective amount" of the protein, so that when the plant is treated with a herbicide, the protein expression level is sufficient to impart to the plant a complete or partial resistance or tolerance to the sulfonylurea herbicide (unless otherwise specified, in a general amount). The herbicide can be used in an amount which would usually kill a target plant or in a normal field amount and concentration. Preferably, the plant cell and plant of the present invention are protected from growth inhibition or damage caused by treatment with the herbicide. The transformed plant and plant cell of the present invention preferably has tolerance or resistance to sulfonylurea herbicides; that is, the transformed plant and plant cell can grow in the presence of an effective amount of sulfonylurea herbicides.

The gene and protein in the present invention not only comprise a specific exemplary sequence, but also comprise a portion and/or a fragment (including an internal deletion and/or terminal deletion compared to the full-length protein), a variant, a mutant, a substitute (a protein having substituted amino acids), a chimera and a fusion protein, which retain the herbicide tolerance activity characteristic of the specific exemplary protein. The "variant" or "variation" refers to a nucleotide sequence that encodes the same protein or encodes an equivalent protein having a herbicide resistance activity. The "equivalent protein" refers to a protein having the same or substantially the same bioactivity of herbicide tolerance as the claimed protein.

The "fragment" or "truncation" of a DNA molecule or protein sequence in the present invention refers to a portion of the original DNA or protein sequence (nucleotides or amino acids) or an artificially modified form thereof (e.g., a sequence suitable for plant expression), wherein the length of the foregoing sequences may vary, but the length is sufficient to ensure that the (encoded) protein is a herbicide tolerant protein.

Because of the degeneracy of the genetic codon, a variety of different DNA sequences may encode the same amino acid sequence. It is within the skill of a person skilled in the art to produce these alternative DNA sequences encoding the same or substantially the same protein. These different DNA sequences are included in the scope of the present invention. The aforementioned "substantially the same" sequence refers to a sequence with an amino acid substitution, deletion, addition or insertion that does not substantively affect the herbicide tolerance activity, and includes a fragment retaining the herbicide tolerance activity.

The substitution, deletion or addition of an amino acid sequence in the present invention is a conventional technique in the art. Preferably, this amino acid change is a small characteristic change, that is, a conservative amino acid substitution that does not significantly affect the folding and/or activity of a protein; a small deletion, typically a deletion of about 1-30 amino acids; a small amino or carboxyl terminal extension, e.g., a methionine residue extending at the amino terminus; or a small linker peptide, e.g., about 20-25 residues in length.

Examples of conservative substitutions are substitutions occurring within the following amino acid groups: basic amino acids (e.g., arginine, lysine and histidine), acidic amino acids (e.g., glutamic acid and aspartic acid), polar amino acids (e.g., glutamine and asparagine), hydrophobic amino acids (e.g., leucine, isoleucine and valine), aromatic amino acids (e.g., phenylalanine, tryptophan and tyrosine) and small molecule amino acids (e.g., glycine, alanine, serine, threonine and methionine). Those amino acid substitutions that generally do not alter the specific activity are well known in the art, and have been described by, for example, N. Neurath and R. L. Hill in *Protein*, published by Academic Press in New York in 1979. The most common substitutions are Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, as well as the reverse substitutions thereof.

As will be apparent to a person skilled in the art, this substitution can occur outside the region that is important for molecular functions, and still produces an active polypeptide. Amino acid residues that are essential for the activity of the polypeptide of the present invention and are thus chosen not to be substituted can be identified according to methods known in the art, such as site-directed mutagenesis or alanine-scanning mutagenesis (see e.g., Cunningham and Wells, 1989, Science 244: 1081-1085). The latter technique is to introduce a mutation at each positively charged residue in a molecule and detect the herbicide resistance activity of the resulting mutant molecule to determine the amino acid residues that are important for the molecular activity. Substrate-enzyme interaction sites can also be determined by analyzing the three-dimensional structure thereof, wherein this three-dimensional structure can be determined by nuclear magnetic resonance analysis, crystallography, photoaffinity labeling and other techniques (see e.g., de Vos et al., 1992, Science 255: 306-312; Smith et al., 1992, J. Mol. Biol. 224: 899-904; and Wlodaver et al., 1992, FEBS Letters 309: 59-64).

The regulatory sequence in the present invention includes, but is not limited to, a promoter, a transit peptide, a terminator, an enhancer, a leader sequence, an intron and other regulatory sequences operably linked to the herbicide tolerant gene of the present invention.

The promoter is a plant expressible promoter. The "plant expressible promoter" refers to a promoter that ensures the expression of the coding sequence linked thereto in a plant cell. The plant expressible promoter can be a constitutive promoter. Examples of the promoters directing the constitutive expression in plants include, but are not limited to, a 35S promoter derived from a cauliflower mosaic virus, maize Ubi promoters, rice GOS2 gene promoters, and the like. Alternatively, the plant expressible promoter can be a tissue specific promoter; i.e. the promoter directs the expression of a coding sequence in several tissues, such as green tissues, at a level higher than in other tissues of the plant (which can be measured through conventional RNA trials), such as a PEP carboxylase promoter. Alternatively, the plant expressible promoter can be a wound-inducible promoter. The wound-inducible promoter or a promoter directing a wound-induced expression pattern means that when a plant suffers from a wound caused by a mechanical factor or the gnawing of insects, the expression of the coding sequence under the regulation of the promoter is significantly improved compared to normal growth conditions. Examples of the wound-inducible promoters include, but are not limited to, promoters of potato and tomato protease inhibitor genes (pin I and pin II) and a maize protease inhibitor gene (MPI).

The transit peptide (also known as secretion signal sequence or targeting sequence) directs a transgenic product to a specific organelle or cell compartment. For a receptor protein, the transit peptide may be heterologous, for example, targeting the chloroplast using a sequence encoding the chloroplast transit peptide, or targeting the endoplasmic reticulum using a 'KDEL' retention sequence, or targeting the vacuole using CTPP of a barley phytolectin gene.

The leader sequence includes, but is not limited to, a small RNA virus leader sequence, such as an EMCV leader sequence (a 5' non-coding region of encephalomyocarditis virus); a potato virus Y group leader sequence, such as a MDMV (Maize Dwarf Mosaic Virus) leader sequence; human immunoglobulin heavy chain binding protein (BiP); an untranslated leader sequence of the coat protein mRNA of alfalfa mosaic virus (AMV RNA4); and a tobacco mosaic virus (TMV) leader sequence.

The enhancer includes, but is not limited to, a cauliflower mosaic virus (CaMV) enhancer, figwort mosaic virus (FMV) enhancer, carnation etched ring virus (CERV) enhancer, cassava vein mosaic virus (CsVMV) enhancer, mirabilis mosaic virus (MMV) enhancer, cestrum yellow leaf curling virus (CmYLCV) enhancer, cotton leaf curl Multan virus (CLCuMV) enhancer, commelina yellow mottle virus (CoYMV) enhancer and peanut chlorotic streak virus (PCLSV) enhancer.

For use in a monocotyledonous plant, the intron includes, but is not limited to, a maize hsp70 intron, maize ubiquitin intron, Adh intron 1, sucrose synthase intron or rice Actl intron. For use in a dicotyledonous plant, the intron includes, but is not limited to, a CAT-1 intron, pKANNIBAL intron, PIV2 intron and "super ubiquitin" intron.

The terminator can be a suitable polyadenylation signal sequence that functions in a plant, including, but not limited to, a polyadenylation signal sequence derived from the *Agrobacterium tumefaciens* nopaline synthetase (NOS) gene, a polyadenylation signal sequence derived from the protease inhibitor II (pinII) gene, a polyadenylation signal sequence derived from the pea ssRUBISCO E9 gene and a polyadenylation signal sequence derived from the α-tubulin gene.

The "effective linking" in the present invention indicates the binding of nucleic acid sequences, wherein the binding enables a sequence to provide a function required for the sequence linked thereto. The "effective linking" in the present invention can be achieved by linking a promoter to a sequence of interest, so that the transcription of the sequence of interest is controlled and regulated by the promoter. When a sequence of interest encodes a protein and the expression of the protein is desired, "effective linking" means that a promoter is linked to the sequence in such a manner that the resulting transcript is efficiently translated. If the linking of a promoter to a coding sequence is a transcript fusion and expression of the encoded protein is intended to be achieved, such linking is created that the first translation initiation codon in the resulting transcript is the initiation codon in the coding sequence. Alternatively, if the linking of a promoter to a coding sequence is a translation fusion and expression of the encoded protein is intended to be achieved, such a linking is created that the first translation initiation codon contained in the 5' untranslated sequence is linked to the promoter in such a manner that the relationship of the resulting translation product with the translation open reading frame encoding the desired protein is in-frame. Nucleic acid sequences that can be "effectively linked" include, but are not limited to: sequences providing gene expression functions (i.e., gene expression elements, such as promoters, 5' untranslated regions, introns, protein coding regions, 3' untranslated regions, polyadenylation sites and/or transcription terminators), sequences providing DNA transfer and/or integration functions (i.e., T-DNA boundary sequences, site-specific recombinase recognition sites and integrase recognition sites), sequences providing selective functions (i.e., antibiotic resistance markers and biosynthesis genes), sequences providing marker scoring functions, sequences assisting in sequence manipulation in vitro or in vivo (i.e., polylinker sequences and site-specific recombination sequences) and sequences providing replication functions (i.e., bacterial origins of replication, autonomously replicating sequences and centromeric sequences).

The present invention may impart a new herbicide resistance trait to a plant, and no adverse effects on phenotypes (including yields) are observed. The plant in the present invention can tolerate, e.g., 2×, 3×, 4× or 8× the general application level of at least one herbicide tested. The improvement of these levels of tolerance is within the scope of the present invention. For example, foreseeable optimization and further development can be performed on various techniques known in the art, to increase the expression of a given gene.

The herbicide tolerant protein of the present invention can be a protein consisting of an amino acid sequence shown in SEQ ID NO: 1 and at least having an alanine substitution at position 176 and/or a valine substitution at position 178 of SEQ ID NO: 1, with an example shown in SEQ ID NO: 7, SEQ ID NO: 11 or SEQ ID NO: 15 in the sequence listing. The herbicide tolerant gene of the present invention can be a coding gene of the above-mentioned herbicide tolerant protein, with examples shown in SEQ ID NOs: 8-10, SEQ ID NOs: 12-14 and SEQ ID NOs: 16-18 in the sequence listing.

The herbicide tolerant protein of the present invention can be a protein consisting of an amino acid sequence shown in SEQ ID NO: 19 and at least having an alanine substitution at position 140 and/or a valine substitution at position 142 of SEQ ID NO: 19, with an example shown in SEQ ID NO: 23, SEQ ID NO: 27 or SEQ ID NO: 31 in the sequence listing. The herbicide tolerant gene of the present invention can be a coding gene of the above-mentioned herbicide tolerant protein, with examples shown in SEQ ID NOs: 24-26, SEQ ID NOs: 28-30 and SEQ ID NOs: 32-34 in the sequence listing.

The herbicide tolerant protein of the present invention can be a protein consisting of an amino acid sequence shown in SEQ ID NO: 35 and at least having an alanine substitution at position 140 and/or a valine substitution at position 142 of SEQ ID NO: 35, with an example shown in SEQ ID NO: 39, SEQ ID NO: 43 or SEQ ID NO: 47 in the sequence listing. The herbicide tolerant gene of the present invention can be a coding gene of the above-mentioned herbicide tolerant protein, with examples shown in SEQ ID NOs: 40-42, SEQ ID NOs: 44-46 and SEQ ID NOs: 48-50 in the sequence listing.

The herbicide tolerant protein of the present invention can be a protein consisting of an amino acid sequence shown in SEQ ID NO: 51 and at least having an alanine substitution at position 131 and/or a valine substitution at position 133 of SEQ ID NO: 51, with an example shown in SEQ ID NO: 55, SEQ ID NO: 59 or SEQ ID NO: 63 in the sequence listing. The herbicide tolerant gene of the present invention can be a coding gene of the above-mentioned herbicide tolerant protein, with examples shown in SEQ ID NOs: 56-58, SEQ ID NOs: 60-62 and SEQ ID NOs: 64-66 in the sequence listing.

The herbicide tolerant gene of the present invention can be used in plants; and can contain, apart from a coding region of the herbicide tolerant gene of the present invention, other elements such as a coding region encoding a transit peptide, and a coding region encoding a selective marker protein or a protein imparting insect resistance.

The herbicide tolerant protein of the present invention has tolerance to most of the sulfonylurea herbicides. The plant in the present invention contains an exogenous DNA in its genome, wherein the exogenous DNA comprises the herbicide tolerant gene of the present invention, and the plant is protected from the threat of a sulfonylurea herbicide by expressing an effective amount of the protein. The effective amount refers to a dose causing no or minor damage. At the same time, the plant should be morphologically normal and can be cultivated under conventional methods for product consumption and/or production.

The expression level of the herbicide tolerant protein in a plant material can be detected by a variety of methods described in the art, for example, by quantifying the mRNA encoding the herbicide tolerant protein produced in a tissue by employing specific primers, or specifically detecting the amount of the produced herbicide tolerant protein directly.

The present invention provides a herbicide tolerant protein, a coding gene thereof and a use thereof, having the following advantages:

1. The herbicide tolerant protein of the present invention has a strong tolerance to sulfonylurea herbicides and can tolerate eight-fold field concentration of tribenuron-methyl.
2. The herbicide tolerant protein of the present invention has a broad prospect of application in plants.

The technical solution of the present invention is further described in details through the figures and examples below.

PARTICULAR EMBODIMENTS

Figure 1:
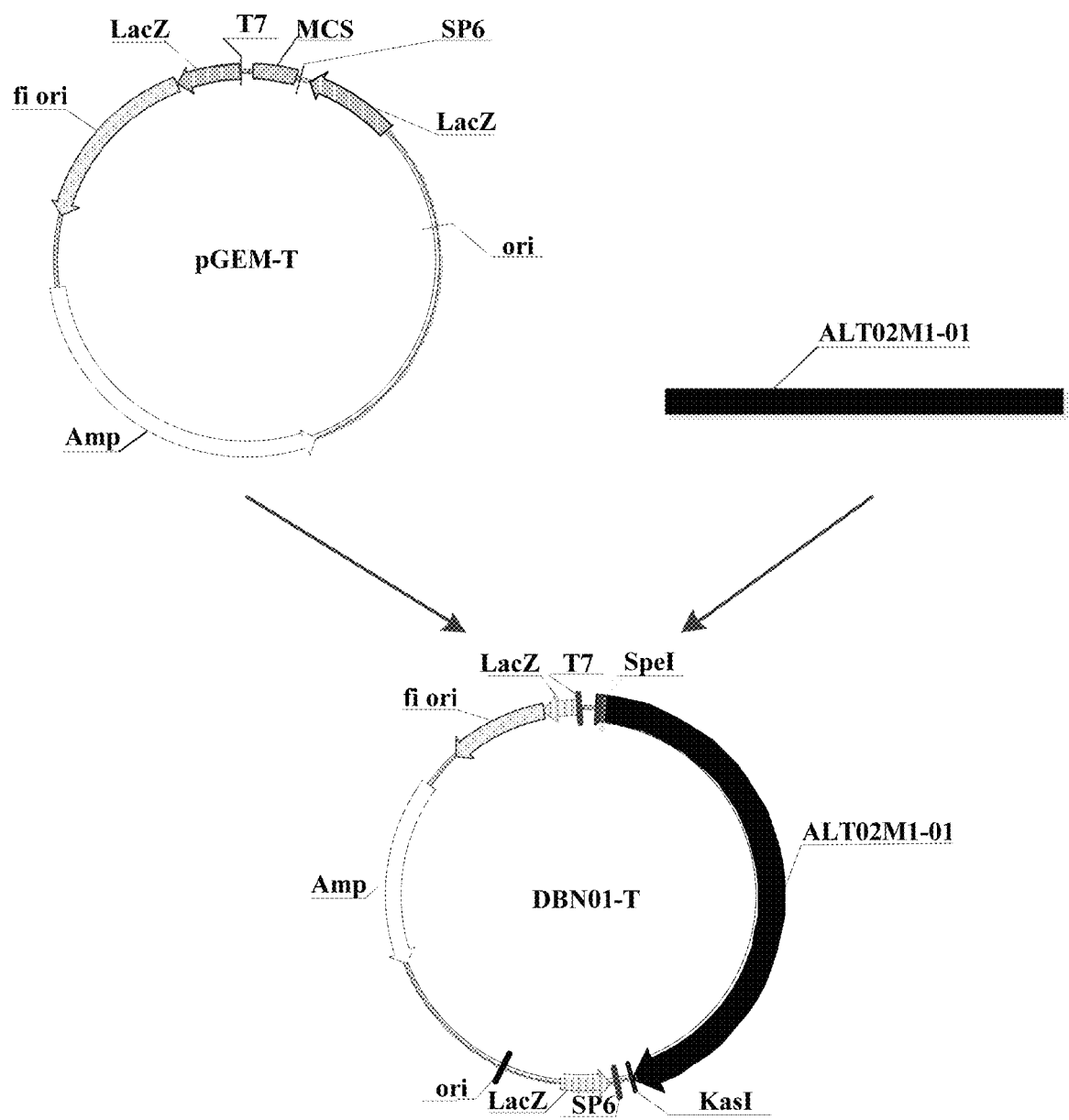
FIG. 1 is a construction flow chart of a recombinant cloning vector DBN01-T containing an ALT02M1-01 nucleotide sequence for the herbicide tolerant protein, the coding gene thereof and a use thereof in the present invention.

The technical solutions of the herbicide tolerant protein, the coding gene thereof and use thereof in the present invention are further described through specific examples below.

Example 1. Mutation and Screening of ALT Gene

1. Synthesis of ALT Gene

The nucleotide sequence (1197 nucleotides) of the ALT01 gene as shown in SEQ ID NO: 2 in the sequence listing was synthesized, which encodes the ALT01 protein (398 amino acids) as shown in SEQ ID NO: 1 in the sequence listing. The nucleotide sequence (SEQ ID NO: 2) of the synthetic ALT01 gene was ligated with a SpeI restriction enzyme site at the 5' end and a KasI restriction enzyme site at the 3' end. The ALT01-01 nucleotide sequence as shown in SEQ ID NO: 3 in the sequence listing encoding the amino acid sequence corresponding to ALT01 was obtained based on soybean codon usage bias, and the ALT01-02 nucleotide sequence as shown in SEQ ID NO: 4 in the sequence listing encoding the amino acid sequence corresponding to the herbicide tolerant protein ALT01 was obtained based on the maize codon usage bias.

2. Construction of a Mutant Library of ALT01 Gene

The above synthetic ALT01 gene was amplified by PCR, and then was cloned into the vector pGEM-T according to the operational procedure in the instructions of product pGEM-T vector (Promega, Madison, USA, CAT: A3600) of Promega Corporation. Then, the above ligated product was introduced into *Escherichia coli* DH5α as a template to carry out error-prone PCR using primer 1 and primer 2, so that the ALT01 gene was mutated due to random base mismatch. The primers and error-prone PCR reaction system were as follows:

```
primer 1:
ATGGAAACCGATAAAAAAACCG,
as shown in SEQ ID NO: 5 in the sequence listing;

primer 2:
TCAGCTTTCGTTCTGATCTAAG,
as shown in SEQ ID NO: 6 in the sequence listing;
```

Error-Prone PCR Reaction System (Total Volume: 50 μL):

| 2 × StarMut Random System | 25 μL |
| Plasmid DNA template | 1 μL |
| Primer 1 | 1 μL |
| Primer 2 | 1 μL |
| StarMut Enhancer | 0-20 μL |
| Water (ddH$_2$O) | added to 50 μL |

The plasmid DNA template having a concentration of 1-10 ng/μL, the primer 1 having a concentration of 10 μM, and the primer 2 having a concentration of 10 μM, were stored at 4° C. in an amber tube.

Error-Prone PCR Reaction Conditions:

| Step | temperature | time |
|---|---|---|
| 11 | 95° C. | 2 min |
| 12 | 94° C. | 30 s |
| 13 | 55° C. | 1 min |
| 14 | 72° C. | 1.5 min |
| 15 | back to step 12, | 30 cycles |
| 16 | 72° C. | 10 min |

The above error-prone PCR product was transformed into tribenuron-methyl-sensitive *Escherichia coli* DH10B ilvG$^+$ by heat shock at 42° C. to construct a random mutant library of ALT01 gene.

3. Screening of a Mutant Library of ALT01 Gene

The transformed product in the above mutant library was inoculated onto a screening medium (glucose 5 g/L, ampicillin 100 mg/L, valine 200 mg/L, leucine 200 mg/L, (NH$_4$)$_2$SO$_4$ 2 g/L, MgSO$_4$·7H$_2$O 200 mg/L, CaCl$_2$·2H$_2$O 10 mg/L, FeSO$_4$·7H$_2$O 1 mg/L, Na$_2$HPO$_4$·12H$_2$O 1.5 g/L and KH$_2$PO$_4$ 1.5 g/L) containing tribenuron-methyl at a concentration of 200 mg/L, and was cultured at a temperature of 37° C. for 24 h.

In view of the ability of a resistance gene to transform tribenuron-methyl to benzenesulfonic acid which is non-toxic to bacteria, the above mutant library was subjected to high-throughput screening using the principle, and *Escherichia coli* DH10B ilvG$^+$, which is still able to grow on the screening medium containing tribenuron-methyl at a concentration of 200 mg/L, was isolated to obtain a resistance gene.

4. Acquisition of Mutant Resistance Genes

The sequencing results showed acquisition of three mutant resistance genes of ALT01, which were named ALT01M1, ALT01M2 and ALT01M3 genes respectively. The nucleotide sequence of ALT01M1 was mutated at position 527 from G to C, resulting in mutation from glycine to alanine at position 176 of the amino acid sequence of ALT01M1; the nucleotide sequence of ALT01M2 was mutated at positions 532 and 533 from TC to GT, resulting in mutation from serine to valine at position 178 of the amino acid sequence of ALT01M2; the nucleotide sequence of ALT01M3 was mutated at positions 239 to 242 from CATA to GAGC, and at positions 527 to 544 from GAAACTCCAGTAAAGAAG to CAAACGTCAGTAAAGAAA, resulting in mutation from proline and tyrosine to arginine and alanine at positions 80 to 81 and mutation from glycine, serine and glycine to alanine, valine and arginine at positions 176, 178 and 182 of the amino acid sequence of ALT01M3.

The amino acid sequence of the herbicide tolerant protein ALT01M1 is shown in SEQ ID NO: 7 in the sequence listing, and the ALT01M1 nucleotide sequence which encodes the amino acid sequence of the herbicide tolerant protein ALT01M1 is shown in SEQ ID NO: 8 in the sequence listing; the ALT01M1-01 nucleotide sequence as shown in SEQ ID NO: 9 in the sequence listing encoding the amino acid sequence corresponding to the herbicide tolerant protein ALT01M1 was obtained based on the soybean codon usage bias; the ALT01M1-02 nucleotide sequence as shown in SEQ ID NO: 10 in the sequence listing encoding the amino acid sequence corresponding to the herbicide tolerant protein ALT01M1 was obtained based on the maize codon usage bias.

The amino acid sequence of the herbicide tolerant protein ALT01M2 is shown in SEQ ID NO: 11 in the sequence listing, and the ALT01M2 nucleotide sequence which encodes the amino acid sequence of the herbicide tolerant protein ALT01M2 is shown in SEQ ID NO: 12 in the sequence listing; the ALT01M2-01 nucleotide sequence as shown in SEQ ID NO: 13 in the sequence listing encoding the amino acid sequence corresponding to the herbicide tolerant protein ALT01M2 was obtained based on the soybean codon usage bias; the ALT01M2-02 nucleotide sequence as shown in SEQ ID NO: 14 in the sequence listing encoding the amino acid sequence corresponding to the herbicide tolerant protein ALT01M2 was obtained based on the maize codon usage bias.

The amino acid sequence of the herbicide tolerant protein ALT01M3 is shown in SEQ ID NO: 15 in the sequence listing, and the ALT01M3 nucleotide sequence which encodes the amino acid sequence of the herbicide tolerant protein ALT01M3 is shown in SEQ ID NO: 16 in the sequence listing; the ALT01M3-01 nucleotide sequence as shown in SEQ ID NO: 17 in the sequence listing encoding the amino acid sequence corresponding to the herbicide tolerant protein ALT01M3 was obtained based on the soybean codon usage bias; the ALT01M3-02 nucleotide sequence as shown in SEQ ID NO: 18 in the sequence listing encoding the amino acid sequence corresponding to the herbicide tolerant protein ALT01M3 was obtained based on the maize codon usage bias.

Synthesis of the Following Nucleotide Sequences:

The amino acid sequence (369 amino acids) of ALT02 is shown in SEQ ID NO: 19 in the sequence listing, and the ALT02 nucleotide sequence (1110 nucleotides) which encodes the amino acid sequence of ALT02 is shown in SEQ ID NO: 20 in the sequence listing; the ALT02-01 nucleotide sequence as shown in SEQ ID NO: 21 in the sequence listing encoding the amino acid sequence corresponding to the ALT02 was obtained based on the soybean codon usage bias; the ALT02-02 nucleotide sequence as shown in SEQ ID NO: 22 in the sequence listing encoding the amino acid sequence corresponding to the herbicide tolerant protein ALT02 was obtained based on the maize codon usage bias.

The herbicide tolerant protein ALT02M1 includes a mutation from glycine to alanine at position 140 of the amino acid sequence of the ALT02. The amino acid sequence of ALT02M1 is shown in SEQ ID NO: 23 in the sequence listing, and the ALT02M1 nucleotide sequence which encodes the amino acid sequence of the herbicide tolerant protein ALT02M1 is shown in SEQ ID NO: 24 in the sequence listing; the ALT02M1-01 nucleotide sequence as shown in SEQ ID NO: 25 in the sequence listing encoding the amino acid sequence corresponding to the herbicide tolerant protein ALT02M1 was obtained based on the soybean codon usage bias; the ALT02M1-02 nucleotide sequence as shown in SEQ ID NO: 26 in the sequence listing encoding the amino acid sequence corresponding to the herbicide tolerant protein ALT02M1 was obtained based on the maize codon usage bias.

The herbicide tolerant protein ALT02M2 includes a mutation from serine to valine at position 142 of the amino acid sequence of the ALT02. The amino acid sequence of the ALT02M2 is shown in SEQ ID NO: 27 in the sequence listing, and the ALT02M2 nucleotide sequence which encodes the amino acid sequence of the herbicide tolerant protein ALT02M2 is shown in SEQ ID NO: 28; the ALT02M2-01 nucleotide sequence as shown in SEQ ID NO: 29 in the sequence listing encoding the amino acid sequence corresponding to the herbicide tolerant protein ALT02M2 was obtained based on the soybean codon usage bias; the ALT02M2-02 nucleotide sequence as shown in SEQ ID NO: 30 in the sequence listing encoding the amino acid sequence corresponding to the herbicide tolerant protein ALT02M2 was obtained based on the maize codon usage bias.

The herbicide tolerant protein ALT02M3 includes mutations from proline and tyrosine to arginine and alanine at positions 44 to 45 and mutations from glycine, serine and glycine to alanine, valine and arginine at positions 140, 142 and 146 of the amino acid sequence of the ALT02. The amino acid sequence of the ALT02M3 is shown in SEQ ID NO: 31 in the sequence listing, and the ALT02M3 nucleotide sequence which encodes the amino acid sequence of the herbicide tolerant protein ALT02M3 is shown in SEQ ID NO: 32 in the sequence listing; the ALT02M3-01 nucleotide sequence as shown in SEQ ID NO: 33 in the sequence listing encoding the amino acid sequence corresponding to the herbicide tolerant protein ALT02M3 was obtained based on the soybean codon usage bias; the ALT02M3-02 nucleotide sequence as shown in SEQ ID NO: 34 in the sequence listing encoding the amino acid sequence corresponding to the herbicide tolerant protein ALT02M3 was obtained based on the maize codon usage bias.

The amino acid sequence (362 amino acids) of ALT03 is shown in SEQ ID NO: 35 in the sequence listing, and the ALT03 nucleotide sequence (1089 nucleotides) which encodes the amino acid sequence of the ALT03 is shown in SEQ ID NO: 36 in the sequence listing; the ALT03-01 nucleotide sequence as shown in SEQ ID NO: 37 in the sequence listing encoding the amino acid sequence corresponding to the ALT03 was obtained based on the soybean codon usage bias; the ALT03-02 nucleotide sequence as shown in SEQ ID NO: 38 in the sequence listing encoding the amino acid sequence corresponding to the herbicide tolerant protein ALT03 was obtained based on the maize codon usage bias.

The herbicide tolerant protein ALT03M1 includes a mutation from glycine to alanine at position 140 of the amino acid sequence of the ALT03. The amino acid sequence of the ALT03M1 is shown in SEQ ID NO: 39 in the sequence listing, and the ALT03M1 nucleotide sequence which encodes the amino acid sequence of the herbicide tolerant protein ALT03M1 is shown in SEQ ID NO: 40 in the sequence listing; the ALT03M1-01 nucleotide sequence as shown in SEQ ID NO: 41 in the sequence listing encoding the amino acid sequence corresponding to the herbicide tolerant protein ALT03M1 was obtained based on the soybean codon usage bias; the ALT03M1-02 nucleotide sequence as shown in SEQ ID NO: 42 in the sequence listing encoding the amino acid sequence corresponding to the herbicide tolerant protein ALT03M1 was obtained based on the maize codon usage bias.

The herbicide tolerant protein ALT03M2 includes a mutation from serine to valine at position 142 of the amino acid sequence of the ALT03. The amino acid sequence of the ALT03M2 is shown in SEQ ID NO: 43 in the sequence listing, and the ALT03M2 nucleotide sequence which encodes the amino acid sequence of the herbicide tolerant protein ALT03M2 is shown in SEQ ID NO: 44 in the sequence listing; the ALT03M2-01 nucleotide sequence as shown in SEQ ID NO: 45 in the sequence listing encoding the amino acid sequence corresponding to the herbicide tolerant protein ALT03M2 was obtained based on the soybean codon usage bias; the ALT03M2-02 nucleotide sequence as shown in SEQ ID NO: 46 in the sequence listing encoding the amino acid sequence corresponding to the herbicide tolerant protein ALT03M2 was obtained based on the maize codon usage bias.

The herbicide tolerant protein ALT03M3 includes mutations from proline and tyrosine to arginine and alanine at positions 44 to 45 and mutations from glycine, serine and glycine to alanine, valine and arginine at positions 140, 142 and 146 of the amino acid sequence of the ALT03. The amino acid sequence of the ALT03M3 is shown in SEQ ID NO: 47 in the sequence listing, and the ALT03M3 nucleotide sequence which encodes the amino acid sequence of the herbicide tolerant protein ALT03M3 is shown in SEQ ID NO: 48 in the sequence listing; the ALT03M3-01 nucleotide sequence as shown in SEQ ID NO: 49 in the sequence listing encoding the amino acid sequence corresponding to the herbicide tolerant protein ALT03M3 was obtained based on the soybean codon usage bias; the ALT03M3-02 nucleotide sequence as shown in SEQ ID NO: 50 in the sequence listing encoding the amino acid sequence corresponding to the herbicide tolerant protein ALT03M3 was obtained based on the maize codon usage bias.

The amino acid sequence (350 amino acids) of ALT04 is shown in SEQ ID NO: 51 in the sequence listing, and the ALT04 nucleotide sequence (1053 nucleotides) which encodes the amino acid sequence of the ALT04 is shown in SEQ ID NO: 52 in the sequence listing; the ALT04-01 nucleotide sequence as shown in SEQ ID NO: 53 in the sequence listing encoding the amino acid sequence corresponding to the ALT04 was obtained based on the soybean codon usage bias; the ALT04-02 nucleotide sequence as shown in SEQ ID NO: 54 in the sequence listing encoding the amino acid sequence corresponding to the herbicide tolerant protein ALT04 was obtained based on the maize codon usage bias.

The herbicide tolerant protein ALT04M1 includes a mutation from glycine to alanine at position 131 of the amino acid sequence of the ALT04. The amino acid sequence of the ALT04M1 is shown in SEQ ID NO: 55 in the sequence listing, and the ALT04M1 nucleotide sequence which encodes the amino acid sequence of the herbicide tolerant protein ALT04M1 is shown in SEQ ID NO: 56 in the sequence listing; the ALT04M1-01 nucleotide sequence as shown in SEQ ID NO: 57 in the sequence listing encoding the amino acid sequence corresponding to the herbicide tolerant protein ALT04M1 was obtained based on the soybean codon usage bias; the ALT04M1-02 nucleotide sequence as shown in SEQ ID NO: 58 in the sequence listing encoding the amino acid sequence corresponding to the herbicide tolerant protein ALT04M1 was obtained based on the maize codon usage bias.

The herbicide tolerant protein ALT04M2 includes a mutation from serine to valine at position 133 of the amino acid sequence of the ALT04. The amino acid sequence of the ALT04M2 is shown in SEQ ID NO: 59 in the sequence listing, and the ALT04M2 nucleotide sequence which encodes the amino acid sequence of the herbicide tolerant protein ALT04M2 is shown in SEQ ID NO: 60 in the sequence listing; the ALT04M2-01 nucleotide sequence as shown in SEQ ID NO: 61 in the sequence listing encoding the amino acid sequence corresponding to the herbicide tolerant protein ALT04M2 was obtained based on the soybean codon usage bias; the ALT04M2-02 nucleotide sequence as shown in SEQ ID NO: 62 in the sequence listing encoding the amino acid sequence corresponding to the herbicide tolerant protein ALT04M2 was obtained based on the maize codon usage bias.

The herbicide tolerant protein ALT04M3 includes mutations from proline and tyrosine to arginine and alanine at positions 35 to 36 and mutations from glycine, serine and glycine to alanine, valine and arginine at positions 131, 133 and 137 of the amino acid sequence of the ALT04. The amino acid sequence of the ALT04M3 is shown in SEQ ID NO: 63 in the sequence listing, and the ALT04M3 nucleotide sequence which encodes the amino acid sequence of the herbicide tolerant protein ALT04M3 is shown in SEQ ID NO: 64 in the sequence listing; the ALT04M3-01 nucleotide sequence as shown in SEQ ID NO: 65 in the sequence listing encoding the amino acid sequence corresponding to the herbicide tolerant protein ALT04M3 was obtained based on the soybean codon usage bias; the ALT04M3-02 nucleotide sequence as shown in SEQ ID NO: 66 in the sequence listing encoding the amino acid sequence corresponding to the herbicide tolerant protein ALT04M3 was obtained based on the maize codon usage bias.

Example 2. Expression and Purification of Protein

1. PCR Amplification of Genes
A pair of primers were designed:

```
primer 3:
TGCAGACATATGGAAACCGATAAAAAAAC
(the portion underlined being Nde I restriction
enzyme site), as shown in SEQ ID NO: 67 in the
sequence listing;

primer 4:
CCCAAGCTTCTAGCTTTCGTTCTGATCTAAGCCGTGC
(the portion underlined being Hind III restriction
enzyme site), as shown in SEQ ID NO: 68 in the
sequence listing;
```

The ALT01M1 gene (terminal containing Nde I and Hind III restriction enzyme sites) was amplified using the following PCR amplification system:

| | |
|---|---|
| Taq DNA polymerase (5 U/μL) | 0.5 μL |
| 5 × PrimeSTARBuffer (Mg$^{2+}$ Plus) | 25 μL |
| dNTP mixture (each 2.5 mM) | 5 μL |
| Template DNA (M1 gene) | 10 ng |
| Primer 3 (25 μM) | 1 μL |
| Primer 4 (25 μM) | 1 μL |
| Water (ddH$_2$O) | added to 50 μL |

PCR reaction conditions: denaturation at 98° C. for 1 min; then entering the following cycle: denaturation at 98° C. for 15 s, annealing at 55° C. for 15 s, extension at 72° C. for 1 min, totally including 29 cycles; finally extension at 72° C. for 10 min, and cooling to room temperature.

According to the above PCR amplification method, the ALT01M2 nucleotide sequence, the ALT01M3 nucleotide sequence, the ALT01 nucleotide sequence, the ALT03M1 nucleotide sequence, the ALT03M2 nucleotide sequence, the ALT03M3 nucleotide sequence, ALT03 nucleotide sequence, ALT04M1 nucleotide sequence, ALT04M2 nucleotide sequence, ALT04M3 nucleotide sequence and ALT04 nucleotide sequence, which contain the Nde I and Hind III restriction enzyme sites at terminals, were amplified. ALT02M1 nucleotide sequence, ALT02M2 nucleotide sequence, ALT02M3 nucleotide sequence, and ALT02 nucleotide sequence (terminals of which contain Nde I and Hind III restriction enzyme sites, respectively) were synthesized.

2. Construction of a Bacterial Expression Vector and Acquisition of Recombinant Microorganisms
The above PCR amplification product (the ALT01M1 nucleotide sequence, the ALT01M2 nucleotide sequence, the ALT01M3 nucleotide sequence, the ALT01 nucleotide sequence, the ALT02M1 nucleotide sequence, the ALT02M2 nucleotide sequence, the ALT02M3 nucleotide sequence, the ALT02 nucleotide sequence, the ALT03M1 nucleotide sequence, the ALT03M2 nucleotide sequence, the ALT03M3 nucleotide sequence, the ALT03 nucleotide sequence, the ALT04M1 nucleotide sequence, the ALT04M2 nucleotide sequence, the ALT04M3 nucleotide sequence and the ALT04 nucleotide sequence, which contain the Nde I and Hind III restriction enzyme sites at terminals) and a bacterial expression vector pET-30a (+) were digested respectively with restriction enzymes Nde I and Hind III, the excised gene fragments mentioned above were enzymatically linked respectively with the bacterial expression vector pET-30a (+) after enzyme digestion, and the enzymatically linked products were transformed respectively to the expression host strain BL21 (DE3) to obtain the recombinant microorganisms BL21 (ALT01M1), BL21 (ALT01M2), BL21 (ALT01M3), BL21 (ALT01), BL21 (ALT02M1), BL21 (ALT02M2), BL21 (ALT02M3), BL21 (ALT02), BL21 (ALT03M1), BL21 (ALT03M2), BL21 (ALT03M3), BL21 (ALT03), BL21 (ALT04M1), BL21 (ALT04M2), BL21 (ALT04M3), and BL21 (ALT04).

3. Expression and Purification of Herbicide Tolerant Protein in *Escherichia coli*

The recombinant microorganisms BL21 (ALT01M1), BL21 (ALT01M2), BL21 (ALT01M3), BL21 (ALT01), BL21 (ALT02M1), BL21 (ALT02M2), BL21 (ALT02M3), BL21 (ALT02), BL21 (ALT03M1), BL21 (ALT03M2), BL21 (ALT03M3), BL21 (ALT03), BL21 (ALT04M1), BL21 (ALT04M2), BL21 (ALT04M3), and BL21 (ALT04) were cultured in 100 mL of LB medium (10 g/L of tryptone, 5 g/L of yeast extract, 10 g/L of NaCl and 100 mg/L of ampicillin, adjusted to pH 7.5 with NaOH) to a concentration of $OD_{600nm}=0.6$-$0.8$, and induced with isopropyl thiogalactoside (IPTG) added at a concentration of 0.4 mM at a temperature of 16° C. for 20 hours. Bacterial cells were collected by centrifugation and resuspended in 20 ml of Tris-HCl buffer (100 mM, pH 8.0), followed by performing ultrasonication (X0-900D ultrasonic processor ultrasonic processor, 30% intensity) for 10 min, then centrifuging, collecting the supernatant, purifying the acquired herbicide tolerant proteins mentioned above with nickel ion affinity chromatography column, and detecting the purification result using SDS-PAGE protein electrophoresis with the band size being consistent with theoretically predicted band size.

Example 3. Determination of Enzymatic Activity of Herbicide Tolerant Protein

Enzymatic reaction system (1 mL) contains 0.2 μg of reactive enzyme (the herbicide tolerant proteins ALT01M1, ALT01M2, ALT01M3, ALT01, ALT02M1, ALT02M2, ALT02M3, ALT02, ALT03M1, ALT03M2, ALT03M3, ALT03, ALT04M1, ALT04M2, ALT04M3 and ALT04 obtained from the above purification), 0.2 mM of thifensulfuron-methyl (metsulfuron-methyl, chlorimuron-ethyl, bensulfuron-methyl, sulfometuron-methyl or tribenuron-methyl), and a buffer system of phosphate buffer at a concentration of 50 mM (pH 7.0), which were reacted in a water bath at a temperature of 30° C. for 20 min. Each reaction was timed beginning with the addition of reactive enzyme, and was terminated with 1 mL of dichloromethane. The organic phase after delamination was dehydrated with anhydrous sodium sulfate.

The above dehydrated reaction solution was blown dry with nitrogen and filtered by adding 1 mL of methanol, and 20 μL of the filtrate was subjected to liquid chromatography-mass spectrometry (LC-MS). High performance liquid chromatography (HPLC) conditions were as follows: mobile phase being methanol:water (80:20, V/V), Zorbax XDB-C18 chromatographic column (3.5 μm, 2.1×50 mm, Agilent, USA), column temperature being room temperature, UV detector, with a detection wavelength of 255 nm, a sample injection volume of 20 μL, and a flow rate of 0.25 mL/min. The primary ion mass spectrometry conditions were as follows: ion detection mode being multi-reactive ion detection; ion polarity being negative ion; ionization mode being electrospray ionization; a capillary voltage of 4000 volts; a dry gas temperature of 330° C., a flow rate of 10 L/min, an atomizing gas pressure of 35 psi, a collision voltage of 135 volts; and a mass scan range of 300-500 m/z. The secondary ion mass spectrometry conditions were as follows: a collision voltage of 90 volts; a mass scanning range of 30-400 m/z, and other conditions being the same as those of the primary ion mass spectrometry. It was identified by LC-MS that the metabolite of thifensulfuron-methyl was thiophene sulfonic acid, and the metabolite of metsulfuron-methyl, chlorimuron-ethyl, bensulfuron-methyl, sulfometuron-methyl or tribenuron-methyl was its corresponding sulfonic acid. The amount of the generated thiophene sulfonic acid (metabolite) was detected using high performance liquid chromatography (HPLC). An enzyme activity unit was defined as the amount of enzyme required for catalyzing the degradation of thifensulfuron-methyl (metsulfuron-methyl, chlorimuron-ethyl, bensulfuron-methyl, sulfometuron-methyl or tribenuron-methyl) at pH 7.0, at a temperature of 30° C. within 1 min to decrease 1 μmol of thifensulfuron-methyl (metsulfuron-methyl, chlorimuron-ethyl, bensulfuron-methyl, sulfometuron-methyl or tribenuron-methyl), which is expressed as U. Experimental results were shown in Table 1.

TABLE 1

Experimental results of degradation of sulfonylurea herbicides by herbicide tolerant proteins

| specific enzyme activity (μmol/min/mg) | tribenuron-methyl | bensulfuron-methyl | thifensulfuron-methyl | metsulfuron-methyl | chlorimuron-ethyl | sulfometuron-methyl |
|---|---|---|---|---|---|---|
| ALT01 | 1.8 | 1.7 | 27.4 | 2.0 | 2.7 | 1.9 |
| ALT01M1 | 3.1 | 3.9 | 89.9 | 2.2 | 10.4 | 5.4 |
| ALT01M2 | 10.8 | 2.4 | 106.0 | 1.2 | 9.0 | 3.5 |
| ALT01M3 | 3.3 | 0.68 | 17.8 | 4.2 | 38.4 | 1.1 |
| ALT02 | 1.9 | 1.8 | 28.8 | 2.1 | 2.8 | 2.0 |
| ALT02M1 | 3.3 | 4.1 | 94.4 | 2.3 | 10.9 | 5.7 |
| ALT02M2 | 11.3 | 2.5 | 111.3 | 1.3 | 9.5 | 3.7 |
| ALT02M3 | 3.5 | 0.7 | 18.7 | 4.4 | 40.3 | 1.2 |
| ALT03 | 1.7 | 1.6 | 26.0 | 1.9 | 2.6 | 1.8 |
| ALT03M1 | 2.9 | 3.7 | 85.4 | 2.1 | 9.9 | 5.1 |
| ALT03M2 | 10.3 | 2.3 | 100.7 | 1.1 | 8.6 | 3.3 |

TABLE 1-continued

Experimental results of degradation of sulfonylurea herbicides by herbicide tolerant proteins

| specific enzyme activity (μmol/min/mg) | tribenuron-methyl | bensulfuron-methyl | thifensulfuron-methyl | metsulfuron-methyl | chlorimuron-ethyl | sulfometuron-methyl |
|---|---|---|---|---|---|---|
| ALT03M3 | 3.1 | 0.6 | 16.9 | 4.0 | 36.5 | 1.0 |
| ALT04 | 1.6 | 1.5 | 24.7 | 1.8 | 2.4 | 1.7 |
| ALT04M1 | 2.8 | 3.5 | 80.9 | 2.0 | 9.4 | 4.9 |
| ALT04M2 | 9.7 | 2.2 | 95.4 | 1.1 | 8.1 | 3.2 |
| ALT04M3 | 3.0 | 0.6 | 16.0 | 3.8 | 34.6 | 1.0 |

The above experimental results indicate that compared with the herbicide tolerant protein ALT01, the purified herbicide tolerant protein ALT01M1 degrades tribenuron-methyl, bensulfuron-methyl and thifensulfuron-methyl at efficiencies that are 1.7, 2.3 and 3.3-fold of those of ALT01 respectively; the purified herbicide tolerant protein ALT01M2 degrades tribenuron-methyl, bensulfuron-methyl and thifensulfuron-methyl at efficiencies that are 6.0, 1.4 and 3.9-fold of those of ALT01 respectively; the purified herbicide tolerant protein ALT01M3 degrades tribenuron-methyl, metsulfuron-methyl and chlorimuron-ethyl at efficiencies that are 1.9, 2.1 and 14.2-fold of those of ALT01 respectively.

Compared with the herbicide tolerant protein ALT02, the purified herbicide tolerant protein ALT02M1 degrades tribenuron-methyl, bensulfuron-methyl and thifensulfuron-methyl at efficiencies that are 1.7, 2.3 and 3.3-fold of those of ALT02 respectively; the purified herbicide tolerant protein ALT02M2 degrades tribenuron-methyl, bensulfuron-methyl and thifensulfuron-methyl at efficiencies that are 5.9, 1.4 and 3.9-fold of those of ALT02 respectively; the purified herbicide tolerant protein ALT02M3 degrades tribenuron-methyl, metsulfuron-methyl and chlorimuron-ethyl at efficiencies that are 1.8, 2.1 and 14.2-fold of those of ALT02 respectively.

Compared with the herbicide tolerant protein ALT03, the purified herbicide tolerant protein ALT03M1 degrades tribenuron-methyl, bensulfuron-methyl and thifensulfuron-methyl at efficiencies that are 1.5, 2.1 and 3.0-fold of those of ALT03 respectively; the purified herbicide tolerant protein ALT03M2 degrades tribenuron-methyl, bensulfuron-methyl and thifensulfuron-methyl at efficiencies that are 5.4, 1.3 and 3.5-fold of those of ALT03 respectively; the purified herbicide tolerant protein ALT03M3 degrades tribenuron-methyl, metsulfuron-methyl and chlorimuron-ethyl at efficiencies that are 1.6, 1.9 and 13.0-fold of those of ALT03 respectively.

Compared with the herbicide tolerant protein ALT04, the purified herbicide tolerant protein ALT04M1 degrades tribenuron-methyl, bensulfuron-methyl and thifensulfuron-methyl at efficiencies that are 1.5, 1.9 and 2.8-fold of those of ALT04 respectively; the purified herbicide tolerant protein ALT04M2 degrades tribenuron-methyl, bensulfuron-methyl and thifensulfuron-methyl at efficiencies that are 5.1, 1.2 and 3.3-fold of those of ALT04 respectively; the purified herbicide tolerant protein ALT03M3 degrades tribenuron-methyl, metsulfuron-methyl and chlorimuron-ethyl at efficiencies that are 1.6, 1.8 and 12.4-fold of those of ALT04 respectively.

It thus can be seen that, in the amino acid sequence of the herbicide tolerant protein ALT01, mutation at position 176 from glycine to alanine and/or mutation at position 178 position from serine to valine both can enhance the ability of mutant genes (such as the ALT01M1, ALT01M2 or ALT01M3 gene) to degrade sulfonylurea herbicides, especially tribenuron-methyl. In the amino acid sequence of the herbicide tolerant protein ALT02 (or ALT03), mutation at position 140 from glycine to alanine and/or mutation at position 142 from serine to valine both can enhance the ability of mutant genes (such as the ALT02M1, ALT02M2, ALT02M3, ALT03M1, ALT03M2 or ALT03M3 gene) to degrade sulfonylurea herbicides, especially tribenuron-methyl. In the amino acid sequence of the herbicide tolerant protein ALT04, mutation at position 131 from glycine to alanine and/or mutation at position 133 from serine to valine both can enhance the ability of mutant genes (such as the ALT04M1, ALT04M2 or ALT04M3 gene) to degrade sulfonylurea herbicides, especially tribenuron-methyl.

Example 4. Construction of Recombinant Expression Vectors for Soybean

1. Construction of Recombinant Cloning Vectors Containing ALT02M1-01 Nucleotide Sequence for Soybean The ALT02M1-01 nucleotide sequence was ligated into cloning vector pGEM-T (Promega, Madison, USA, CAT: A3600) according to the operational procedure in the instructions of product pGEM-T vector of Promega Corporation, thereby obtaining a recombinant cloning vector DBN01-T, the construction process of which was as shown in FIG. 1 (wherein, Amp represents the ampicillin resistance gene; f1 represents the origin of replication of phage f1; LacZ is LacZ initiation codon; SP6 is SP6 RNA polymerase promoter; T7 is T7 RNA polymerase promoter; ALT02M1-01 is the ALT02M1-01 nucleotide sequence (SEQ ID NO: 25); and MCS is a multiple cloning site).

Then, *Escherichia coli* T1 competent cells (Transgen, Beijing, China, CAT: CD501) were transformed with the recombinant cloning vector DBN01-T using the heat shock method under the following heat shock conditions: maintaining 50 μL of *Escherichia coli* T1 competent cells and 10 μL of plasmid DNA (recombinant cloning vector DBN01-T) in water bath at 42° C. for 30 seconds; shake culturing at 37° C. for 1 hour (using a shaker at a rotation speed of 100 rpm for shaking); and growing on an LB plate (10 g/L of tryptone, 5 g/L of yeast extract, 10 g/L of NaCl, and 15 g/L of agar, with a pH adjusted to 7.5 with NaOH) of ampicillin (100 mg/L) having its surface coated with IPTG (isopropylthio-β-D-galactoside) and X-gal (5-bromo-4-chloro-3-indole-β-D-galactoside) overnight. White colonies were picked out and cultured in an LB liquid culture medium (10 g/L of tryptone, 5 g/L of yeast extract, 10 g/L of NaCl, and 100 mg/L of ampicillin, with a pH adjusted to 7.5 with NaOH) at a temperature of 37° C. overnight. The plasmids in the cells were extracted through an alkaline method: centrifuging the bacteria solution at a rotation speed of 12000 rpm for 1 min, removing the supernatant, and suspending the precipitated thalli with 100 μL of ice pre-cooled solution I (25 mM Tris-HCl, 10 mM EDTA (ethylenediaminetetraacetic acid), and 50 mM glucose, with a pH of 8.0); adding 200 μL of newly formulated solution II (0.2M NaOH, 1% SDS (sodium dodecyl sulfate)), inverting the tube 4 times, and mixing and placing on ice for 3-5 min; adding 150 μL of ice-cold solution III (3 M potassium acetate, 5 M acetic acid), mixing uniformly immediately and placing on ice for 5-10 min; centrifuging under the conditions of a temperature of 4° C. and a rotation speed of 12000 rpm for 5 min, adding 2-fold volumes of anhydrous ethanol to the supernatant and placing at room temperature for 5 min after mixing uniformly; centrifuging under the conditions of a temperature of 4° C. and a rotation speed of 12000 rpm for 5 min, discarding the supernatant, and air drying the precipitate after washing with ethanol at a concentration of 70% (V/V); adding 30 μL of TE (10 mM Tris-HCl, and 1 mM EDTA, with a pH of 8.0) containing RNase (20 μg/mL) to dissolve the precipitate; water bathing at a temperature of 37° C. for 30 min to digest the RNA; and storing at a temperature of −20° C. for use.

After identifying the extracted plasmid by SpeI and KasI digestion, positive clones were verified by sequencing. The results showed that the inserted ALT02M1-01 nucleotide sequence in the recombinant cloning vector DBN01-T was the nucleotide sequence as shown in SEQ ID NO: 25 in the sequence listing, that is, the ALT02M1-01 nucleotide sequence was inserted correctly.

Figure 2:
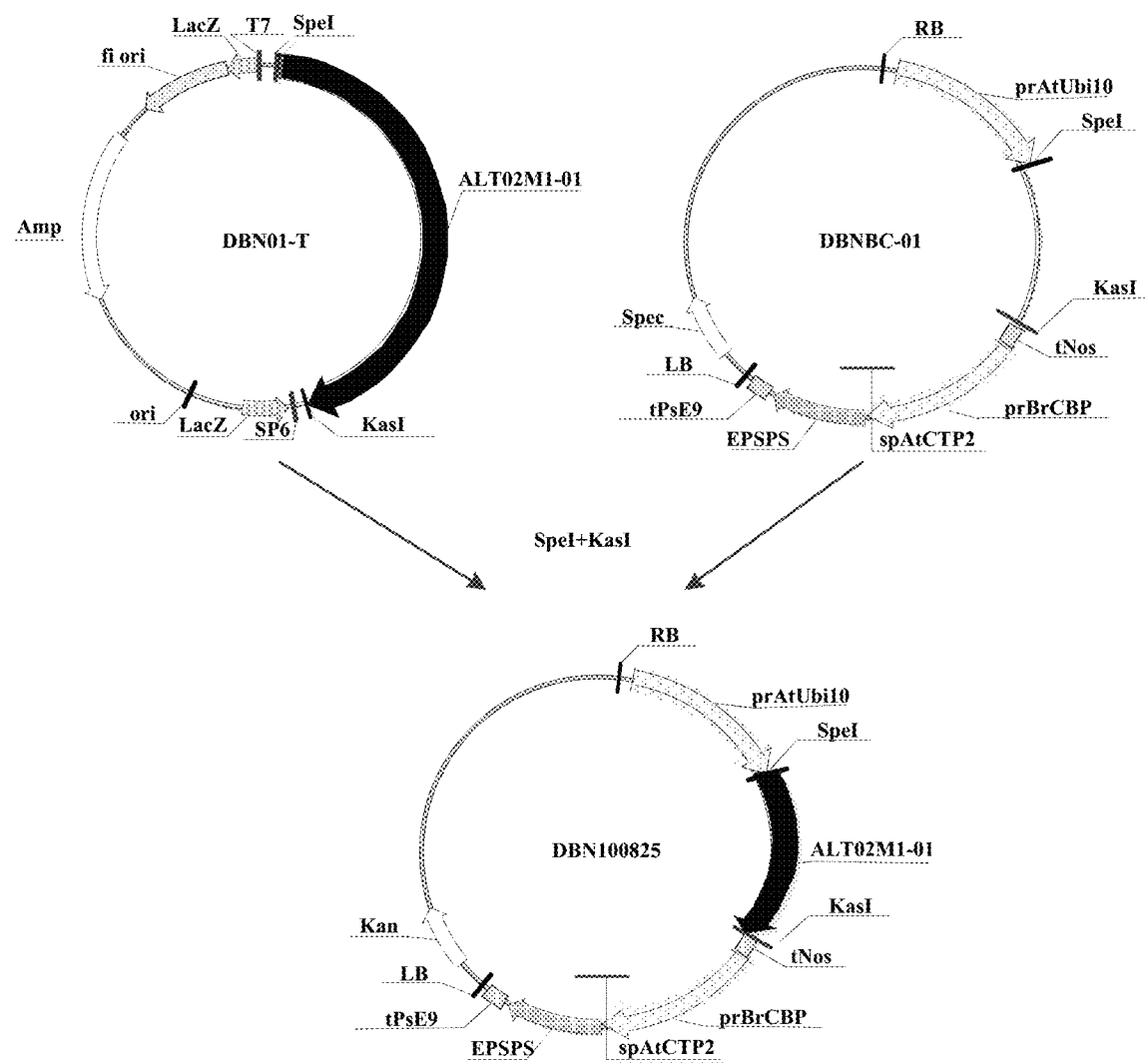
FIG. 2 is a construction flow chart of a recombinant expression vector DBN100825 containing an ALT02M1-01 nucleotide sequence for the herbicide tolerant protein, the coding gene thereof and a use thereof in the present invention.

2. Construction of Recombinant Expression Vectors Containing ALT02M1-01 Nucleotide Sequence for Soybean The recombinant cloning vector DBN01-T and an expression vector DBNBC-01 (vector backbone: pCAMBIA2301 (which can be provided by the CAMBIA institution)) were both digested with restriction enzymes SpeI and KasI respectively; the excised ALT02M1-01 nucleotide sequence fragment was inserted between the SpeI and KasI sites in the expression vector DBNBC-01; and it is well known to a person skilled in the art to construct a vector using conventional enzyme digestion methods, wherein a recombinant expression vector DBN100825 was constructed, the construction process of which was as shown in FIG. 2 (Spec: the spectinomycin gene; RB: the right boundary; prAtUbi10: the *Arabidopsis thaliana* Ubiquitin 10 gene promoter (SEQ ID NO: 69); ALT02M1-01: the ALT02M1-01 nucleotide sequence (SEQ ID NO: 25); tNos: the terminator of a nopaline synthase gene (SEQ ID NO:70); prBrCBP: the rape eukaryotic elongation factor gene 1α (Tsf1) promoter (SEQ ID NO: 71); spAtCTP2: the *Arabidopsis thaliana* chloroplast transit peptide (SEQ ID NO: 72); EPSPS: the 5-enolpyruvylshikimate-3-phosphate synthase gene (SEQ ID NO: 73); tPsE9: the pea RbcS gene terminator (SEQ ID NO: 74); LB: the left boundary).

*Escherichia coli* T1 competent cells were transformed with the recombinant expression vector DBN100825 by a heat shock method under the following heat shock conditions: maintaining 50 μL of *Escherichia coli* T1 competent cells and 10 μL of plasmid DNA (recombinant expression vector DBN100825) in water bath at 42° C. for 30 seconds; shake culturing at 37° C. for 1 hour (using a shaker at a rotation speed of 100 rpm for shaking); then culturing under the condition of a temperature of 37° C. on an LB solid plate containing 50 mg/L of spectinomycin (10 g/L of tryptone, 5 g/L of yeast extract, 10 g/L of NaCl, and 15 g/L of agar, with a pH adjusted to 7.5 with NaOH) for 12 hours, picking white colonies, and culturing under the condition of a temperature of 37° C. overnight in an LB liquid culture medium (10 g/L of tryptone, 5 g/L of yeast extract, 10 g/L of NaCl, and 50 mg/L of spectinomycin, with a pH adjusted to 7.5 with NaOH). The plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant expression vector DBN100825 was the nucleotide sequence as shown in SEQ ID NO: 25 in the sequence listing, i.e., the ALT02M1-01 nucleotide sequence.

The recombinant expression vector DBN100826 containing ALT02M2-01 nucleotide sequence, the recombinant expression vector DBN100827 containing ALT02M3-01 nucleotide sequence, and the recombinant expression vector DBN100828 containing ALT02-01 nucleotide sequence were constructed according to the method for constructing the recombinant expression vector DBN100825 containing ALT02M1-01 nucleotide sequence as described above. Positive clones were verified by sequencing, with the results showing that ALT02M2-01 nucleotide sequence, ALT02M3-01 nucleotide sequence and ALT02-01 nucleotide sequence inserted into the recombinant expression vectors DBN100825, DBN100826, DBN100827 and DBN100828 were the nucleotide sequences as shown in SEQ ID NO: 29, SEQ ID NO: 33 and SEQ ID NO: 21 in the sequence listing respectively, namely ALT02M2-01 nucleotide sequence, ALT02M3-01 nucleotide sequence and ALT02-01 nucleotide sequence were inserted correctly.

Figure 3:
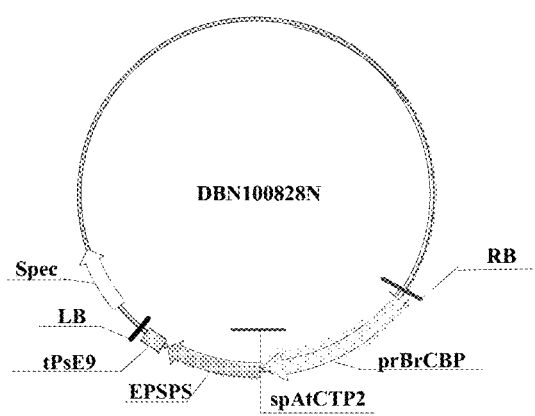
FIG. 3 is a schematic structural diagram of a control recombinant expression vector DBN100828N for the herbicide tolerant protein, the coding gene thereof and a use thereof in the present invention.

According to the method for constructing the recombinant expression vector DBN100825 containing ALT02M1-01 nucleotide sequence as described above, a control recombinant expression vector DBN100828N was constructed, the structure of which is as shown in FIG. 3 (vector backbone: pCAMBIA2301 (which can be provided by the CAMBIA institution); Spec: the spectinomycin gene; RB: the right boundary; prBrCBP: the rape eukaryotic elongation factor gene 1α (Tsf1) promoter (SEQ ID NO: 71); spAtCTP2: the *Arabidopsis thaliana* chloroplast transit peptide (SEQ ID NO: 72); EPSPS: the 5-enolpyruvylshikimate 3-phosphate synthase gene (SEQ ID NO: 73); tPsE9: the pea RbcS gene terminator (SEQ ID NO: 74); LB: the left boundary). Positive clones were verified by sequencing, with the results showing that the control recombinant expression vector DBN100828N was correctly constructed.

3. Transformation of *Agrobacterium* with the Recombinant Expression Vectors

*Agrobacterium* LBA4404 (Invitrogen, Chicago, USA, CAT: 18313-015) was transformed with the recombinant expression vectors DBN100825, DBN100826, DBN100827, DBN100828, and DBN100828N which had been constructed correctly using a liquid nitrogen method, under the following transformation conditions: placing 100 μL of *Agrobacterium* LBA4404 and 3 μL of plasmid DNA (recombinant expression vector) in liquid nitrogen for 10 minutes, and warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, spreading on an LB plate containing 50 mg/L of rifampicin and 50 mg/L of spectinomycin until positive single clones were grown, picking out single clones for culturing and extracting the plasmids thereof, and performing enzyme digestion verification using restriction enzymes. The results showed that the structures of the recombinant expression vectors DBN100825, DBN100826, DBN100827, DBN100828, and DBN100828N were completely correct.

Example 5. Acquisition and Verification of Transgenic Soybean Plants

1. Acquisition of Transgenic Soybean Plants

According to the *Agrobacterium* infection method conventionally used, the cotyledonary node tissue of sterilely cultured soybean variety Zhonghuang13 was co-cultured with the *Agrobacterium* in part 3 of Example 4, so as to introduce the T-DNA (including the *Arabidopsis thaliana* Ubiquitin10 gene promoter sequence, the ALT02M1-01 nucleotide sequence, the ALT02M2-01 nucleotide sequence, the ALT02M3-01 nucleotide sequence, the ALT02-01 nucleotide sequence, the tNos terminator, the rape eukaryotic elongation factor gene 1α promoter, the *Arabidopsis thaliana* chloroplast transit peptide, a 5-enolpyruvylshikimate-3 phosphate synthase gene, and the pea RbcS gene terminator) in the recombinant expression vectors DBN100825, DBN100826, DBN100827, DBN100828, and DBN100828N constructed in Part 2 of Example 4 into the soybean chromosome sets, thereby obtaining soybean plants into which the ALT02M1-01 nucleotide sequence was introduced, soybean plants into which the ALT02M2-01 nucleotide sequence was introduced, soybean plants into which the ALT02M3-01 nucleotide sequence was introduced, and soybean plants into which the ALT02-01 nucleotide sequence was introduced; meanwhile, control soybean plants into which T-DNA in a control recombinant expression vector DBN100828N was introduced and wild-type soybean plants were used as the control.

As regards the *Agrobacterium*-mediated soybean transformation, briefly, mature soybean seeds were germinated in a soybean germination culture medium (3.1 g/L of B5 salt, B5 vitamin, 20 g/L of sucrose, and 8 g/L of agar, with a pH of 5.6), and the seeds were inoculated on a germination culture medium and cultured under the conditions of a temperature of 25±1° C.; and a photoperiod (light/dark) of 16 h/8 h. After 4-6 days of germination, soybean sterile seedlings swelling at bright green cotyledonary nodes were taken, hypocotyledonary axes were cut off 3-4 mm below the cotyledonary nodes, the cotyledons were cut longitudinally, and apical buds, lateral buds and seminal roots were removed. A wound was made at a cotyledonary node using the knife back of a scalpel, and the wounded cotyledonary node tissues were contacted with an *Agrobacterium* suspension, wherein the *Agrobacterium* can transfer the ALT02M1-01 nucleotide sequence (ALT02M2-01 nucleotide sequence, ALT02M3-01 nucleotide sequence or ALT02-01 nucleotide sequence) to the wounded cotyledonary node tissues (step 1: the infection step). In this step, the cotyledonary node tissues were preferably immersed in the *Agrobacterium* suspension ($OD_{660}$=0.5-0.8, an infection culture medium (2.15 g/L of MS salt, B5 vitamin, 20 g/L of sucrose, 10 g/L of glucose, 40 mg/L of acetosyringone (AS), 4 g/L of 2-morpholine ethanesulfonic acid (MES), and 2 mg/L of zeatin (ZT), with a pH of 5.3)) to initiate the inoculation. The cotyledonary node tissues were co-cultured with *Agrobacterium* for a period of time (3 days) (step 2: the co-culturing step). Preferably, the cotyledonary node tissues were cultured in a solid culture medium (4.3 g/L of MS salt, B5 vitamin, 20 g/L of sucrose, 10 g/L of glucose, 4 g/L of MES, 2 mg/L of ZT, and 8 g/L of agar, with a pH of 5.6) after the infection step. After this co-culturing stage, there can be an optional "recovery" step. In the "recovery" step, there may be at least one antibiotic (cephalosporin) known to inhibit the growth of *Agrobacterium* in a recovery culture medium (3.1 g/L of B5 salt, B5 vitamin, 1 g/L of MES, 30 g/L of sucrose, 2 mg/L of ZT, 8 g/L of agar, 150 mg/L of cephalosporin, 100 mg/L of glutamic acid, and 100 mg/L of aspartic acid, with a pH of 5.6), without the addition of a selective agent for a plant transformant (step 3: the recovery step). Preferably, tissue blocks regenerated from the cotyledonary nodes were cultured in a solid culture medium with an antibiotic, but without a selective agent, to eliminate *Agrobacterium* and provide a recovery stage for the infected cells. Subsequently, the tissue blocks regenerated from the cotyledonary nodes were cultured in a culture medium containing a selective agent (glyphosate), and growing transformed calli were selected (step 4: the selection step). Preferably, the tissue blocks regenerated from the cotyledonary nodes were cultured in a screening solid culture medium (3.1 g/L of B5 salt, B5 vitamin, 1 g/L of MES, 30 g/L of sucrose, 1 mg/L of 6-benzyladenine (6-BAP), 8 g/L of agar, 150 mg/L of cephalosporin, 100 mg/L of glutamic acid, 100 mg/L of aspartic acid, and 0.25 mol/L of N-(phosphonomethyl)glycine, with a pH of 5.6) containing a selective agent, thus resulting in selective growth of the transformed cells. Then, plants were regenerated from the transformed cells (step 5: the regeneration step). Preferably, the tissue blocks regenerated from the cotyledonary nodes grown in a culture medium containing a selective agent were cultured in solid culture media (a B5 differentiation culture medium and B5 rooting culture medium) to regenerate plants.

The resistant tissue blocks obtained from screening were transferred onto the B5 differentiation culture medium (3.1 g/L of B5 salt, B5 vitamin, 1 g/L of MES, 30 g/L of sucrose, 1 mg/L of ZT, 8 g/L of agar, 150 mg/L of cephalosporin, 50 mg/L of glutamic acid, 50 mg/L of aspartic acid, 1 mg/L of gibberellin, 1 mg/L of auxin, and 0.25 mol/L of N-(phosphonomethyl)glycine, with a pH of 5.6), and cultured at 25° C. for differentiation. The differentiated seedlings were transferred onto the B5 rooting culture medium (3.1 g/L of B5 salt, B5 vitamin, 1 g/L of MES, 30 g/L of sucrose, 8 g/L of agar, 150 mg/L of cephalosporin, and 1 mg/L of indole-3-butyric acid (IBA)), cultured in the rooting culture medium until reaching a height of about 10 cm at 25° C., and transferred to a greenhouse for culturing until fruiting. In the greenhouse, the plants were cultured at 26° C. for 16 hours, and then cultured at 20° C. for 8 hours every day.

2. Verification of the Transgenic Soybean Plants Using TaqMan

About 100 mg of leaves from the soybean plants into which the ALT02M1-01 nucleotide sequence was introduced, the soybean plants into which the ALT02M2-01 nucleotide sequence was introduced, the soybean plants into which the ALT02M3-01 nucleotide sequence was introduced, the soybean plants into which the ALT02-01 nucleotide sequence was introduced and control soybean plants respectively were taken as samples, and the genomic DNA thereof was extracted with a DNeasy Plant Maxi Kit of Qiagen, and copy numbers of an EPSPS gene were detected by the Taqman probe fluorescence quantitative PCR method so as to determine the copy numbers of the genes of interest. At the same time, wild-type soybean plants were used as controls, and detected and analyzed according to the abovementioned method. Triple repeats were set for the experiments, and were averaged.

The specific method for detecting the copy number of the EPSPS gene was as follows:

Step 21. 100 mg of leaves from the soybean plants into which the ALT02M1-01 nucleotide sequence was introduced, soybean plants into which the ALT02M2-01 nucleotide sequence was introduced, soybean plants into which the ALT02M3-01 nucleotide sequence was introduced and soybean plants into which the ALT02-

01 nucleotide sequence was introduced, control soybean plants and wild-type soybean plants respectively were taken, and ground into a homogenate using liquid nitrogen in a mortar respectively, and triple repeats were taken for each sample;

Step 22. The genomic DNA of the above-mentioned samples was extracted using a DNeasy Plant Mini Kit of Qiagen (for the particular method, refer to the product instructions thereof);

Step 23. The concentrations of the genomic DNA of the above-mentioned samples were detected using Nano-Drop 2000 (Thermo Scientific);

Step 24. The concentrations of the genomic DNA of the above-mentioned samples were adjusted to a consistent concentration value which ranges from 80 to 100 ng/μL;

Step 25. The copy numbers of the samples were identified using the Taqman probe fluorescence quantitative PCR method, wherein samples for which the copy numbers had been identified and known were taken as standards, the samples of the wild-type soybean plants were taken as the control, and triple repeats were taken for each sample, and were averaged; the sequences of fluorescence quantitative PCR primers and a probe were as follows:

The following primers and probe were used to detect the EPSPS gene sequence:

```
primer 5:
CTGGAAGGCGAGGACGTCATCAATA
as shown in SEQ ID NO: 75 in the sequence listing;

primer 6:
TGGCGGCATTGCCGAAATCGAG
as shown in SEQ ID NO: 76 in the sequence listing;

probe 1:
ATGCAGGCGATGGGCGCCCGCATCCGTA
as shown in SEQ ID NO: 77 in the sequence listing;
```

PCR Reaction System:

| | |
|---|---|
| JumpStart ™ Taq ReadyMix ™ (Sigma) | 10 μL |
| 50 × primer/probe mixture | 1 μL |
| genomic DNA | 3 μL |
| water (ddH$_2$O) | 6 μL |

The 50×primer/probe mixture comprises 45 μL of each primer at a concentration of 1 mM, 50 μL of the probe at a concentration of 100 μM, and 860 μL of 1×TE buffer, and was stored at 4° C. in an amber tube.

PCR Reaction Conditions:

| Step | temperature | time |
|---|---|---|
| 31 | 95° C. | 5 min |
| 32 | 95° C. | 30 s |
| 33 | 60° C. | 1 min |
| 34 | back to step 32, repeated 40 times | |

Data was analyzed using software SDS2.3 (Applied Biosystems).

It was further demonstrated, by analyzing the experimental results of the copy number of the EPSPS gene, that the ALT02M1-01 nucleotide sequence, the ALT02M2-01 nucleotide sequence, the ALT02M3-01 nucleotide sequence and the ALT02-01 nucleotide sequence had all been integrated into the chromosome set of the detected soybean plants, and all of the soybean plants into which the ALT02M1-01 nucleotide sequence was introduced, soybean plants into which the ALT02M2-01 nucleotide sequence was introduced, soybean plants into which the ALT02M3-01 nucleotide sequence was introduced and soybean plants into which the ALT02-01 nucleotide sequence was introduced and control soybean plants resulted in single-copy transgenic soybean plants.

Example 6. Detection of Herbicide Tolerance Effects of the Transgenic Soybean Plants The effect of herbicide tolerance to tribenuron-methyl was detected on the soybean plants into which the ALT02M1-01 nucleotide sequence was introduced, the soybean plants into which the ALT02M2-01 nucleotide sequence was introduced, the soybean plants into which the ALT02M3-01 nucleotide sequence was introduced, the soybean plants into which the ALT02-01 nucleotide sequence was introduced, control soybean plants and wild-type soybean plants (at seedling stage V3-V4), respectively.

The soybean plants into which the ALT02M1-01 nucleotide sequence was introduced, the soybean plants into which the ALT02M2-01 nucleotide sequence was introduced, the soybean plants into which the ALT02M3-01 nucleotide sequence was introduced, the soybean plants into which the ALT02-01 nucleotide sequence was introduced, control soybean plants and wild-type soybean plants were taken and sprayed with tribenuron-methyl (144 g ai/ha, eight-fold field concentration) or a blank solvent (water), respectively. The degree of damage caused by the herbicide was measured for each plant according to the leaf curl degree and the growth point damage degree 3 days after spraying (3 DAT), 7 days after spraying (7 DAT), 14 days after spraying (14 DAT) and 21 days after spraying (21 DAT): the case where the leaves are flat as untreated plants and the growth points are intact is defined as having a damage degree of 0%; the case where veins are locally browned, new leaves are malformed and plant growth is slow is defined as having a damage degree of 50%; and the case where veins are purple, until the whole plant is dead and the growth points are browned and dry is defined as having a damage degree of 100%. The soybean plants into which the ALT02M1-01 nucleotide sequence was introduced were of three strains in total (S1, S2 and S3), the soybean plants into which the ALT02M2-01 nucleotide sequence was introduced were of three strains in total (S4, S5 and S6), the soybean plants into which the ALT02M3-01 nucleotide sequence was introduced were of three strains in total (S7, S8 and S9), the soybean plants into which the ALT02-01 nucleotide sequence was introduced were of three strains in total (S10, S11 and S12), the control soybean plants were of two strains in total (S13 and S14), and the wild-type soybean plants were of one strain in total (CK1); and 10-15 plants were selected from each strain and tested. The results were as shown in Table 2 and FIG. 4.

TABLE 2

Experimental results of the herbicide tolerance of transgenic soybean T$_1$ plants

| Treatment | Soybean genotypes | Average damage % 3DAT | Average damage % 7DAT | Average damage % 14DAT | Average damage % 21DAT |
|---|---|---|---|---|---|
| Blank solvent | S1 | 0 | 0 | 0 | 0 |
| | S2 | 0 | 0 | 0 | 0 |

TABLE 2-continued

Experimental results of the herbicide tolerance of transgenic soybean $T_1$ plants

| Treatment | Soybean genotypes | Average damage % 3DAT | Average damage % 7DAT | Average damage % 14DAT | Average damage % 21DAT |
|---|---|---|---|---|---|
| (water) | S3 | 0 | 0 | 0 | 0 |
| | S4 | 0 | 0 | 0 | 0 |
| | S5 | 0 | 0 | 0 | 0 |
| | S6 | 0 | 0 | 0 | 0 |
| | S7 | 0 | 0 | 0 | 0 |
| | S8 | 0 | 0 | 0 | 0 |
| | S9 | 0 | 0 | 0 | 0 |
| | S10 | 0 | 0 | 0 | 0 |
| | S11 | 0 | 0 | 0 | 0 |
| | S12 | 0 | 0 | 0 | 0 |
| | S13 | 0 | 0 | 0 | 0 |
| | S14 | 0 | 0 | 0 | 0 |
| | CK1 | 0 | 0 | 0 | 0 |
| 144 g ai/ha tribenuron-methyl (8x Tri.) | S1 | 15 | 8 | 0 | 0 |
| | S2 | 16 | 9 | 0 | 0 |
| | S3 | 10 | 3 | 0 | 0 |
| | S4 | 0 | 0 | 0 | 0 |
| | S5 | 0 | 0 | 0 | 0 |
| | S6 | 0 | 0 | 0 | 0 |
| | S7 | 12 | 3 | 0 | 0 |
| | S8 | 11 | 2 | 0 | 0 |
| | S9 | 10 | 1 | 0 | 0 |
| | S10 | 25 | 15 | 5 | 0 |
| | S11 | 24 | 14 | 3 | 0 |
| | S12 | 30 | 17 | 4 | 0 |
| | S13 | 63 | 91 | 100 | 100 |
| | S14 | 58 | 95 | 100 | 100 |
| | CK1 | 76 | 87 | 100 | 100 |

Figure 4:
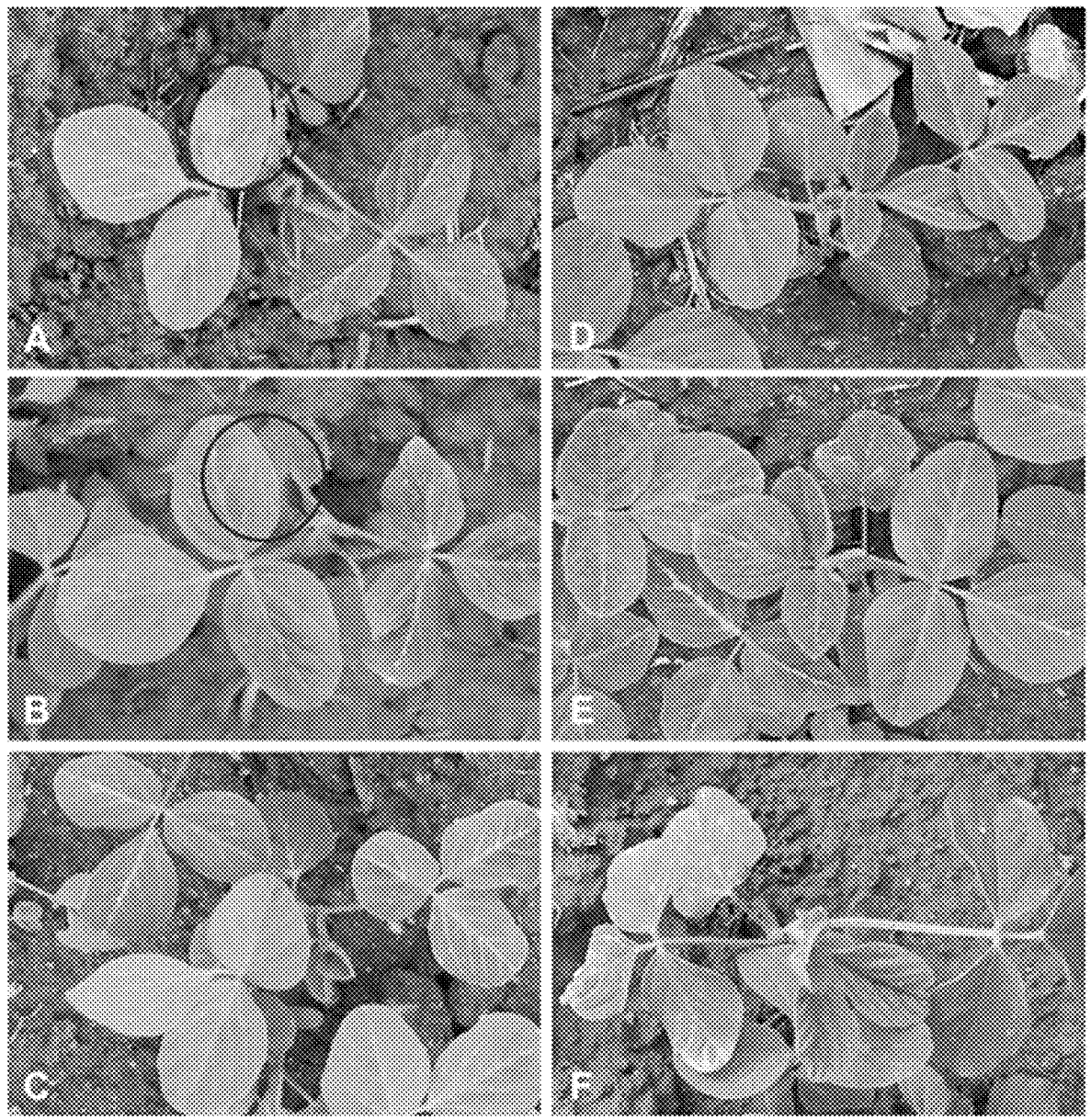
FIG. 4 is a diagram showing the tolerance of a transgenic soybean $T_1$ plant to benzenesulfonic acid for the herbicide tolerant protein, the coding gene thereof and a use thereof in the present invention; A: ALT02-01 transgenic soybean plant; B: ALT02M1-01 transgenic soybean plant; C: ALT02M2-01 transgenic soybean plant; D: ALT02M3-01 transgenic soybean plant; E: control soybean plant; F: wild-type soybean plant.

For soybeans, eight-fold field concentration of tribenuron-methyl is an effective dose for high pressure treatment. The results in Table 2 and FIG. 4 showed that the herbicide tolerant proteins ALT02M1-01, ALT02M2-01, ALT02M3-01 and ALT02-01 all can impart transgenic soybean plants with the tolerance to benzenesulfonic acid; compared with the soybean plants into which the ALT02-01 nucleotide sequence was introduced, all of the soybean plants into which the ALT02M1-01 nucleotide sequence was introduced, the soybean plants into which the ALT02M2-01 nucleotide sequence was introduced and the soybean plants into which the ALT02M3-01 nucleotide sequence was introduced had a significantly increased tolerance to benzenesulfonic acid; while the control soybean plants and the wild-type soybean plants had no tolerance to benzenesulfonic acid.

Example 7. Construction of Recombinant Expression Vectors for Maize

Figure 5:
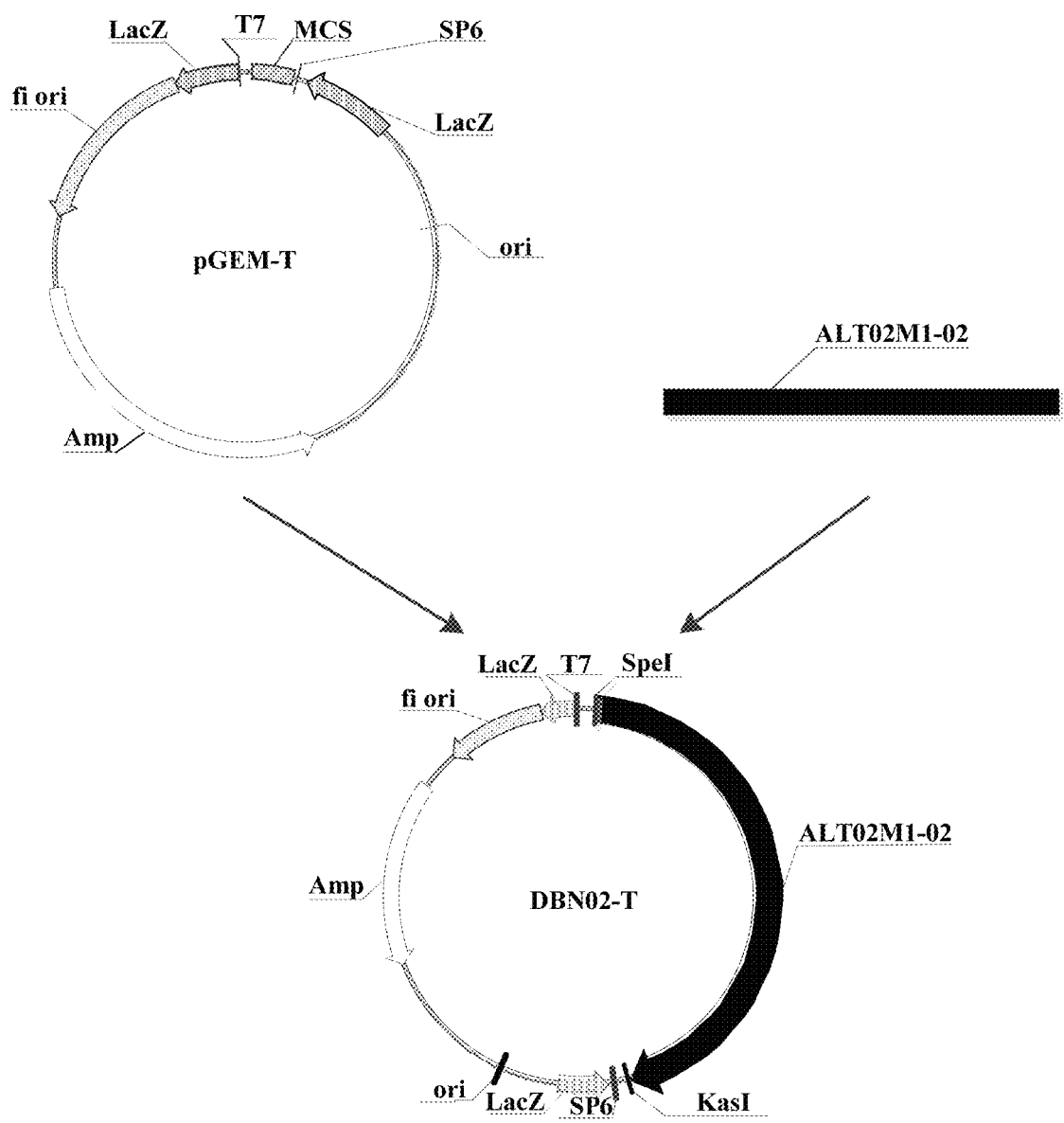
FIG. 5 is a construction flow chart of a recombinant cloning vector DBN02-T containing an ALT02M1-02 nucleotide sequence for the herbicide tolerant protein, the coding gene thereof and a use thereof in the present invention.

1. Construction of Recombinant Cloning Vectors Containing ALT02M1-02 Nucleotide Sequence for Maize The ALT02M1-02 nucleotide sequence was ligated into cloning vector pGEM-T (Promega, Madison, USA, CAT: A3600) according to the operational procedure in the instructions of product pGEM-T vector of Promega Corporation, thereby obtaining a recombinant cloning vector DBN02-T, the construction process of which is as shown in FIG. 5 (wherein, Amp represents the ampicillin resistance gene; fl represents the origin of replication of phage fl; LacZ is LacZ initiation codon; SP6 is SP6 RNA polymerase promoter; T7 is T7 RNA polymerase promoter; ALT02M1-02 is the ALT02M1-02 nucleotide sequence (SEQ ID NO: 26); and MCS is a multiple cloning site).

According to the method in Part 1 of Example 4, *Escherichia coli* $T_1$ competent cells were transformed with the recombinant cloning vector DBN01-T using the heat shock method, and the plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant cloning vector DBN02-T was the nucleotide sequence as shown in SEQ ID NO: 26 in the sequence listing, i.e., the ALT02M1-02 nucleotide sequence.

Figure 6:
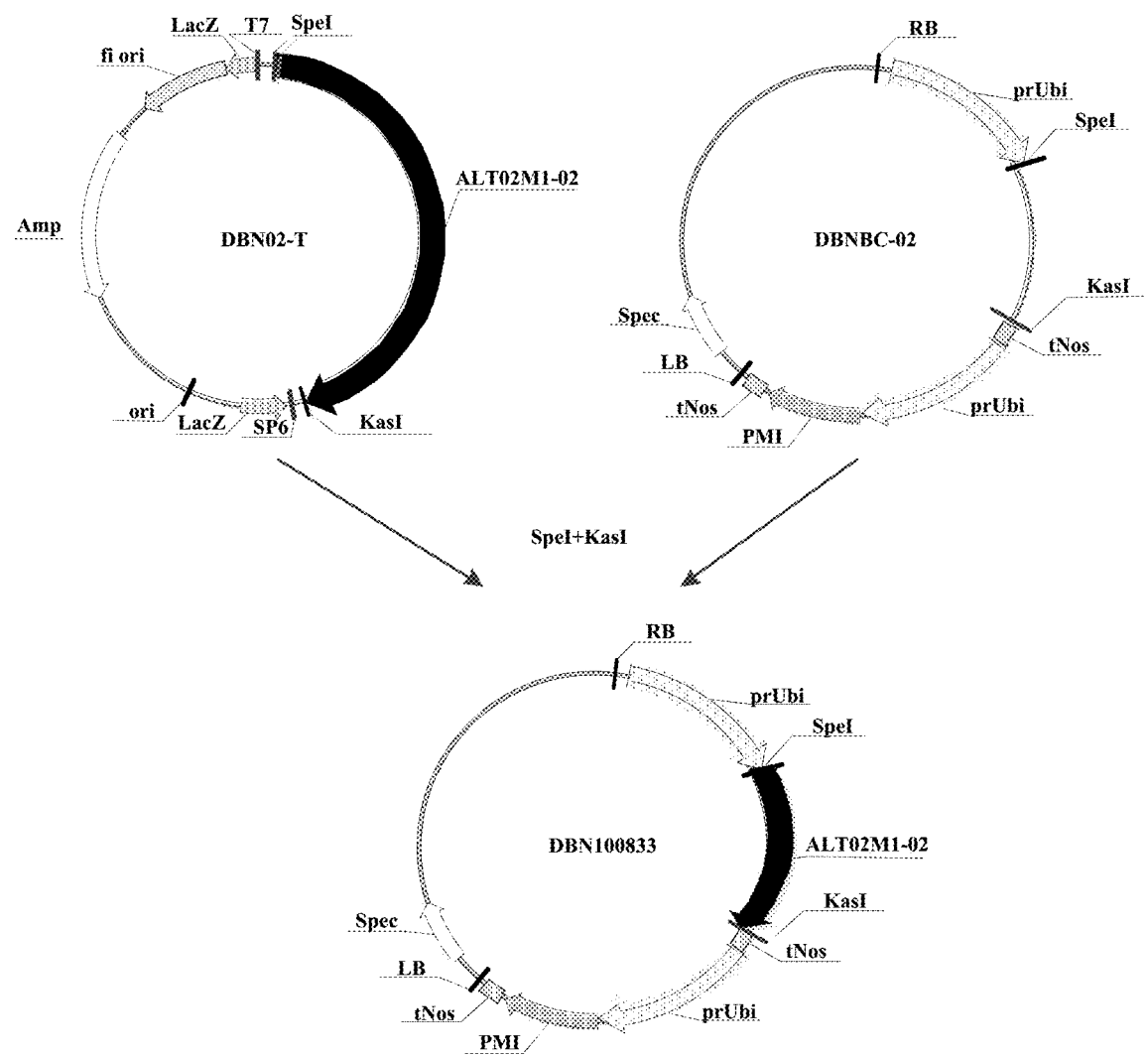
FIG. 6 is a construction flow chart of a recombinant expression vector DBN100833 containing an ALT02M1-02 nucleotide sequence for the herbicide tolerant protein, the coding gene thereof and a use thereof in the present invention.

2. Construction of Recombinant Expression Vectors Containing ALT02M1-02 Nucleotide Sequence for Maize The recombinant cloning vector DBN02-T and an expression vector DBNBC-02 (vector backbone: pCAMBIA2301 (which can be provided by the CAMBIA institution)) were both digested with restriction enzymes SpeI and KasI; the excised ALT02M1-02 nucleotide sequence fragment was inserted between the SpeI and KasI sites in the expression vector DBNBC-02; and it is well known to a person skilled in the art to construct a vector using conventional enzyme digestion methods, wherein a recombinant expression vector DBN100833 was constructed, the construction process of which was as shown in FIG. 6 (Spec: the spectinomycin gene; RB: the right boundary; prUbi: the maize Ubiquitin 1 gene promoter (SEQ ID NO: 78); ALT02M1-02: the ALT02M1-02 nucleotide sequence (SEQ ID NO:26); tNos: the terminator of a nopaline synthase gene (SEQ ID NO:70); PMI: the phosphomannose isomerase gene (SEQ ID NO: 79); LB: the left boundary).

According to the method in Part 2 of Example 4, *Escherichia coli* T1 competent cells were transformed with the recombinant expression vector DBN100833 using the heat shock method, and the plasmids in the cells were extracted through the alkaline method. The extracted plasmid was identified after digesting with restriction enzymes SpeI and KasI, and positive clones were identified by sequencing. The results showed that the nucleotide sequence between the SpeI and KasI sites in the recombinant expression vector DBN100833 was the nucleotide sequence as shown in SEQ ID NO: 26 in the sequence listing, i.e., the ALT02M1-02 nucleotide sequence.

The recombinant expression vector DBN100832 containing ALT02M2-02 nucleotide sequence, the recombinant expression vector DBN100831 containing ALT02M3-02 nucleotide sequence, and the recombinant expression vector DBN100830 containing ALT02-02 nucleotide sequence were constructed according to the method for constructing the recombinant expression vector DBN100833 containing ALT02M1-02 nucleotide sequence as described above. Positive clones were verified by sequencing, with the results showing that ALT02M2-02 nucleotide sequence, ALT02M3-02 nucleotide sequence and ALT02-02 nucleotide sequence inserted into the DBN100832, DBN100831 and DBN100830 were the nucleotide sequences as shown in SEQ ID NO: 30, SEQ ID NO: 34 and SEQ ID NO: 22 in the sequence listing respectively, namely ALT02M2-02 nucleotide sequence, ALT02M3-02 nucleotide sequence and ALT02-02 nucleotide sequence were inserted correctly.

Figure 7:
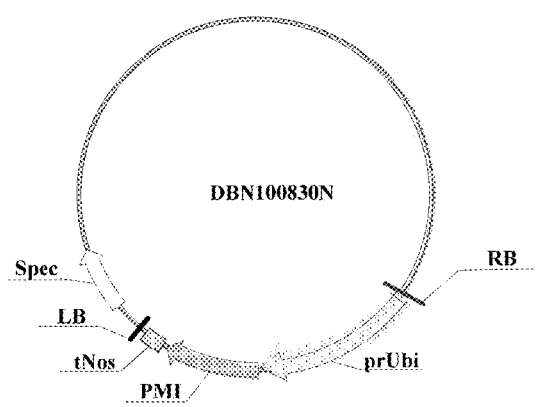
FIG. 7 is a schematic structural diagram of a control recombinant expression vector DBN100830N for the herbicide tolerant protein, the coding gene thereof and a use thereof in the present invention.

According to the method for constructing the recombinant expression vector DBN100833 containing ALT02M1-02 nucleotide sequence as described above, a control recombinant expression vector DBN100830N was constructed, the structure of which is as shown in FIG. 7 (vector backbone: pCAMBIA2301 (which can be provided by the CAMBIA institution); Spec: the spectinomycin gene; RB: the right boundary; prUbi: the maize Ubiquitin 1 gene promoter (SEQ ID NO: 78); PMI: the phosphomannose isomerase gene (SEQ ID NO: 79); tNos: the terminator of a nopaline synthase gene (SEQ ID NO:70); LB: the left boundary). Positive clones were verified by sequencing, with the results showing that the control recombinant expression vector DBN100830N was correctly constructed.

3. Transformation of *Agrobacterium* with the Recombinant Expression Vectors for Maize

*Agrobacterium* LBA4404 (Invitrogen, Chicago, USA, CAT: 18313-015) was transformed with the recombinant expression vectors DBN100833, DBN100832, DBN100831, DBN100830, and DBN100830N which had been constructed correctly using a liquid nitrogen method, under the following transformation conditions: placing 100 µL of *Agrobacterium* LBA4404, and 3 µL of plasmid DNA (recombinant expression vector) in liquid nitrogen for 10 minutes, and warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, spreading on an LB plate containing 50 mg/L of rifampicin and 50 mg/L of spectinomycin until positive single clones were grown, picking out single clones for culturing and extracting the plasmids thereof, and performing enzyme digestion verification using restriction enzymes. The results showed that the structures of the recombinant expression vectors DBN100833, DBN100832, DBN100831, DBN100830, and DBN100830N were completely correct.

Example 8. Acquisition and Verification of Transgenic Maize Plants

1. Acquisition of Transgenic Maize Plants

According to the conventionally used *Agrobacterium* infection method, young embryos of sterilely cultured maize variety Zong31 (Z31) were co-cultured with the *Agrobacterium* in Part 3 of Example 7, so as to introduce T-DNA (including the maize Ubiquitin1 gene promoter sequence, ALT02M1-02 nucleotide sequence, ALT02M2-02 nucleotide sequence, ALT02M3-02 nucleotide sequence and ALT02-02 nucleotide sequence, the PMI gene and the tNos terminator sequence) in the recombinant expression vectors DBN100833, DBN100832, DBN100831, DBN100830, and DBN100830N constructed in Part 2 of Example 7 into the maize chromosome set, thereby obtaining maize plants into which ALT02M1-02 nucleotide sequence was introduced, maize plants into which ALT02M2-02 nucleotide sequence was introduced, maize plants into which ALT02M3-02 nucleotide sequence was introduced and maize plants into which ALT02-02 nucleotide sequence was introduced; meanwhile, the control maize plants into which T-DNA in the control recombinant expression vector DBN100830N was introduced and wild type maize plants were used as the control.

As regards the *Agrobacterium*-mediated maize transformation, briefly, immature young embryos were separated from maize, and contacted with an *Agrobacterium* suspension, wherein the *Agrobacterium* can transfer the ALT02M1-02 nucleotide sequence (ALT02M2-02 nucleotide sequence, ALT02M3-02 nucleotide sequence or ALT02-02 nucleotide sequence) to at least one cell of one of the young embryos (step 1: the infection step). In this step, the young embryos were preferably immersed in an *Agrobacterium* suspension ($OD_{660}$=0.4-0.6, an infection culture medium (4.3 g/L of MS salt, MS vitamin, 300 mg/L of casein, 68.5 g/L of sucrose, 36 g/L of glucose, 40 mg/L of acetosyringone (AS), and 1 mg/L of 2,4-dichlorphenoxyacetic acid (2,4-D), with a pH of 5.3)) to initiate the inoculation. The young embryos were co-cultured with *Agrobacterium* for a period of time (3 days) (step 2: the co-culturing step). Preferably, the young embryos were cultured in a solid culture medium (4.3 g/L of MS salt, MS vitamin, 300 mg/L of casein, 20 g/L of sucrose, 10 g/L of glucose, 100 mg/L of acetosyringone (AS), 1 mg/L of 2,4-dichlorphenoxyacetic acid (2,4-D), and 8 g/L of agar, with a pH of 5.8) after the infection step. After this co-culturing stage, there can be an optional "recovery" step. In the "recovery" step, there may be at least one antibiotic (cephalosporin) known to inhibit the growth of *Agrobacterium* in a recovery culture medium (4.3 g/L of MS salt, MS vitamin, 300 mg/L of casein, 30 g/L of sucrose, 1 mg/L of 2,4-D, and 3 g/L of phytagel, with a pH of 5.8), without the addition of a selective agent for a plant transformant (step 3: the recovery step). Preferably, the young embryos were cultured in a solid culture medium with an antibiotic, but without a selective agent, in order to eliminate *Agrobacterium* and provide a recovery stage for the infected cells. Subsequently, the inoculated young embryos were cultured in a culture medium containing a selective agent (mannose), and growing transformed calli were selected (step 4: the selection step). Preferably, the young embryos were cultured in a screening solid culture medium (4.3 g/L of MS salt, MS vitamin, 300 mg/L of casein, 30 g/L of sucrose, 12.5 g/L of mannose, 1 mg/L of 2,4-D, and 3 g/L of phytagel, with a pH of 5.8) with a selective agent, resulting in the selective growth of transformed cells. Then, plants were regenerated from the calli (step 5: the regeneration step). Preferably, the calli grown in a culture medium containing a selective agent were cultured in solid culture media (an MS differentiation culture medium and MS rooting culture medium) to regenerate plants.

Resistant calli obtained from screening were transferred onto the MS differentiation culture medium (4.3 g/L of MS salt, MS vitamin, 300 mg/L of casein, 30 g/L of sucrose, 2 mg/L of 6-benzyladenine, 5 g/L of mannose, and 3 g/L of phytagel, with a pH of 5.8), and cultured at 25° C. for differentiation. The differentiated seedlings were transferred onto the MS rooting culture medium (2.15 g/L of MS salt, MS vitamin, 300 mg/L of casein, 30 g/L of sucrose, 1 mg/L of indole-3-acetic acid, and 3 g/L of phytagel, with a pH of 5.8), cultured at 25° C. to a height of about 10 cm, and transferred to a greenhouse for culturing until fruiting. In the greenhouse, the plants were cultured at 28° C. for 16 hours, and then cultured at 20° C. for 8 hours every day.

2. Verification of the Transgenic Maize Plants Using TaqMan

The maize plant into which the ALT02M1-02 nucleotide sequence was introduced, the maize plant into which the ALT02M2-02 was introduced, the maize plant into which the ALT02M3-02 was introduced, the maize plant into which the ALT02-02 was introduced and the control maize plant were detected and analyzed according to the method for verifying transgenic soybean plants with TaqMan as described in part 2 of Example 5. The copy number of the PMI gene was detected by the Taqman probe fluorescence quantitative PCR method so as to determine the copy number of the target gene. Meanwhile, wild-type maize plants were used as the control, and detected and analyzed according to the above-mentioned method. Triple repeats were set for the experiments, and were averaged.

The following primers and probe were used to detect the PMI gene sequence:

```
primer 7:
GCTGTAAGAGCTTACTGAAAAAATTAACA
as shown in SEQ ID NO: 80 in the sequence listing;

primer 8:
CGATCTGCAGGTCGACGG
as shown in SEQ ID NO: 81 in the sequence listing;

probe 2:
TCTCTTGCTAAGCTGGGAGCTCGATCC
as shown as SEQ ID NO: 82
``` in the sequence listing.

It was further demonstrated, by analyzing the experimental results of the copy number of PMI gene, that the ALT02M1-02 nucleotide sequence, the ALT02M2-02 nucleotide sequence, the ALT02M3-02 nucleotide sequence and the ALT02-02 nucleotide sequence had all been integrated into the chromosome set of the detected maize plants, and all of the maize plants into which the ALT02M1-02 nucleotide sequence was introduced, the maize plants into which the ALT02M2-02 nucleotide sequence was introduced, the maize plants into which the ALT02M3-02 nucleotide sequence was introduced, the maize plants into which the ALT02-02 nucleotide sequence was introduced and control maize plants resulted in single-copy transgenic maize plants.

Example 9. Detection of Herbicide Tolerance Effects of the Transgenic Maize Plants The effect of herbicide tolerance to tribenuron-methyl was detected on the maize plants into which the ALT02M1-02 nucleotide sequence was introduced, maize plants into which the ALT02M2-02 nucleotide sequence was introduced, maize plants into which the ALT02M3-02 nucleotide sequence was introduced, maize plants into which the ALT02-02 nucleotide sequence was introduced, control maize plants and wild-type maize plants (at V3-V4 stages) respectively.

The maize plants into which the ALT02M1-02 nucleotide sequence was introduced, the maize plants into which the ALT02M2-02 nucleotide sequence was introduced, the maize plants into which the ALT02M3-02 nucleotide sequence was introduced, the maize plants into which the ALT02-02 nucleotide sequence was introduced, control maize plants and wild-type maize plants were taken and sprayed with tribenuron-methyl (144 g ai/ha, eight-fold field concentration) or a blank solvent (water), respectively. The degree of damage caused by the herbicide was measured for each plant according to the plant growth status 3 days after spraying (3 DAT), 7 days after spraying (7 DAT), 14 days after spraying (14 DAT) and 21 days after spraying (21 DAT): a growth status equivalent to that of the untreated plants is defined as having a damage degree of 0%; the case where leaves are locally chlorotic and yellow but the normal plant growth is substantially not affected is defined as having a damage degree of 50%; and the case where the whole plant is purple and dying is defined as having a damage degree of 100%. The maize plants into which the ALT02M1-02 nucleotide sequence was introduced were of three strains in total (S15, S16 and S17), the maize plants into which the ALT02M2-02 nucleotide sequence was introduced were of three strains in total (S18, S19 and S20), the maize plants into which the ALT02M3-02 nucleotide sequence was introduced were of three strains in total (S21, S22 and S23), the maize plants into which the ALT02-02 nucleotide sequence was introduced were of three strains in total (S24, S25 and S26), the control maize plants were of two strains in total (S27 and S28), and the wild-type maize plants were of one strain in total (CK2); and 10-15 plants were selected from each strain and tested. The results were as shown in Table 3 and FIG. 8.

TABLE 3

Experimental results of the herbicide tolerance of transgenic maize $T_1$ plants

| Treatment | Maize genotypes | Average damage % 3DAT | Average damage % 7DAT | Average damage % 14DAT | Average damage % 21DAT |
|---|---|---|---|---|---|
| Blank solvent (water) | S15 | 0 | 0 | 0 | 0 |
| | S16 | 0 | 0 | 0 | 0 |
| | S17 | 0 | 0 | 0 | 0 |
| | S18 | 0 | 0 | 0 | 0 |
| | S19 | 0 | 0 | 0 | 0 |
| | S20 | 0 | 0 | 0 | 0 |
| | S21 | 0 | 0 | 0 | 0 |
| | S22 | 0 | 0 | 0 | 0 |
| | S23 | 0 | 0 | 0 | 0 |
| | S24 | 0 | 0 | 0 | 0 |
| | S25 | 0 | 0 | 0 | 0 |
| | S26 | 0 | 0 | 0 | 0 |
| | S27 | 0 | 0 | 0 | 0 |
| | S28 | 0 | 0 | 0 | 0 |
| | CK2 | 0 | 0 | 0 | 0 |
| 144 g ai/ha tribenuron-methyl (8x Tri.) | S15 | 5 | 0 | 0 | 0 |
| | S16 | 6 | 0 | 0 | 0 |
| | S17 | 3 | 0 | 0 | 0 |
| | S18 | 0 | 0 | 0 | 0 |
| | S19 | 0 | 0 | 0 | 0 |
| | S20 | 0 | 0 | 0 | 0 |
| | S21 | 3 | 0 | 0 | 0 |
| | S22 | 2 | 0 | 0 | 0 |
| | S23 | 0 | 0 | 0 | 0 |
| | S24 | 14 | 5 | 0 | 0 |
| | S25 | 15 | 4 | 0 | 0 |
| | S26 | 20 | 7 | 0 | 0 |
| | S27 | 61 | 82 | 100 | 100 |
| | S28 | 53 | 78 | 100 | 100 |
| | CK2 | 46 | 86 | 100 | 100 |

Figure 8:
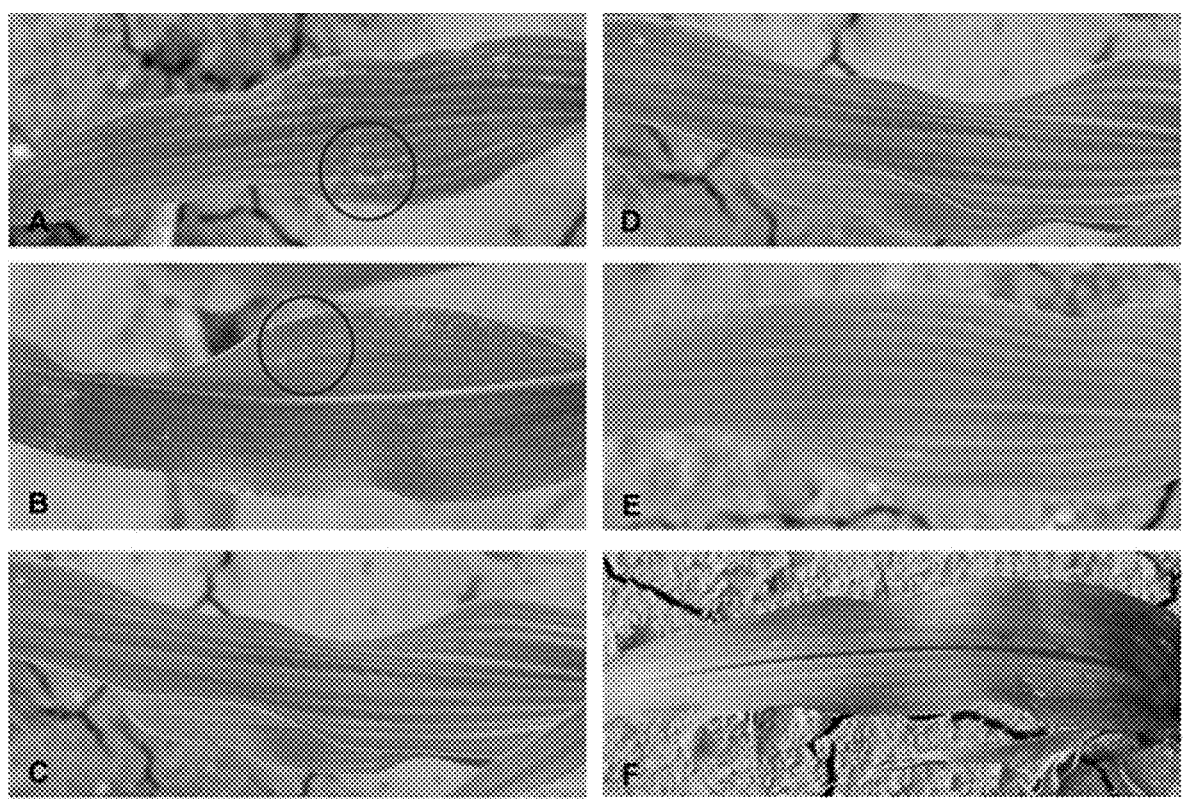
FIG. 8 is a diagram showing the tolerance of a transgenic maize $T_1$ plant to benzenesulfonic acid for the herbicide tolerant protein, the coding gene thereof and a use thereof in the present invention; A: ALT02-02 transgenic maize plant; B: ALT02M1-02 transgenic maize plant; C: ALT02M2-02 transgenic maize plant; D: ALT02M3-02 transgenic maize plant; E: control maize plant; F: wild-type maize plant.

For the maize, eight-fold field concentration of tribenuron-methyl is an effective dose for high pressure treatment. The results in Table 3 and FIG. 8 showed that the herbicide tolerant proteins ALT02M1-02, ALT02M2-02, ALT02M3-02 and ALT02-02 all can impart transgenic maize plants with the tolerance to benzenesulfonic acid; compared with the maize plants into which the ALT02-02 nucleotide sequence was introduced, all of the maize plants into which the ALT02M1-02 nucleotide sequence was introduced, the maize plants into which the ALT02M2-02 nucleotide sequence was introduced and the maize plants into which the ALT02M3-02 nucleotide sequence was introduced had a significantly increased tolerance to benzenesulfonic acid; while the control maize plants and the wild-type maize plants had no tolerance to benzenesulfonic acid.

In conclusion, the herbicide tolerant protein ALT01 of the present invention can exhibit a higher tolerance to sulfonylurea herbicides, particularly tribenuron-methyl when its amino acid sequence is mutated at position 176 from glycine to alanine and/or at position 178 from serine to valine (such as the herbicide tolerant proteins ALT01M1, ALT01M2 or ALT01M3); the herbicide tolerant protein ALT02 (or ALT03) can exhibit a higher tolerance to sulfonylurea herbicides, particularly tribenuron-methyl when its amino acid sequence is mutated at position 140 from glycine to alanine and/or at position 142 from serine to valine (such as the herbicide tolerant proteins ALT02M1, ALT02M2, ALT02M3, ALT03M1, ALT03M2 or ALT03M3); the herbicide tolerant protein ALT04 can exhibit a higher tolerance to sulfonylurea herbicides, particularly tribenuron-methyl when its amino acid sequence is mutated at position 131 from glycine to alanine and/or at position 133 from serine to valine (such as the herbicide tolerant proteins ALT04M1, ALT04M2 or ALT04M3). Moreover, the coding genes of the above-mentioned herbicide tolerant proteins are particularly suitable for expression in plants due to the use of the preferred codons of plants. The soybean and maize plants into which the above-mentioned herbicide tolerant proteins are introduced have a strong tolerance to sulfonylurea herbicides, and can tolerate tribenuron-methyl of an eight-fold field concentration particularly. Therefore, the above-mentioned herbicide tolerant proteins have a broad application prospect in plants.

Finally, it should be stated that the above examples are merely used for illustrating, rather than limiting, the technical solution of the present invention; and although the present invention has been described in detail with reference to the preferred examples, a person skilled in the art should understand that modifications or equivalent substitutions may be made to the technical solution of the present invention without departing from the spirit and scope of the technical solution of the present invention.

The invention claimed is:

1. An herbicide tolerance protein, comprising: the amino acid sequence as shown in SEQ ID NO: 27.

2. The herbicide tolerance protein according to claim 1, wherein the herbicide tolerance protein consists of the amino acid sequence as shown in SEQ ID NO: 27.

3. An herbicide tolerance protein, comprising the amino acid sequence as shown in SEQ ID NO: 31.

4. The herbicide tolerance protein according to claim 3, wherein the herbicide tolerance protein consists of the amino acid sequence as shown in SEQ ID NO: 31.

5. A method of making an herbicide tolerant plant, comprising: co-expressing the herbicide tolerance protein of claim 2 in said plant together with at least one additional protein which is different from the herbicide tolerance protein of claim 2.

6. A method of making an herbicide tolerant plant, comprising: co-expressing the herbicide tolerance protein of claim 3 in said plant together with at least one additional protein which is different from the herbicide tolerance protein of claim 3.

7. A method of making an herbicide tolerant plant, comprising: co-expressing the herbicide tolerance protein of claim 4 in said plant together with at least one additional protein which is different from the herbicide tolerance protein of claim 4.

8. The method according to claim 5, wherein the additional protein is 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome-like proteins or protoporphyrinogen oxidase.

9. A method of making an herbicide tolerant plant, comprising: co-expressing the herbicide tolerance protein of claim 1 in said plant together with at least one additional protein which is different from the herbicide tolerance protein of claim 1.

* * * * *